US008349801B2

(12) United States Patent
Cohen et al.

(10) Patent No.: US 8,349,801 B2
(45) Date of Patent: Jan. 8, 2013

(54) PEPTIDE LIGANDS FOR G-PROTEIN COUPLED RECEPTORS

(75) Inventors: Yossi Cohen, Woking (GB); Ronen Shemesh, Modiin (IL); Amir Toporik, Azur (IL); Zurit Levine, Herzlia (IL); Assaf Wool, Kiryat-Ono (IL); Dvir Dahary, Tel-Aviv (IL); Iris Hecht, Tel Aviv (IL); Merav Beiman, Ness Ziona (IL); Galit Rotman, Herzlia (IL); Michal Ayalon-Soffer, Ramat-HaSharon (IL)

(73) Assignee: Compugen Ltd., Tel-Aviv (IL)

( * ) Notice: Subject to any disclaimer, the term of this patent is extended or adjusted under 35 U.S.C. 154(b) by 1432 days.

(21) Appl. No.: 11/901,939

(22) Filed: Sep. 18, 2007

(65) Prior Publication Data

US 2012/0129776 A1 May 24, 2012

Related U.S. Application Data

(60) Provisional application No. 60/845,606, filed on Sep. 18, 2006, provisional application No. 60/846,421, filed on Sep. 21, 2006, provisional application No. 60/851,591, filed on Oct. 12, 2006.

(51) Int. Cl.
*A61K 38/08* (2006.01)
*A61K 38/10* (2006.01)
*A61K 38/16* (2006.01)
*C07K 7/06* (2006.01)
*C07K 7/08* (2006.01)
*C07K 14/00* (2006.01)

(52) U.S. Cl. ............ 514/15.6; 514/15.7; 514/16.4; 514/20.6; 514/21.3; 514/21.4; 514/21.6; 514/21.7; 514/21.8; 530/324; 530/325; 530/326; 530/327; 530/329; 530/330

(58) Field of Classification Search .................. None
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | |
| 4,078,052 A | 3/1978 | Papahadjopoulos | |
| 4,195,128 A | 3/1980 | Hildebrand et al. | |
| 4,224,179 A | 9/1980 | Schneider | |
| 4,229,537 A | 10/1980 | Hodgins et al. | |
| 4,235,871 A | 11/1980 | Papahadjopoulos et al. | |
| 4,247,642 A | 1/1981 | Hirohara et al. | |
| 4,308,166 A | 12/1981 | Marchetti et al. | |
| 4,310,506 A | 1/1982 | Baldeschwieler et al. | |
| 4,330,440 A | 5/1982 | Ayers et al. | |
| 4,394,372 A | 7/1983 | Taylor | |
| 4,485,054 A | 11/1984 | Mezei et al. | |
| 4,508,703 A | 4/1985 | Redziniak et al. | |
| 4,552,803 A | 11/1985 | Pearson | |
| 4,588,578 A | 5/1986 | Fountain et al. | |
| 4,816,567 A | 3/1989 | Cabilly et al. | |
| 4,975,282 A | 12/1990 | Cullis et al. | |
| 5,008,050 A | 4/1991 | Cullis et al. | |
| 5,030,453 A | 7/1991 | Lenk et al. | |
| 5,059,421 A | 10/1991 | Loughrey et al. | |
| 5,169,637 A | 12/1992 | Lenk et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,620,985 B1* | 9/2003 | Glazebrook et al. ......... 800/278 |
| 7,884,180 B2* | 2/2011 | Cohen et al. ................. 530/300 |
| 2003/0152921 A1 | 8/2003 | Edwards et al. | |
| 2004/0235923 A1* | 11/2004 | Abe et al. ...................... 514/400 |
| 2006/0034852 A1 | 2/2006 | Rixon et al. | |
| 2009/0054342 A1 | 2/2009 | Cohen et al. | |
| 2011/0104217 A1 | 5/2011 | Cohen et al. | |

FOREIGN PATENT DOCUMENTS

| | | |
|---|---|---|
| EP | 1559721 | 8/2005 |
| EP | 2064234 | 6/2009 |
| WO | WO 87/05330 | 9/1987 |
| WO | WO 99/65465 | 12/1999 |
| WO | WO 2006/050247 | 5/2006 |
| WO | WO 2006/050247 A2 | 5/2006 |
| WO | WO 2006/050262 | 5/2006 |
| WO | WO 2006/050262 A2 | 5/2006 |
| WO | WO 2009/019531 | 2/2009 |

OTHER PUBLICATIONS

Anderson et al., "Glutathione Monoethyl Ester: Preparation, Uptade by Tissues, and Conversion to Glutathione", *Arch. Biochem. Biophys.*, 239(2):538-548 (1985).
Dittert et al., "Hydrolysis of 4-Acetamidophenyl 2,2,2-Trichloroethyl Carbonate by Esterolytic Enzymes from Various Sources", *J. Pharm. Sci.*, 58(5):557-559 (1969).
Dittert et al., "Carbonate Ester Prodrug of Salicylic Acid", *J. Pharm. Sci.*, 57(5):828-831 (1968).
Dittert et al., "Acetaminophen Prodrugs II". *J. Pharm. Sci.*, 57(5):780-783 (1968).
King et al., "Interaction of Carboxypeptidase A with Carbamate and Carbonate Esters", *Biochem.*, 26:2294-2300 (1987).
Lindberg et al., "Metabolism of Bambuterol in Rat Liver Microsomes: Identification of Hydroxylated and Demethylated Products by Liquid Chromatography Mass Spectrometry", *Drug Metab. Disp.*, 17(3):311-322 (1989).
Singhal et al., "Glutathione, a first line of defense against cadmium toxicity", *FASEB J.*, 1:220-223 (1987).
Tunek et al., "Hydrolysis of $^3$H-Bambuterol, a Carbamate Prodrug of Terbutaline, in Blood from Humans and Laboratory Animals In Vitro", *Biochem. Pharmacol.*, 37(20):3867-3876 (1988).
Ahmad et al., "Novel G protein-coupled receptors as pain targets", *Current Opin. Invest. Drugs*, 5(1):67-70 (2004).
Allison, A.C., "The Mode of Action of Immunological Adjuvants", *Dev. Biol. Stand.*, 92:3-11 (1998).
Aplin et al., "Preparation, Properties, and Applications of Carbohydrate Conjugates of Proteins and Lipids", *CRC Crit. Rev. Biochem.*, 22:259-306 (1981).

(Continued)

*Primary Examiner* — Jeffrey E Russel

(57) ABSTRACT

Disclosed are peptide ligands for G-protein coupled receptors that are useful for treating myocardial and ischemic disorders associated with G-protein coupled receptor activation.

12 Claims, 29 Drawing Sheets

OTHER PUBLICATIONS

Bangham et al., "Diffusion of Univalent Ions across the Lamellae of Swollen Phospholipids", *J. Mol. Biol.*, 13:238-252 (1965).

Bedu-Addo et al., "Interaction of Polyethyleneglycol-Phospholipid Conjugates with Cholesterol-Phosphatidylcholine Mixtures: Sterically Stabilized Liposome Formulations", *Pharmacol. Res.*, 13(5):718-724 (1996).

Boerner et al., "Production of Antigen-Specific Human Monoclonal Antibodies from in Vitro-Primed Human Splenocytes", *J. Immunol.*, 147(1):86-95 (1991).

Brisson et al., "Expression of a bacterial gene in plants by using a viral vector", *Nature*, 310:511-514 (1984).

Broglie et al., "Light-Regulated Expression of a Pea Ribulose-1,5-Bisphosphate Carboxylase Small Subunit Gene in Transformed Plant Cells", *Science*, 224(4651):838-843 (1984).

Chang et al., "Procedures for Microencapsulation of Enzymes, Cells and Genetically Engineered Microorganisms", *Mol. Biotechnol.*, 17:249-260 (2001).

Chia et al., "Multi-layered microcapsules for cell encapsulation", *Biomaterials*, 23(3):849-856 (2002).

Chiang et al., "The Lipoxin Receptor ALX: Potent Ligand-Specific and Stereoselective Actions in Vivo", *Pharmacol. Rev.*, 58(3):463-487 (2006).

Cole et al., "The EBV-Hybridoma Technique and Its Application to Human Lung Cancer", *Monoclonal Antibodies Can. Ther.*, pp. 77-96 (1985).

Coruzzi et al., "Tissue-specific and light-regulated expression of a pea nuclear gene encoding the small subunit of ribulose-1,5-bisphosphate carboxylase", *EMBO J.*, 3(8):1671-1679 (1984).

De Mello, W.C., "Angiotensin (1-7) re-establishes impulse conduction in cardiac muscle during ischaemia-reperfusion. The role of the sodium pump", *J. Renin-Angiotensin-Aldosterone Sys.*, 5(4):203-208 (2004).

DiMaio et al., "Synthesis of Chiral Piperazin-2-ones as Model Peptidomimetics", *J. Chem. Soc. Perkin Trans.*, pp. 1687-1689 (1989).

Dong et al., "A Diverse Family of GPCRs Expressed in Specific Subsets of Nociceptive Sensory Neurons", *Cell*, 106:619-632 (2001).

Dray, A., "Novel molecular targets in pain control", *Curr. Opin. in Anaesthol.*, 16:521-525 (2003).

Edge et al., "Deglycosylation of Glycoproteins by Trifluoromethanesulfonic Acid", *Anal. Biochem.*, 118(1):131-137 (1981).

Ferreira et al., "Angiotensin-(1-7): Cardioprotective Effect in Myocardial Ischemia/ Reperfusion", *Hypertension*, 38:665-668 (2001).

Ferreira et al., "Angiotensin-(1-7) improves the post-ischemic function in isolated perfused rat hearts", *Braz. J. Med.Biol. Res.*, 35:1083-1090 (2002).

Ferrario, C.M., "Role of Angiotensin II in Cardiovascular Disease—Therapeutic Implications of More Than a Century of Research", *J. Renin-Angiotensin-Aldosterone Sys.*, 7(1):3-14 (2006).

Fishwild et al., "High-avidity human IgGκ monoclonal antibodies from a novel strain of minilocus transgenic mice", *Nat. Biotechnol.*, 14(7):845-851 (1996).

Garvey et al., "3,4-Disubstituted γ-Lactam Rings as Conformationally Constrained Mimics of Peptide Derivatives Containing Aspartic Acid or Norleucine", *J. Org. Chem.*, 55:936-940 (1990).

Gavins et al., "A twist in anti-inflammation: Annexin 1 acts via the lipoxin $A_4$ receptor", *Prostaglandins Leukotrienes and Essential Fatty Acids*, 73:211-219 (2004).

Gavins et al., "Formyl-peptide receptor is not involved in the protection afforded by annexin 1 in murine acute myocardial infarct", *FASEB J.*, 19:100-102 (2005).

Gewirtz, A.T., "Lipoxin analogs: Novel anti-inflammatory mediators", *Curr. Opin. Invest. Drugs*, 6(11):1112-1115(2005).

Gilchrist, A., "Second Annual GPCRs: From Orphan to Blockbuster", *Expert Opin. Ther. Targets*, 8(5):495-498 (2004).

Gilding, D.K., "Biodegradable polymers", in *Biocompatibility of Clinical Implant Materials*, Chapter 9, pp. 209-232 (1981).

Gonzalez-Rey et al., "Cortistatin as a Potential Multistep Therapeutic Agent for Inflammatory Disorders", *Drug News Perspect*, 19(7):393-399 (2006).

Gurley et al., "Upstream Sequences Required for Efficient Expression of a Soybean Heat Shock Gene", *Mol. Cell. Biol.*, 6(2):559-565 (1986).

Hanes et al., "Polymer Microspheres for Vaccine Delivery", in *Vaccine Design: The Subunit and Adjuvant Approach*, Chapter 16, pp. 389-412, Plenum Press, New York (1995).

Hoogenboom et al., "By-passing Immunisation: Human Antibodies from Synthetic Repertoires of Germline $V_H$ Gene Segments Rearranged in Vitro", *J. Mol. Biol.*, 227:381-388 (1992).

Hopkins et al., "The druggable genome", *Nat. Rev.*, 1:727-730 (2002).

Huang, C., "Studies on Phosphatidylcholine Vesicles. Formation and Physical Characteristics", *Biochemistry*, 8(1):334-352 (1969).

Jacoby et al., "The 7TM G-Protein-Coupled Receptor Target Family", *ChemMedChem*, 1:761-782 (2006).

Jones et al., "Amide Bond Isosteres: Imidazolines in Pseudopeptide Chemistry", *Tetrahedron Lett.*, 29(31):3853-3856 (1988).

Jones et al., "Replacing the complementarity-determining regions in a human antibody with those from a mouse", *Nature*, 321(6069):522-525 (1986).

Kamohara et al., "Identification of MrgX2 as a human G-protein-coupled receptor for proadrenomedullin N-terminal peptides", *Biochem. Biophys. Res. Comm.*, 330:1146-1152 (2005).

Kazmierski et al., "Topographic Design of Peptide Neurotransmitters and Hormones on Stable Backbone Templates: Relation of Conformation and Dynamics to Bioactivity", *J. Am. Chem. Soc.*, 113(6):2275-2283 (1991).

Keidar et al., "ACE2 of the heart: From angiotensin I to angiotensin (1-7)", *Cardiovasc. Res.*, 73:463-469 (2007).

Kemp et al., "(2S, 5S, 11S)-1-Acetyl-1, 4-Diaza-3-Keto-5-Carboxy-10-Thia-Tricyclo-[$2.8.0^{4,8}$]-Tridecane, 1 the Preferred Conformation of 1 (1= αTemp-OH) and its Peptide Conjugates αTemp-L-(Ala)$_n$-OR (n=1 to 4) and α-Temp-L-Ala-L-Phe-L-Lys(e-Boc)-NHMe Studies of Templates for α-Helix Formation", *Tetrahedron Lett.*, 29(39):4935-4938 (1988).

Kemp et al., "A Convenient Preparation of Derivatives of 3(S)-Amino-10(R)-Carboxyl-1, 6-Diaza-Cyclodeca-2, 7-Dione the Dilactam of L-α, γ-Diaminobutyric Acid and D-Glutamic of Acid: A β-Turn Template", *Tetrahedron Lett.*, 29(40):5057-5060 (1988).

Kemp et al., "Amino Acid Derivatives That Stabilize Secondary Structures of Polypeptides. 4. Practical Synthesis of 4-(Alkylamino)-3-cyano-6-azabicyclo[3.2.1]oct-3-enes (Ben Derivatives) as γ-Turn Templates", *J. Org. Chem.*, 54(1):109-115 (1989).

Kemp et al., "Conformational Analysis of Peptide-Functionalized Diacylaminoepindolidiones $^1$H NMR Evidence for β-Sheet Formation", *Tetrahedron Lett.*, 29(40):5081-5082 (1988).

Kemp et al., "Conformationally Restricted Cyclic Nonapeptides Derived from L-Cysteine and LL-3-Amino-2-piperidone-6-carboxylic Acid (LL-Acp), a Potent β-Turn-Inducing Dipeptide Analogue", *J. Org. Chem.*, 50(26):5834-5838 (1985).

Kobayashi et al., "Pathophysiological Function of Adrenomedullin and Proadrenomedullin N-Terminal Peptides in Adrenal Chromaffin Cells", *Hypertens Res.*, 26(Suppl.):S71-S78 (2003).

Kucharewicz et al., "Antithrombotic Effect of Captropril and Losartan Is Mediated by Angiotensin-(1-7)", *Hypertension*, 40:774-779 (2002).

Kunz, H., "Synthesis of Glycopeptides, Partial Structures of Biological Recognition Components", *Angew. Chem. Int. Ed. Engl.*, 26:294-308 (1987).

La et al., "Annexin 1 peptides protect against experimental myocradial ischemia-reperfusion: analysis of their mechanism of action", *FASEB J.*, 15:2247-2256 (2001).

Lamoyi et al., "Preparation of F(ab')$_2$ Fragments from Mouse IgG of Various Subclasses", *J. Immunol. Meth.*, 56(1):235-243 (1983).

Langer, R., "Biomaterials in Drug Delivery and Tissue Engineering: One Laboratory's Experience", *Acc. Chem. Res.*, 33:94-101 (2000).

Langer et al., "Selected advances in drug delivery and tissue engineering", *J. Controlled Release*, 62(1-2):7-11 (1999).

Larrick et al., "PCR Amplification of Antibody Genes", *Methods: A Companion to Methods in Enzymology*, 2(2):106-110 (1991).

Le et al., "Pleiotropic roles of formyl peptide receptors", *Cytokine and Growth Factor Reviews*, 12:91-105 (2001).

Lembo et al., "Proenkephalin A gene products activate a new family of sensory neuron-specific GPCRs", *Nat. Neurosci.*, 5(3):201-209 (2002).

Lemos et al., "The Endothelium-Dependent Vasodilator Effect of the Nonpeptide Ang(1-7) Mimic AVE 0991 Is Abolished in the Aorta of Mas-Knockout Mice", *J. Cardiovasc. Pharmacol.*, 46(3):274-279 (2005).

Litzinger et al., "Effect of liposome size on the circulation time and intraorgan distribution of amphipathic poly(ethylene glycol)-containing liposomes", *Biochim. Biophys. Acta*, 1190:99-107 (1994).

Lonberg et al., "Antigen-specific human antibodies from mice comprising four distinct genetic modifications", *Nature*, 368:856-859 (1994).

Lonberg et al., "Human Antibodies from Transgenic Mice", *Intern. Rev. Immunol.*, 13:65-93 (1995).

Lu et al., "A novel cell encapsulation method using photosensitive poly(allylamine α-cyanocinnamylideneacetate)", *J. Microencapsul.*, 17(2):245-251 (2000).

Lu et al., "Cell encapsulation with alginate and α-phenoxycinnamylidene-acetylated poly(allylamine)", *Biotechnol. Bioeng.*, 70(5):479-483 (2000).

Marks et al., "By-Passing Immunization: Building High Affinity Human Antibodies by Chain Shuffling", *Bio Tech.*, 10(7):779-783 (1992).

Marks et al., "By-passing Immunization: Human Antibodies from V-gene Libraries Displayed on Phage", *J. Mol. Biol.*, 222(3):581-597 (1991).

Mathiowitz et al., "Novel Microcapsules for Delivery Systems", *Reactive Polymers*, 6:275-283 (1987).

Mathiowitz et al., "Polyanhydride Microspheres as Drug Carriers: I. Hot-Melt Microencapsulation", *J. Controlled Release*, 5(1):13-22 (1987).

Mathiowitz et al., "Polyanhydride Microspheres as Drug Carriers.: II. Microcencapsulation by Solvent Removal", *J. Appl. Polymer Sci.*, 35:755-774 (1988).

Miyake et al., "1,2,3,4-Tetrahydroisoquinoline-3-carboxylic Acid Angiotensin", *J. Takeda Res. Labs*, 43(3/4):53-76 (1984) (English Abstract Only).

Morrison, S.L., "Success in specification", *Nature*, 368:812-813 (1994).

Nagai et al., "Synthesis of a Bicyclic Dipeptide with the shape of β-Turn Central Part", *Tetrahedron Lett.*, 26(5):647-650 (1985).

Neuberger, M., "Generating high-avidity human Mabs in mice", *Nat. Biotechnol.*, 14(7):826 (1996).

Nothacker et al., "Proadrenomedullin N-terminal peptide and cortistatin activation of MrgX2 receptor is based on a common structural motif", *Eur. J. Pharmacol.*, 519:191-193 (2005).

Olson et al., "Design and Synthesis of a Protein β-Turn Mimetic", *J. Am. Chem. Soc.*, 112(1):323-333 (1990).

Parham, P., "On the Fragmentation of Monoclonal IgG1, IgG2a, and IgG2b from BALB/c Mice", *J. Immunol.*, 131(6):2895-2902 (1983).

Perretti et al., "Annexin 1: An Endogenous Anti-Inflammatory Protein", *News Physiol. Sci.*, 18:60-64 (2003).

Perretti et al., "Endogenous lipid- and peptide-derived anti-inflammatory pathways generated with glucocorticoid and aspirin treatment activate the lipoxin $A_4$ receptor", *Nat. Med.*, 8(11):1296-1302 (2002).

Phillips et al., "Enhanced antibody response to liposome-associated protein antigens: preferential stimulation of IgG2a/b production", *Vaccine*, 10(3):151-158 (1992).

Pierce et al., "Seven-Transmembrane Receptors", *Nat. Rev.*, 3:639-650 (2002).

Presta, L.G., "Antibody engineering", *Curr. Op. Struct. Biol.*, 2(4):593-596 (1992).

Reudelhuber, T.L., "A Place in Our Hearts for the Lowly Angiotensin 1-7 Peptide?", *Hypertension*, 47:811-815 (2006).

Riechmann et al., "Reshaping human antibodies for therapy", *Nature*, 332(6162):323-329 (1988).

Robas et al., "MrgX2 Is a High Potency Cortistatin Receptor Expressed in Dorsal Root Ganglion", *J. Biol. Chem.*, 278(45):44400-44404 (2003).

Sambanis, A., "Encapsulated islets in diabetes treatment", *Diabetes Technol. Ther.*, 5(4):665-668 (2003).

Santos et al., "Angiotensin-(1-7) and the rennin-angiotensin system", *Curr. Opin. Nephrol. Hypertension*, 16:122-128 (2007).

Santos et al., "Angiotensin-(1-7) is an endogenous ligand for the G protein-coupled receptor Mas", *PNAS*, 100(14):8258-8263 (2003).

Santos et al., "Characterization of a New Selective Antagonist for Angiotensin-(1-7), D-Pro$^7$-Angiotensin-(1-7)", *Hypertension*, 41[part 2]:737-743 (2003).

Santos et al., "Pharmacological Effects of AVE 0991, a Nonpeptide Angiotensin-(1-7) Receptor Agonist", *Cardiovasc. Drug Rev.*, 24(3-4):239-246 (2006).

Santos et al., "The ACE2-Ang-(1-7)-Mas Axis and Cardioprotection", *Curr. Cardiol. Rev.*, 3:57-64 (2007).

Scannell et al., "Lipoxins and Annexin-1: Resolution of Inflammation and Regulation of Phagocytosis of Apoptotic Cells", *Sci. World J.*, 6:1555-1573 (2006).

Schyler et al., "I want a new drug: G-protein-coupled receptors in drug development", *Drug Disc. Today*, 11:481-493 (2006).

Shields et al., "High Resolution Mapping of the Binding Site on Human IgG1 for FcγRI, FcγRII, FcγRIII, and FcRn and Design of IgG1 Variants with Improved Binding to the FcγR", *J. Biol. Chem.*, 276(9):6591-6604 (2001).

Silva et al., "The Therapeutic Potential of Angiotensin-(1-7) as a Novel Renin-Antiotensin System Mediator", *Mini-Rev. Med. Chem.*, 6:603-609 (2006).

Sojar et al., "A Chemical Method for Deglycosylation of Proteins", *Arch. Biochem. Biphys.*, 259(1):52-57 (1987).

Takamatsu et al., "Expression of bacterial chloramphenicol acetyltransferase gene in tobacco plants mediated by TMV-RNA", *EMBO J.*, 6(2):307-311 (1987).

Tamada et al., "The development of polyanhydrides for drug delivery applications", *J. Biomater. Sci. Polymer Edn.*, 3(4):315-353 (1992).

Tatemoto et al., "Immunoglobulin E-independent activiation of mast cell is mediated by Mrg receptors", *Biochem. Biophys. Res. Commun.*, 349:1322-1328 (2006).

Thotakura et al., "Enzymatic Deglycosylation of Glycoproteins", *Meth. Enzymol.*, 138:350-359 (1987).

Toth et al., "A novel oligopeptide delivery system for poorly absorbed peptides and drugs", *ESCOM*, pp. 1078-1079 (1990).

Uludag et al., "Technology of mammalian cell encapsulation", *Adv. Drug Deliv. Rev.*, 42:29-64 (2000).

Unkeless et al., "Structure and Function of Human and Murine Receptors for IgG", *Annu. Rev. Immunol.*, 6:251-281 (1988).

Verhoeyen et al., "Reshaping Human Antibodies: Grafting an Antilysozyme Activity", *Science*, 239:1534-1536 (1988).

Woodle et al., "Liposome Preparation and Size Characterization", *Meth. Enzymol.*, 171:193-217 (1989).

Woodle et al., "Versatility in lipid compositions showing prolonged circulation with sterically stabilized liposomes", *Biochim. Biophys. Acta*, 1105:193-200 (1992).

Zabrocki et al., "Conformational Mimicry. 1. 1,5-Disubstituted Tetrazole Ring as a Surrogate for the Cis Amide Bond", *J. Am. Chem. Soc.*, 110(17):5875-5880 (1988).

Zechel et al., "Synthetic glucagon antagonists and parital agonists", *Int. J. Peptide Protein Res.*, 38:131-138 (1991).

Zhou et al., "Investigation on a novel core-coated microspheres protein delivery system", *J. Control. Release*, 75:27-36 (2001).

Examiner's Report Dated Dec. 22, 2011 From the Australian Government, IP Australia Re. Application No. 2007357448.

International Preliminary Report on Patentability Dated Aug. 27, 2009 From the International Bureau of WIPO Re. Application No. PCT/IB2007/004634.

International Search Report and the Written Opinion Dated Aug. 3, 2009 From the International Searching Authority Re. Application No. PCT/IB2007/004634.

Notice of Allowance Dated Sep. 17, 2010 From the US Patent and Trademark Office Re. U.S. Appl. No. 11/901,975.

Official Action Dated Apr. 7, 2010 From the US Patent and Trademark Office Re. U.S. Appl. No. 11/901,975.

Official Action Dated Oct. 20, 2009 From the US Patent and Trademark Office Re. U.S. Appl. No. 11/901,975.

Restriction Official Action Dated Jul. 9, 2009 From the US Patent and Trademark Office Re. U.S. Appl. No. 11/901,975.

Ahmad et al. "Novel G Protein-Coupled Receptors as Pain Targets", Current Opinion in Investigational Drugs, 5(1): 67-70, 2004.

Allison "The Mode of Action of Immunological Adjuvants", From: Modulation of the ImmuneResponse to Vaccine Antigens, Developments in Biological Standardization, 92: 3-11, 1998.

Anderson et al. "Glutathione Monoethyl Ester: Preparation, Uptake by Tissues, and Conversion to Glutathione", Archives of Biochemistry and Biophysics, 239(2): 538-548, 1985.

Aplin et al. "Preparation, Properties, and Applicaitons of Carbohydrate Conjugates of Proteins and Lipids", CRC Critical Reviews in Biochemistry, 22: 259-306, May 1981.

Bae et al. "Differential Signaling of Formyl Peptide Receptor-Like 1 by Trp-Lys-Tyr-Met-Val-Met-CONH2 or Lipoxin A4 by Human Neutrophils", Molecular Pharmacology, XP002529518, 64(3): 721-730, Sep. 2003.

Bangham et al. "Diffusion of Univalent Ions Across the Lamellae of Swollen Phospholipids", Journal of Molecular Biology, 13: 238-252, 1965.

Bedu-Addo et al. "Interaction of Polyethyleneglycol-Phospholipid Conjugates With Cholesterol-Phosphatidylcholine Mixtures: Sterically Stabilized Liposome Formulations", Pharmaceutical Research, 13(5): 718-724, 1996.

Boerner et al. "Production of Antigen-Specific Human Monoclonal Antibodies From In Vitro-Primed Human Splenocytes", The Journal of Immunology, 147(1): 86-95, Jul. 1, 1991.

Brisson et al. "Expression of a Bacterial Gene in Plants by Using a Viral Vector", Nature, 310: 511-514, 1984.

Broglie et al. "Light-Regulated Expression of a Pea Ribulose-1,5-Biphosphate Carboxylase Small Subunit Gene in Transformed Plant Cells", Science, 224(4651): 838-843, 1984.

Chang et al. "Procedures for Microencapsulation of Enzymes, Cells and Genetically Engineered Microorganisms", Molecular Biotechnology, 17: 249-260, 2001.

Chia et al. "Multi-layered Microcapsules for Cell Encapsulation", Biomaterials, 23: 849-856, 2002.

Chiang et al. "The Lipoxin Receptor ALX: Potent Ligand-Specific and Stereoselective Actions In Vivo", Pharmacological Reviews, 58(3): 463-487, 2006.

Cole et al. "The EBV-Hybridoma Technique and Its Applicaiton to Human Lung Cancer", Monoclonal Antibodies and Cancer Therapy, p. 77-96, 1985.

Coruzzi et al. "Tissue-Specific and Light-Regulated Expression of a Pea Nuclear Gene Encoding the Small Subunit of Ribulose-1,5-Biphosphate Carboxylase", The EMBO Journal, 3(8): 1671-1679, 1984.

De Mello "Angiotensin (1-7) Re-Estabished Impulse Conduction in Cardiac Muscle During Ischaemia-Reperfusion. The Role of the Sodium Pump", Journal of Renin-Angiotensin-Sldosterone System, 5(4): 203-208, Dec. 2004.

DiMaio et al. "Synthesis of Chiral Piperazin-2-Ones as Model Peptidomimetics", Journal of the Chemical Society Perkin Transactions, 9: 1687-1689, 1989.

Dittert et al. "Acetaminophen Prodrugs II. Effect of Structure and Enzyme Source on Enzymatic and Nonenzymatic Hydrolysis of Carbonate Esters", Journal of Pharmaceutical Sciences, 57(5): 780-783, 1968.

Dittert et al. "Carbonate Ester Prodrugs of Salicylic Acid. Synthesis, Solubility, Characteristics, In Vitro Enzymatic Hydrolysis Rates, and Blood Levels of Total Salicylate Following Oral Administration to Dogs", Journal of Pharmaceutical Sciences, 57(5): 828-831, 1968.

Dittert et al. "Hydrolysis of 4-Acetamidophenyl 2,2,2-Trichloroethyl Carbonate by Esterolytic Enxymes From Various Sources", Journal of Pharmaceutical Sciences, 58(5): 557-559, May 1969.

Dong et al. "A Diverse Family of GPCRs Expressed in Specific Subsets of Nociceptive Sensory Neurons", Cell, 106: 619-632, Sep. 7, 2001.

Dray "Novel Molecular Targets in Pain Control", Current Opinion in Anaesthesiology, 16: 521-525, 2003.

Dumas Milne Edwards et al. "Full-Length Human cDNAs Encoding Potentially Secreted Proteins", Database EMBL [Online], XP002529520, Retrieved From EBI, Database Accession No. ABH92391, Aug. 11, 2006. Abstract.

Edge et al. "Deglycosylation of Glycoproteins by Trifluoromethanesulfonic Acid", Analytical Biochemistry, 118: 131-137, 1981.

Ferrario "Role of Angootensin II in Cardiovascular Disease—Therapeutic Implications of More Than a Century of Research", Journal of Renin-Angiotensin-Aldosterone System, 7(1): 3-14, Mar. 2006.

Ferreira et al. "Angiotensin-(1-7) Improves the Post-Ischemic Function in Isolated Perfused Rat Hearts", Brazilian Journal of Medical and Biological Research, 35: 1083-1090, 2002.

Ferreira et al. "Angiotensin-(1-7): Cardioprotective Effect in Myocardial Ischemia/Reperfusion", Hypertension, 38: 665-668, 2001.

Fishwild et al. "High-Avidity Human IgGK Monoclonal Antibodies From a Novel Strain of Minilocus Transgenic Mice", Nature Biotechnology, 14: 845-851, Jul. 1996.

Garvey et al. "3,4-Disubstituted Gamma-Lactam Rings as Conformationally Constrained Mimics of Peptide Derivatives Containing Aspartic Acid of Norleucine", Journal of Organic Chemistry, 55: 936-940, 1990.

Gavins et al. "A Twist in Anti-Inflammation: Annexin 1 Acts Via the Lipoxin A4 Receptor", Prostaglandins, Leukotrienes and Essential Fatty Acids, 73: 211-219, 2005.

Gavins et al. "Formyl-Peptide Receptor Is Not Involved in the Protection Afforded by Annexin 1 in Murine Acute Myocardial Infarct", The FASEB Journal, 19: 100-102, 2005.

Gewirtz "Lipoxin Analogs: Novel Anti-Inflammatory Mediators", Current Opinion in Investigative Drugs, 6(11): 1112-1115, 2005.

Gilchrist "Second Annual GPCRs: From Orphan to Bluckbuster", Expert Opinion in Therapeutic Targets, 8(5): 495-498, 2004.

Gilding "Biodegradable Polymers", In: Biocompatibility of Clinical Implant Materials, Chap.9: 209-232, 1981.

Gonzalez-Rey et al. "Cortistatin as a Potential Multistep Therapeutic Agent for Inflammatory Disorders", Drug News Perspect, 19(7): 393-399, Sep. 2006.

Gurley et al. "Upstream Sequences Required for Efficient Expression of a Soybean Heat Shock Gene", Molecular and Cellular Biology, 6(2): 559-565, Feb. 1986.

Hanes et al. "Polymer Microspheres for Vaccine Delivery", In: Vaccine Design: The Subunit and Adjuvant Approach, Chap.16: 389-412, 1995.

Hoogenboom et al. "By-Passing Immunisation: Human Antibodies From Symthetic Repertoires Germline VH Gene Segments Rearranged In Vitro", Journal of Molecular Biology, 227: 381-388, 1992.

Hopkins et al. "The Druggable Genome", Nature Reviews Drug Discovery, 1: 727-730, Sep. 2002.

Huang "Studies on Phopshatidylcholine Vesicles, Formation and Physical Characteristics", Biochemistry, 8(1): 334-352, 1969.

Jacoby et al. "The 7TM G-Protein-Coupled Receptor Target Family", ChemMedChem, 1: 760-782, 2006.

Jones et al. "Amide Bond Isoteres: Imidazolines in Pseudopeptide Chemistry", Tetrahedron Letters, 29(31): 3853-3856, 1988.

Jones et al. "Replacing the Complementarity-Determining Regions in a Human Antibody With Those a Mouse", Nature, 321(6069): 522-525, 1986.

Kamohara et al. "Identification of MrgX2 as a Human G-Protein-Coupled Receptor for Proadrenomedullin N-Terminal Peptides", Biochemical and Biophysical Research Communications, 330: 1146-1152, 2005.

Kazmierski et al. "Topographic Design of Peptide Neurotransmitters and Hormones on Stable Backbone Templates: Relation of Conformation and Dynamics to Bioactivity", Journal of the American Chemical Society, 113(6): 2275-2283, 1991.

Keidar et al. "ACE2 of the Heart: From Angiotensin I to Angiotensin (1-7)", Cardiovascular Research, 73: 463-469, 2007.

Kemp et al. "(2S, 5S, 8S, 11S)-1-Acetyl-1,4-Diaza-3-Keto-5-Carboxy-10-Thia-Tricyclo-[2.8.0 4,8]-Tridecane, 1 the Preferred Conformation of 1 (1=AlphaTemp-OH) and Its Peptide Conjugates AlphaTemp-L-(Ala)N-Or (N=1 to 4) and Alpha-Temp-L-Ala-L-Phe-L-Lys(EpsilonBoc)-L-Lys(Epsilon-Boc)-NHMe Studies of Templates for Alpha-Helix Fomation", Tetrahedron Letters, 29(39): 4935-4938, 1988.

Kemp et al. "A Convenient Preparation of Derivatives of 3(S)-Amino-10(R)- Carboxy-1,6-Diaza-Cyclodeca-2,7-Dione the Dilactam of L-Alpha,Gamma-Diaminobutyric Acid and D-Glutamic Acid: A Beta-Turn Template", Tetrahedron Letters, 29(40): 5057-5060, 1988.
Kemp et al. "Amino Acid Derivatives That Stabilize Secondary Structures of Polypeptides. 4. Practical Synthesis of 4-(Alkylamino)-3-Cyano-6-Azabicyclo[3.2.1]Oct-3-Enes (Ben Derivatives) as Gamma-Turn Templates", Journal of Organic Chemistry, 54: 109-115, 1989.
Kemp et al. "Conformational Analysis of Peptide-Functionalized Diacyclaminoepinindolidiones 1H NMR Evidence for Beta-Sheet Formation", Tetrahedron Letters, 29(40): 5081-5082, 1988.
Kemp et al. "Conformationally Restricted Cyclic Nonapeptide Derived From L-Cysteine and LL-3-Amino-2-Piperidone-6-Carboxylic Acid (LL-Acp), A Potent Beta-Turn-Inducing Dipeptide Analogue", Journal of Organical Chemistry, 50(26): 5834-5838, 1985.
King et al. "Interaction of Carboypeptidase A With Carbamate and Carbonate Esters", Biochemistry, 26: 2294-2300, 1987.
Kobayashi et al. "Pathophysiological Function of Adrenomedullin and Proadrenomedullin N-Terminal Peptides in Adrenal Chromaffin Cells", Hypertension Research, 26(Suppl.): S71- S78, 2003.
Kucharewicz et al. "Antithrombotic Effect of Captopril and Losartan is Mediated by Angiotensin-(1-7)", Hypertension, 40: 774-779, 2002.
Kunz "Synthesis of Glycopeptides, Partial Structures of Biological Recognition Components", Angewandte Chemie International Edition in English, 26: 294-308, 1987.
La et al. "Annexin 1 Peptides Protect Against Experimental Myocardial Ischemia-Reperfusion: Analysis of Their Mechanism of Action", The FASEB Journal, 15: 2247-2256, 2001.
Lamoyi et al. "Preparation of F(ab')2 Fragments From Mouse IgG of Various Subclasses", Journal of Immunological Methods, 56: 235-243, 1983.
Langer "Biomaterials in Drug Delivery and Tissue Engineering: One Laboratory's Experience", Accounts of Chemical Research, 33(2): 94-101, 2000.
Langer "Selected Advances in Drug Delivery and Tissue Engineering", Journal of Controlled Release, 62: 7-11, 1999.
Larrick et al. "PCR Amplification of Antibody Genes", Methods: A Companion to Methods in Enzymology, 2(2): 106-110, Apr. 1991.
Le et al. "Pleiotropic Roles of Formyl Peptide Receptors", Cytokine and Growth Factor Reviews, 12: 91-105, 2001.
Lee et al. "Differential Production of Leukotriene B4 or Prostaglandin E2 by WKYMVm or Serum Amyloid A Via Formyl Peptide Receptor-Like 1", Biochemical Pharmacology, XP002529519, 72(7): 860-868, Jul. 21, 2006.
Lembo et al. "Proenkephalin A Gene Products Activate a New Family of Sensory Neuron-Specific GPCRs", Nature Neuroscience, 5(3): 201-209, 2002.
Lemos et al. "The Endothelium-Dependent Vasodilator Effect of the Nonpeptide Ang(1-7) Mimic AVE 0991 Is Abolished in the Aorta of Mas-Knockout Mice", Journal of Cardiovascular Pharmacology, 46(3): 274-279, Sep. 3, 2005.
Lindberg et al. "Metabolism of Bambuterol in Rat Liver Microsomes: Identification of Hydroxylated and Demethylated Products by Liquid Chromatography Mass Spectrometry", Drug Metabolism and Disposition, 17(3): 311-322, 1989.
Litzinger et al. "Effect of Liposome Size on the Circulation Time and Intraorgan Distribution of Amphipathic Poly(Ethylene Glycol)-Containing Liposomes", Biochimica et Biophysica Acta, 1190: 99-107, 1994.
Lonberg et al. "Antigen-Specific Human Antibodies From Mice Comprising Four Distinct Genetic Modifications", Nature, 368: 856-859, Apr. 28, 1994.
Lonberg et al. "Human Antibodies From Transgenic Mice", International Reviews of Immunology, 13: 65-93, 1995.
Lu et al. "A Novel Cell Encapsulation Method Using Photosensitive Poly(Allylamine Alpha-Cyanocinnamylideneacetane)", Journal of Microencapsulation, 17(2): 245-251, 2000.
Lu et al. "Cell Encapsulation With Alginate and Alpha-Phenoxycinnamylidene-Acetylated Poly(Allylamine)", Biotechnology and Bioengineering, 70: 479-483, 2000.

Marks et al. "By-Passing Immunization: Building High Affinity Human Antibodies by Chain Shuffling", Bio/Technology, 10(7): 779-783, Jul. 1992.
Marks et al. "By-Passing Immunization: Human Antibodies From V-Gene Libraries Displayed on Phage", Journal of Molecular Biology, 222: 581-597, 1991.
Mathiowitz et al. "Novel Microcapsules for Delivery Systems", Reactive Polymers, 6: 275-283, 1987.
Mathiowitz et al. "Polyanhydride Microspheres as Drug Carriers I. Hot-Melt Microencapsulation", Journal of Controlled Release, 5: 13-22, 1987.
Mathiowitz et al. "Polyanhydride Microspheres as Drug Carriers. II. Microencapsulation by Solvent Removal", Journal of Applied Polymer Science, 35: 755-774, 1988.
Miyake et al. "1,2,3,4-Tetrahydroisoquinoline-3-Carboxylic Acid Angiotensin", Journal of Takeda Research Laboratory, 43(3/4): 53-76, 1984. Abstract in English.
Morrison "Success in Specification", Nature, 368: 812-813, Apr. 28, 1994.
Nagai et al. "Synthesis of a Bicycle Dipeptide With the Shape of Beta-Turn Central Part", Tetrahedron Letters, 26(5): 647-650, 1985.
Neuberger "Generating High-Avidity Human Mabs in Mice", Nature Biotechnology, 14(7): 826, Jul. 1996.
Nothacker et al. "Proadrenomedullin N-Terminal Peptide and Cortison Activation of MrgX2 Receptor Is Based on a Common Structural Motif", European Journal of Pharmacology, 519: 191-193, 2005.
Olson et al. "Design and Synthesis of a Protein Beta-Turn Mimetic", Journal of the American Chemical Society, 112: 323-333, 1990.
Parham "On the Fragmentation of Monoclonal IgG1, IgG2a, and IgG2b From BALB/c Mice", The Journal of Immunology, 131(6): 2895-2902, Dec. 1983.
Perretti et al. "Annexin 1: An Endogenous Anti-Inflammatory Protein", News in Physiological Sciences, 18: 60-64, 2003.
Perretti et al. "Endogenous Lipid- and Peptide-Derived Anti-Inflammatory Pathways Generated With Glucocorticoid and Aspirin Treatment Activate the Lipoxin A4 Receptor", Nature Medicine, 8(11): 1296-1302, Nov. 2002.
Phillips et al. "Enhanced Antibody Response to Liposome-Associated Protein Antigens: Preferential Stimulation of IgG2a/b Production", Vaccine, 10(3): 151-158, 1992.
Pierce et al. "Seven-Transmembrane Receptors", Nature Reviews Molecular Cell Biology, 3: 639-650, 2002.
Presta "Antibody Engineering", Current Opinion in Structural Biology, 2(4): 593-596, 1992.
Reudelhuber "A Place in Our Hearts for the Lowly Angiotensin 1-7 Peptide?", Hypertension, 47: 811-815, 2006.
Riechmann et al. "Reshaping Human Antibodies for Therapy", Nature, 332(6162): 323-329, Mar. 1988.
Robas et al. "MrgX2 Is a High Potency Cortistatin Receptor Expressed in Dorsal Root Ganglion", The Journal of Biological Chemistry, 278(45): 44400-44404, Nov. 7, 2003.
Sambanis "Encapsulated Islets in Diabetes Treatment", Diabetes Technology & Therapeutics, 5(4): 665-668, 2003.
Santos et al. "Angiotensin-(1-7) and the Renin-Angiotensin System", Current Opinion in Nephrology and Hypertension, 16: 122-128, 2007.
Santos et al. "Angiotensin-(1-7) Is an Endogenous Ligand for the G Protein-Coupled Receptor Mas", Proc. Natl. Acad. Sci. USA, PNAS, 100(14): 8258-8263, Jul. 8, 2003.
Santos et al. "Characterization of a New Selective Antagonist for Angiotensin-(1-7), D-Pro7-Angiotensin-(1-7)", Hypertension, 41(Pt.2): 737-743, 2003.
Santos et al. "The ACE2-Ang-(1-7)-Mas Axis and Cardioprotection", Current Cardiology Reviews, 3: 57-64, 2007.
Santos et al. Pharmacological Effects of AVE 0991, A Nonpeptide Angiotensin-(1-7) Receptor Agonist, Cardiovascular Drug Review, 24(3-4): 239-246, 2006.
Scannell et al. "Lipoxins and Annexin-1: Resolution of Inflammation and Regulation of Phagocytosis of Apoptotic Cells", TheScientificWorldJournal, 6: 1555-1573, 2006.

Schlyer et al. "I Want a New Drug: G-Protein-Coupled Receptor in Drug Development", Drug Discovery Today, 11(11/12): 481-493, Jun. 2006.

Shemesh et al. "Discovery and Validation of Novel Peptide Agonists for G-Protein-Coupled Receptors", The Journal of Biological Chemistry, XP0025524602, 283(50): 34643-34649, Dec. 12, 2008.

Shields et al. "High Resolution Mapping of the Binding Site on Human IgG1 for FcGammaRI, FcGammaRII, FcGammaRIII, and FcRn and Design of IgG1 Variants With Improved Binding to the FcGammaR", The Journal of Biological Chemistry, 276(9): 6591-6604, Mar. 2, 2001.

Simoes e Silva et al. "The Therapeutic Potential of Angiotensin-(1-7) as a Novel Renin-Angiotensin System Mediator", Mini-Reviews in Medicinal Chemistry, 6: 603-609, 2006.

Singhal et al. "Glutathione, a First Line of Defense Against Cadmium Toxicity", The FASEB Journal, 1: 220-223, 1987.

Sojar et al. "A Chemical Method for the Deglycosylation of Proteins", Archives of Biochemistry and Biophysics, 259(1): 52-57, 1987.

Takamatsu et al. "Expression of Bacterial Chloramphenicol Acetyltransferase Gene in Tobacco Plants Mediated by TMV-RNA", The EMBO Journal, 6(2): 307-311, 1987.

Tamada et al. "The Development of Polyanhydrides for Drug Delivery Applications", Journal of Biomaterials Science, Polymer Edition, 3(4): 315-353, 1992.

Tatemoto et al. "Immunoglobulin E-Independent Activation of Mast Cell Is Mediated by Mrg Receptors", Biochemical and Biophysical Research Communications, 349: 1322-1328, 2006.

Thotakura et al. "Enzymatic Deglycosylation of Glycoproteins", Methods in Enzymology, 138(Chap.28): 350-359, 1987.

Toth et al. "A Novel Oligopeptide Delivery System for Poorly Absorbed Peptides and Drugs", ESCOM, p. 1078-1079, 1990.

Tunek et al. "Hydrolysis of 3H-Bambuterol, A Carbamate Prodrug of Tebutaline, in Blood From Humans and Laboratory Animals In Vitro", Biochemical Pharmacology, 37(20): 3867-3876, 1988.

Uludag et al. "Technology of Mammalian Cell Encapsulation", Advanced Drug Delivery Reviews, 42: 29-64, 2000.

Unkeless et al. "Structure and Function of Human and Murine Receptors for IgG", Annual Reviews in Immunology, 6: 251-281, 1988.

Verhoeyen et al. "Reshaping Human Antibodies: Grafting an Antilysozyme Activity", Science, 239: 1534-1536, 1988.

Woodle et al. "Liposome Preparation and Size Characterization", Methods in Enzymology, 171(Chap.9): 193-217, 1989.

Woodle et al. "Versatility in Lipid Compositions Showing Prolonged Circulation With Sterically Stabilized Liposomes", Biochimica et Biophysica Acta, 1105: 193-200, 1992.

Zabrocki et al. "Conformational Mimicry. !. 1,5-Disubstituted Tetrazole Ring as a Surrogate for the Cis Amide Bond", Journal of the American Chemical Society, 110(17): 5875-5880, 1988.

Zechel et al. "Synthetic Glucagon Antagonists and Partial Agonists", International Journal of Peptide and Protein Research, 38(2): 131-138, Aug. 1991.

Zhou et al. "Investigation on a Novel Core-Coated Microspheres Protein Delivery System", Journal of Controlled Release, 75: 27-36, 2001.

Office Action Dated Feb. 1, 2012 From the Israel Patent Office Re. Application No. 197115 and Its Translation Into English.

Communication Pursuant to Article 94(3) EPC Dated Dec. 4, 2009 From the European Patent Office Re. Application No. 07875175.7.

Communication Pursuant to Article 94(3) EPC Dated Sep. 10, 2010 From the European Patent Office Re. Application No. 07875175.7.

Communication Pursuant to Article 94(3) EPC Dated Apr. 12, 2010 From the European Patent Office Re. Application No. 07875175.7.

Communication Under Rule 71(3) EPC Dated Mar. 24, 2011 From the European Patent Office Re. Application No. 07875175.7.

Decision to Grant a European Patent Pursuant to Article 97(1) EPC Dated Oct. 7, 2011 From the European Patent Office Re. Application No. 07875175.7.

European Search Report and the European Search Opinion Dated Jul. 27, 2012 From the European Patent Office Re. Application No. 11171843.3.

English Summary of Notice of Rejection Dated Oct. 9, 2012 From the Japanese Patent Office Re. Application No. 2009-527929.

Office Action Dated Oct. 17, 2012 From the Israel Patent Office Re. Application No. 197115 and Its Translation Into English.

Shimomura et al. "Identification of Neuropeptide W as the Endogenous Ligand for Orphan G-Protein-Coupled Receptors GPR7 and GPR8", The Journal of Biological Chemistry, 277(39): 35826-35832, Sep. 27, 2002.

* cited by examiner

FIG. 1

| Name | Sequence | SEQ ID |
|---|---|---|
| P58* | TIPMFVPESTSKLQKFTSWFM | SEQ ID 1 |
| P58_4* | FTSWFM | SEQ ID 2 |
| P58_5* | LQKFTSWFM | SEQ ID 3 |
| P58_10* | TIPMFVPESTSTLQKFTSWFM | SEQ ID 4 |
| P94 | AAQATGPLQDNELPGLDERPPRAHAQH FHKHQLWPSPFRALKPRP | SEQ ID 5 |
| P33 monomer and dimer | SMCHRWSRAVLFPAAHRP | SEQ ID 6 |
| P33_V | SMVHRWSRAVLFPAAHRP | SEQ ID 7 |
| P60_S | GIGSVWHWKHRVATRFTLPRFLQ | SEQ ID 8 |
| P_61 monomer and dimer | FLGYCIYLNRKRRGDPAFKRRLRD | SEQ ID 9 |
| P_61_S | FLGYSIYLNRKRRGDPAFKRRLRD | SEQ ID 10 |
| P61_4 | IYLNRKRRGDPAFKRRLRD | SEQ ID 11 |
| P61_11S | FAFLGYSIYLNRKRRGDPAF | SEQ ID 12 |
| P61_11 monomer and dimer | FAFLGYCIYLNRKRRGDPAF | SEQ ID 13 |
| P33_8 | RWSRAVLFPAAHRP | SEQ ID 14 |
| P33_9 | HRWSRAVLFPAAHRP | SEQ ID 15 |
| P33_10 | WSRAVLFPAAHRP | SEQ ID 16 |
| P63 | AHAQHFHKHQLWPSPFRALKPRP | SEQ ID 17 |
| P61_5S | FAFLGYSIYLN | SEQ ID 18 |
| P61_5 monomer and dimer | FAFLGYCIYLN | SEQ ID 19 |
| P61 derivative | FAFLGYCIYLNRKRRGDPAFKRRLRD | SEQ ID 20 |
| P61 derivative | FLGYCIYLN | SEQ ID 21 |
| P61 derivative | FLGYCIYLNR | SEQ ID 22 |
| P61 derivative | FLGYCIYLNRKRRGDPAF | SEQ ID 23 |
| P61 derivative | RGDPAF | SEQ ID 24 |
| P61 derivative | RRGDPAF | SEQ ID 25 |
| P58 derivative | HKRTIPMFVPESTSKLQKFTSWFM | SEQ ID 26 |
| P33_5 | AVLFPAAHRP | SEQ ID 27 |
| P61_14 | GDPAFKRRLRD | SEQ ID 28 |
| P61_16 | GDPAF | SEQ ID 29 |
| P61_7 | IYLN | SEQ ID 30 |
| P61_13 | IYLNRKRRGDPAF | SEQ ID 31 |
| P94/63_27 | AAQATGPLQDNELPGLDERPP | SEQ ID 32 |
| P94/63_26 | AAQATGPLQDNELPGLDERPPRAHAQHFH | SEQ ID 33 |
| P94/63_21 | PPRAHAQHFHKHQLWPSPFRALKPRP | SEQ ID 34 |
| P94/63_9 | HQLWPSPFRALKPRP | SEQ ID 35 |
| P58_7 | TIPMFVPESTSKLQ | SEQ ID 36 |
| P58_12 | TIPMFVPESTSTLQ | SEQ ID 37 |
| P58_6 | TIPMFVPESTS | SEQ ID 38 |
| P60 | GIGCVWHWKHRVATRFTLPRFLQ | SEQ ID 39 |
| P60 derivative | GIGCVWHWKHRVATRFTLPRFLQRR | SEQ ID 40 |
| P60 derivative | GIGCVWHWKHRVATRFTLPRFLQRRSS | SEQ ID 41 |
| P60 derivative | GIGCVWHWKHRVATRFTLPRFLQRRSSR | SEQ ID 42 |
| P60 derivative | IGCVWHWKHRVATRFTLPRFLQ | SEQ ID 43 |
| P60 derivative | IGCVWHWKHRVATRFTLPRFLQRR | SEQ ID 44 |
| P60 derivative | IGCVWHWKHRVATRFTLPRFLQRRSS | SEQ ID 45 |
| P60 derivative | IGCVWHWKHRVATRFTLPRFLQRRSSR | SEQ ID 46 |
| P60 derivative | CVWHWKHRVATRFTLPRFLQ | SEQ ID 47 |
| P60 derivative | CVWHWKHRVATRFTLPRFLQRR | SEQ ID 48 |
| P60 derivative | CVWHWKHRVATRFTLPRFLQRRSS | SEQ ID 49 |
| P60 derivative | CVWHWKHRVATRFTLPRFLQRRSSR | SEQ ID 50 |

*The peptides marked with an asterisk, were synthesized with an amide at their C-terminus, for the experiments described in this application Effect of P58 and Ac2-26 on zymosan-induced leukocyte influx as evaluated at the end of the study (4 h time-point).

| Treatment | Mean ± SEM | % Control | % Inhibition |
|---|---|---|---|
| Vehicle | 38.3 ± 5.5 | 100 | 0 |
| Peptide P58 (50 µg i.v.) | 24.0 ± 4.9 | 62 | 38 |
| Peptide P58 (200 µg i.v.) | 28.5 ± 5.0 | 74 | 26 |
| Peptide Ac2-26 (200µg i.v.) | 19.8 ± 4.8 * | 51 | 49 |
| Peptide P58 (100 µg in situ) | 2.8 ± 0.5 | na | na |
| Vehicle (in situ) | 2.4 ± 0.4 | na | na |

Values for total leukocytes are $10^5$ per 2ml of lavage fluid from one mouse.
* $P < 0.05$ vs. vehicle. na = not applicable.

FIG. 23

Effect of P58 and Ac2-26 on zymosan induced neutrophil (GR-1$^+$) influx as evaluated at the end of the study (4 h time-point).

| Treatment | Mean ± SEM | % Control | % Inhibition |
|---|---|---|---|
| Vehicle | 33.3 ± 4.3 | 100 | 0 |
| Peptide P58 (50 µg i.v.) | 20.0 ± 3.7 * | 60 | 40 |
| Peptide P58 (200 µg i.v.) | 23.9 ± 4.0 | 71 | 29 |
| Peptide Ac2-26 (200µg i.v.) | 16.2 ± 3.0 * | 48 | 52 |
| Peptide P58 (100 µg in situ) | 0.39 ± 0.08 | na | na |
| Vehicle (in situ) | 0.37 ± 0.16 | na | na |

Values for GR-1$^+$ cells numbers are $10^5$ per 2ml of lavage fluid from one mouse.
* $P < 0.05$ vs. vehicle. na = not applicable.

FIG. 24

Effect of P58 and analogs on zymosan induced leukocyte influx as evaluated at the end of the study (4 h time-point; cumulative data).

| Treatment | Mean ± SEM | % Control | % Inhibition |
|---|---|---|---|
| Vehicle | 60.0 ± 6.8 | 100 | na |
| Peptide P58 (20nmol i.v.) | 31.7 ± 4.9* | 53 | 47 |
| Peptide P58 (80nmol i.v.) | 40.3 ± 6.8 | 67 | 33 |
| Peptide P58-4 (20nmol i.v.) | 39.1 ± 5.1* | 65 | 35 |
| Peptide P58-4 (80nmol i.v.) | 31.7 ± 5.0* | 53 | 47 |
| Peptide P58-5 (20nmol i.v.) | 60.5 ± 10.8 | 101 | −1 |
| Peptide P58-5 (80nmol i.v.) | 42.5 ± 5.12 | 71 | 29 |

Values for total leukocytes are $10^5$ per 2ml of lavage fluid from one mouse.
* $P < 0.05$ vs. vehicle. na = not applicable.

FIG. 26

Effect of P58 and analogs on zymosan induced neutrophil (GR-1+) influx as evaluated at the end of the study (4 h time-point; cumulative data).

| Treatment | Mean ± SEM | % Control | % Inhibition |
|---|---|---|---|
| Vehicle | 50.9 ± 5.6 | 100 | na |
| Peptide P58 (20nmol i.v.) | 25.6 ± 3.8* | 50 | 50 |
| Peptide P58 (80nmol i.v.) | 36.3 ± 6.3 | 71 | 29 |
| Peptide P58-4 (20nmol i.v.) | 33.0 ± 4.0* | 65 | 35 |
| Peptide P58-4 (80nmol i.v.) | 26.1 ± 3.8* | 51 | 49 |
| Peptide P58-5 (20nmol i.v.) | 53.1 ± 9.4 | 104 | -4 |
| Peptide P58-5 (80nmol i.v.) | 36.0 ± 4.1 | 71 | 29 |

Values for GR-1$^+$ cells numbers are $10^5$ per 2ml of lavage fluid from one mouse.
* $P<0.05$ vs. vehicle. na = not applicable.

FIG. 27

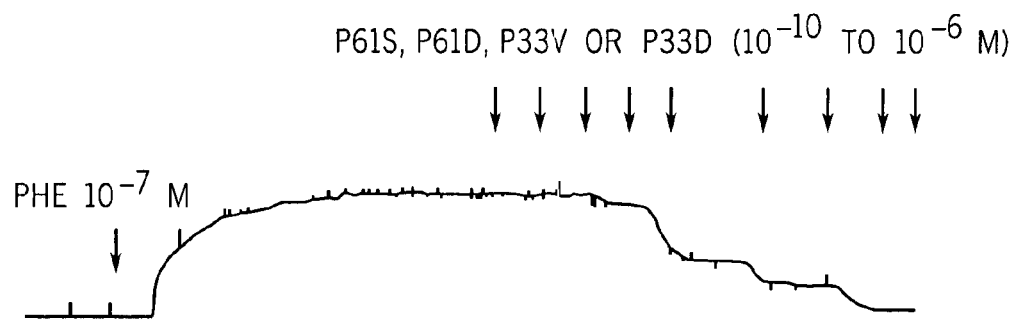

FIG. 28

PEPTIDE LIGANDS FOR G-PROTEIN COUPLED RECEPTORS

RELATED APPLICATIONS

This application claims priority to U.S. Ser. No. 60/845,606, filed Sep. 18, 2006; U.S. Ser. No. 60/846,421, filed Sep. 21, 2006; and U.S. Ser. No. 60/851,591, filed Oct. 12, 2006. The contents of all of these applications are incorporated herein by reference in their entireties.

FIELD OF THE INVENTION

The invention relates to bioactive peptides.

BACKGROUND OF THE INVENTION

Known and uncharacterized GPCRs (G-protein coupled receptors) currently constitute major targets for drug action and development, and >30% of all marketed therapeutics act on them (Jacoby et al 2006, ChemMedChem 1, 760-782). GPCRs usually have seven transmembrane domains. Upon binding of a ligand to an extra-cellular portion or fragment of a GPCR, a signal is transduced within the cell that results in a change in a biological or physiological property or behavior of the cell. GPCRs, along with G-proteins and effectors (intracellular enzymes and channels modulated by G-proteins), are the components of a modular signaling system that connects the state of intra-cellular second messengers to extra-cellular inputs (Pierce et al 2002, Nature Reviews Molecular Cell Biology 3, 639-650). The GPCRs seem to be of critical importance to both the central nervous system and peripheral physiological processes.

The GPCR superfamily is diverse and sequencing of the human genome has revealed >850 genes that encode them (Hopkins and Groom 2002, Nature Reviews Drug Discovery 1, 727-730). There is great diversity within the GPCRs, which is matched by a great variety of ligands that activate them. Known drugs target only ~30 members of the GPCR family, mainly biogenic amine receptors. Thus, there is an enormous potential within the pharmaceutical industry to exploit the remaining family members, including the >100 orphan receptors for which no existing ligands have so far been identified (Gilchrist 2004, Expert Opin. Ther. Targets 8, 495-498).

There are ongoing efforts to identify new GPCRs and to deorphanize known GPCRs, which can be used to screen for new agonists and antagonists having potential prophylactic and therapeutical properties (Gilchrist 2004, Expert Opin. Ther. Targets 8, 495-498; Schyler and Horuk 2006, Drug Discovery Today 11, 481-493). Below are examples of GPCRs pertinent to this application, which may serve as targets for novel therapeutic agents.

The Mas receptor is the product of the MAS1 proto-oncogene, which was first isolated based on its tumorigenic activity and later identified as a member of the rhodopsin-like class A GPCR subfamily. It was recently demonstrated that Ang (1-7) is an agonist of Mas and that this peptide is formed by the action of ACE2 (angiotensin converting enzyme 2) on angiotensin I (reviewed in Santos et al. 2007, Current Cardiology Reviews 3, 57-64). While the chronic increase in AngII can induce many deleterious effects on the heart, Ang(1-7) has cardioprotective actions, including vasodilation and antiproliferative activities, which often oppose those of AngII. The effects of Ang(1-7) are associated with lowering blood pressure, prevention of cardiac remodeling and attenuation of renal abnormalities associated with hypertension (Reudelhuber 2006, Hypertension 47, 811-815).

Mas, ACE2 and Ang(1-7) are considered important components of the renin-angiotensin system (RAS), which is a major regulator of cardiovascular homeostasis and hydroelectrolyte balance (Silva et al 2006, Mini-reviews in Medicinal Chemistry 6, 603-609; Santos and Ferreira 2007, Current Opinion in Nephrology and Hypertension 16, 122-128). Disturbances in the RAS system play a pivotal role in the pathogenesis of hypertension and cardiovascular diseases. RAS can be viewed as a system comprising two main axes with opposite actions: the vasoconstrictor/proliferative ACE-AngII-AT1/AT2 axis, and the vasodilator/anti-proliferative ACE2-Ang(1-7)-Mas axis.

Components of the ACE-AngII-AT1/AT2 axis serve as targets for two major types of drugs, the ACE inhibitors (ACEi) and the AT1 receptor blockers (ARBs), which are successful therapeutic strategies against several clinical conditions, including arterial hypertension, left ventricular systolic dysfunction, chronic heart failure, myocardial infarction and diabetic and non-diabetic chronic kidney diseases (Ferrario 2006, Journal of the Renin-Angiotensin-Aldosterone System 7, 3-14). The ACE2-Ang(1-7)-Mas axis is considered as a putatively important target for the development of new drugs to treat cardiovascular and renal diseases (Santos et al. 2007, Current Cardiology Reviews 3, 57-64; Keidar et al 2007, Cardiovascular Research 73, 463-469). The potential therapeutic application of the Mas receptor is indeed supported by the cardioprotective and beneficial effects of its peptide agonist, Ang(1-7), and an orally active nonpeptide agonist, AVE 0991, in several experimental models (Santos and Ferreira 2006, Cardiovascular Drug Reviews 24, 239-246).

The FPRL1 receptor belongs to the FPR (formyl-peptide receptor) related family of GPCRs that also includes FPR and FPRL2 (Le et al 2001, Cytokine and Growth Factor Reviews 12, 91-105). This receptor, also known as the lipoxin $A_4$ receptor, ALXR, binds pleiotropic ligands, i.e. both lipids and peptides, and is expressed primarily by neutrophils, eosinophils and monocytes (Chiang et al 2006, Pharmacological Reviews 58, 463-487). The two prominent types of endogenous FPRL1 ligands, lipoxin $A_4$ (LXA4) and the aspirin-triggered lipoxins (ATLs), and the AnnexinI protein and its N-terminal derived peptides, have shown anti-inflammatory properties in various experimental animal models (Gavins et al 2005, Prostaglandins, Leukotrienes and Essential Fatty Acids 73, 211-219).

Extensive research has clarified that the mechanism underlying the anti-inflammatory activity gained upon FPRL1 activation by these ligands is achieved by promoting resolution of inflammation—an active and tightly synchronized process, involving counter-regulation of leukocytes (Scannell and Maderna 2006, The Scientific World Journal 6, 1555-1573). Activation of FPRL1 evokes inhibition of polymorphonuclear neutrophils (PMN's) and eosinophils migration and prevents leukocyte-mediated tissue injury. In addition, emigration of monocytes is stimulated upon FPRL1 activation, enabling the clearance of apoptotic cells from the inflammatory site in a nonphlogistic manner. Furthermore, NK cytotoxicity is inhibited which further contributes to downregulation of proinflammatory mediators at the site of inflammation.

Both LXA4 (and its stable analog ATLa) and Ac2-26 (a peptide derived from the N-terminus of AnnexinI) have been extensively studied in various animal disease models of acute and chronic inflammation, such as dermal inflammation, colitis, asthma, and ischemia/reperfusion injury, and were found to be efficacious (Perretti and Gavins 2003, News Physiol. Sci. 18, 60-64; Gewirtz 2005, Current Opinion in Investigational Drugs 6, 1112-1115). These findings indicate that FPRL1 agonists open new avenues and approaches to therapeutic interventions via accelerated resolution of inflammation, and might have a beneficial therapeutic value in various pathological inflammatory conditions, such as ischemia/reperfusion injury, organ transplantation, inflammatory bowel disease, psoriasis, asthma, and arthritis. A stable lipoxin analog is indeed in clinical development for inflammatory bowel disease (Berlex).

The MrgX1 (Mas-related gene X1) receptor, also named SNSR4 (sensory neuron specific receptor 4), has been detected only in the nociceptive sensory neurons of the dorsal root ganglia (Dong et al 2001, Cell 106, 619-632). It is preferentially activated by opioid-related peptides, such as the proenkephalin A-derived peptide, BAM22 (Lembo et al 2002, Nature Neurosci. 5, 201-209). MrgX2 is another member of the Mrg family of GPCRs, which also shows high expression in nociceptive neurons, but also in various other tissues. Various high and low affinity ligands have been identified for MrgX2 (Robas et al 2003, J. Biol. Chem. 278, 44400-44404). The physiological role that these receptors play in vivo is not clear.

Based on their expression in nociceptors, which are neurons that mediate nociceptive transmission of pain, Mrg receptors are believed to play a role in the sensation or modulation of acute pain as well as chronic pain associated with nerve injury or inflammation. The Mrg family, and in particular MrgX1, are thus viewed as promising pharmacological targets for the management of pain (Ahmad and Dray 2004; Current Opinion in Investigational Drugs 5, 67-70; Dray 2003, Current Opinion in Anaesthesiology 16, 521-525).

MrgX2 is also activated by several secretagogues, and seems to participate in the activation of human mast cells by such substances Tatemoto et al 2006, Biochem. Biophys. Res. Comm 349, 1322-1328). As such, MrgX2 might provide a novel therapeutic target for the control of diseases involving mast cell activation. CST, a high affinity ligand of MrgX2, is a neuropeptide involved in sleep regulation and locomotor activity (Robas et al 2003, J. Biol. Chem. 278, 44400-44404). CST also emerged as a potential endogenous immune modulator, and has recently shown potent anti-inflammatory activity in experimental animal models (Gonzalez-Rey and Delgado 2006, Drug News Perspect 19, 393-399). MrgX2 may thus also be involved in sleep regulation, and in inflammation.

Another high affinity ligand of MrgX2 is PAMP-12 (Kamohara et al 2005, Biochem. Biophys. Res. Comm 330, 1146-1152; Nothacker et al 2005, Eur. J. Pharmacol. 519, 191-193), which derives from proadrenomedullin and like other PAMP peptides has vasophysiological functions that appear to relate to several diseases, such as hypertension, chronic renal failure and congestive heart failure and chronic glomerulonephritis (Kobayashi et al 2003, Hypertension Research 26, S71-S78). Based on this, MrgX2 may also be a target of potential hypotension-regulating drugs.

SUMMARY OF THE INVENTION

The invention is based in part on the identification of novel peptides: Peptide 33-type peptides, Peptide 58-type peptides, Peptide 60-type peptides, Peptide 61-type peptides, Peptide 63-type peptides, and Peptide 94-type peptides, that act as ligands of four known GPCR receptors, but do not show significant homology to known GPCR ligands.

Two peptides, exemplified by Peptide 61_S and Peptide 33_V and compounds of Formulas I and II, respectively, activate the MAS1 gene product, i.e. the Mas receptor. This receptor is an important component of the renin angiotensin system, which is a major regulator of cardiovascular homeostasis and hydroelectrolyte balance. This receptor is viewed as a putatively important target for the development of new drugs to treat cardiovascular and renal diseases. As is explained below, peptides represented by Peptide 61_S and 33_V act as agonists of the Mas receptor, and elicit calcium flux in Mas-expressing cells. Furthermore, these peptides induce relaxation of rat aortic rings and reduced heart hypertrophy induced by Isoproterenol. Thus, peptides represented by Peptide 61_S and 33_V, as well as compounds within Formulas I and II, are useful as agonists in conditions benefiting from increasing the activity of the Mas receptor, such as hypertension, heart failure and other cardiovascular pathological conditions.

The peptide exemplified by Peptide 60_S falls within a compound of Formula III and activates the MRGPRX1 gene product, i.e the MrgX1 receptor (Mas-related G-protein coupled receptor member X1, also known as SNSR4). This receptor is believed to be involved in the function of nociceptive neurons and to regulate nociceptor function and/or development, including the sensation or modulation of pain. It is potently activated by enkephalins-derived peptides, such as BAM22 (bovine adrenal medulla peptide 22). Peptide 60_S is superior to BAM22 in eliciting calcium flux in MrgX1 expressing cells. Thus, as is explained below, peptides represented by Peptide 60_S, as well as compounds within Formula III, are useful as agonists in conditions benefiting from increasing the activity of MrgX1.

Peptides exemplified by Peptide 61_S, Peptide 60_S, Peptide 94, and Peptide 63, and compounds of Formulas I, III, IV, and V, respectively, activate the MRGPRX2 gene product, MrgX2 (Mas-related G-protein coupled receptor member X2). This receptor is believed to be involved in the function of nociceptive neurons and to regulate nociceptor function and/ or development, including the sensation or modulation of pain. Cortistatin-14 (CST) is a high potency ligand of this receptor. Cortistatin has several biological functions, including roles in sleep regulation, locomotor activity, and cortical function. Peptide 60_S, Peptide 61_S, Peptide 63, and Peptide 94 are superior to cortistatin-14 in eliciting calcium flux in MrgX2-expressing cells. Thus, as explained below, peptides represented by Peptide 61_S, Peptide 60_S, Peptide 94, and Peptide 63, as well as compounds within Formulas I, III, IV, and V, respectively, are useful as agonists in conditions benefiting from increasing the activity of MrgX2.

Peptides exemplified by Peptide 33_V, Peptide 60_S, Peptide 94, and Peptide 58, and compounds of Formulas II, III, IV, and VI, respectively, activate FPRL1 (FPR-related receptor 1) (also known as lipoxin $A_4$ receptor, LXA4R or ALXR). The activation of FPRL1 by lipoxins or annexinI-derived peptides results in anti-inflammatory effects. Peptide 33_V, Peptide 60_S, Peptide 94, and Peptide 58 induce calcium flux in FPRL-1 expressing cells. Furthermore, Peptide 58 and peptides derived from it, exhibit anti-inflammatory activity in a mouse model of acute inflammation. Thus, as explained below, peptides represented by Peptide 33_V, Peptide 60_S, Peptide 94, and Peptide 58, as well as compounds within Formulas II, III, IV, and VI, are useful as agonists in conditions benefiting from increasing the activity of a FPRL1, such as acute and chronic inflammation.

In addition the invention includes the following additional embodiments.

The invention in one embodiment includes a peptide less than 100 amino acids in length, said polypeptide comprising the amino acid sequence of Formula I, Formula II, Formula III, Formula IV, Formula V, or Formula VI, wherein Formula I is $A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$, or a pharmaceutically acceptable salt thereof; wherein
$A^1$ is absent or F or a hydrophobic non-naturally occurring amino acid;
$A^2$ is absent or A or a small non-naturally occurring amino acid;
$A^3$ is absent or F or a hydrophobic non-naturally occurring amino acid;
$A^4$ is absent or L or a hydrophobic non-naturally occurring amino acid;
$A^5$ is absent or G or a small non-naturally occurring amino acid;
$A^6$ is absent or Y or a hydrophobic non-naturally occurring amino acid;
$A^7$ is absent or S or C;
$A^8$ is absent or I or a hydrophobic non-naturally occurring amino acid;
$A^9$ is absent or Y or a hydrophobic non-naturally occurring amino acid;
$A^{10}$ is absent or L or a hydrophobic non-naturally occurring amino acid;
$A^{11}$ is absent or N or a polar non-naturally occurring amino acid;
$A^{12}$ is absent or R or a basic non-naturally occurring amino acid;
$A^{13}$ is absent or K or a basic non-naturally occurring amino acid;
$A^{14}$ is absent or R or a basic non-naturally occurring amino acid;
$A^{15}$ is absent or R or a basic non-naturally occurring amino acid;
$A^{16}$ is absent or G, or a small non-naturally occurring amino acid;
$A^{17}$ is absent or D or a polar non-naturally occurring amino acid;
$A^{18}$ is absent or P;
$A^{19}$ is absent or A or a hydrophobic non-naturally occurring amino acid;
$A^{20}$ is absent or F or a hydrophobic non-naturally occurring amino acid;
$A^{21}$ is absent or K or a basic non-naturally occurring amino acid;
$A^{22}$ is absent or R or a basic non-naturally occurring amino acid;
$A^{23}$ is absent or R or a basic non-naturally occurring amino acid;
$A^{24}$ is absent or L or a hydrophobic non-naturally occurring amino acid;
$A^{25}$ is absent or R or a hydrophobic non-naturally occurring amino acid;
$A^{26}$ is absent or D or a polar non-naturally occurring amino acid;
wherein Formula II is $B^1$-$B^2$-$B^3$-$B^4$-$B^5$-$B^6$-$B^7$-$B^8$-$B^9$-$B^{10}$-$B^{11}$-$B^{12}$-$B^{13}$-$B^{14}$-$B^{15}$-$B^{16}$-$B^{17}$-$B^{18}$, or a pharmaceutically acceptable salt thereof;
wherein
$B^1$ is absent or S;
$B^2$ is absent or M or norleucine (Nle) or another hydrophobic non-naturally occurring amino acid;
$B^3$ is absent or C or V;
$B^4$ is absent or H or a basic non-naturally occurring amino acid;
$B^5$ is absent or R or a basic non-naturally occurring amino acid;
$B^6$ is absent or W or a hydrophobic non-naturally occurring amino acid
$B^7$ is absent or S;
$B^8$ is absent or R or a hydrophobic non-naturally occurring amino acid;
$B^9$ is A or a small non-naturally occurring amino acid;
$B^{10}$ is V or a hydrophobic non-naturally occurring amino acid;
$B^{11}$ is L or a hydrophobic non-naturally occurring amino acid;
$B^{12}$ is F or a hydrophobic non-naturally occurring amino acid;
$B^{13}$ is P;
$B^{14}$ is A or a hydrophobic non-naturally occurring amino acid;
$B^{15}$ is A or a hydrophobic non-naturally occurring amino acid;
$B^{16}$ is H or a basic non-naturally occurring amino acid;
$B^{17}$ is R or a basic non-naturally occurring amino acid;
$B^{18}$ is P;
wherein Formula III is $C^1$-$C^2$-$C^3$-$C^4$-$C^5$-$C^6$-$C^7$-$C^8$-$C^9$-$C^{10}$-$C^{11}$-$C^{12}$-$C^{13}$-$C^{14}$-$C^{15}$-$C^{16}$-$C^{17}$-$C^{18}$-$C^{19}$-$C^{20}$-$C^{21}$-$C^{22}$-$C^{23}$-$C^{24}$-$C^{25}$-$C^{26}$-$C^{27}$-$C^{28}$, or a pharmaceutically acceptable salt thereof;
$C^1$ is absent or G or a small non-naturally occurring amino acid;
$C^2$ is absent or I or a hydrophobic non-naturally occurring amino acid;
$C^3$ is absent or G or a small non-naturally occurring amino acid;
$C^4$ is C or S or a polar non-naturally occurring amino acid;
$C^5$ is V or a hydrophobic non-naturally occurring amino acid;
$C^6$ is W or a hydrophobic non-naturally occurring amino acid
$C^7$ is H or a basic non-naturally occurring amino acid;
$C^8$ is W or a hydrophobic non-naturally occurring amino acid;
$C^9$ is K or a basic non-naturally occurring amino acid;
$C^{10}$ is H or a basic non-naturally occurring amino acid;
$C^{11}$ is R or a basic non-naturally occurring amino acid;
$C^{12}$ is V or a hydrophobic non-naturally occurring amino acid;
$C^{13}$ is A or a hydrophobic non-naturally occurring amino acid;
$C^{14}$ is T or a polar non-naturally occurring amino acid;
$C^{15}$ is R or a basic non-naturally occurring amino acid;
$C^{16}$ is F or a hydrophobic non-naturally occurring amino acid;
$C^{17}$ is T or a polar non-naturally occurring amino acid;
$C^{18}$ is L or a hydrophobic non-naturally occurring amino acid;
$C^{19}$ is P;
$C^{20}$ is R or basic non-naturally occurring amino acid;
$C^{21}$ is F or a polar non-naturally occurring amino acid;
$C^{22}$ is L or a hydrophobic non-naturally occurring amino acid;
$C^{23}$ is Q or a polar non-naturally occurring amino acid.
$C^{24}$ is absent or R or a basic non-naturally occurring amino acid;
$C^{25}$ is absent or R or a basic non-naturally occurring amino acid;

$C^{26}$ is absent or S or a polar non-naturally occurring amino acid;
$C^{27}$ is absent or S or a polar non-naturally occurring amino acid; or
$C^{28}$ is absent or R or a basic non-naturally occurring amino acid;
wherein Formula IV is

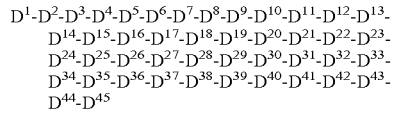

or a pharmaceutically acceptable salt thereof, wherein
$D^1$ is A or a small non-naturally occurring amino acid;
$D^2$ is A or a small non-naturally occurring amino acid;
$D^3$ is Q or a polar non-naturally occurring amino acid;
$D^4$ is A or a hydrophobic non-naturally occurring amino acid;
$D^5$ is T or a polar non-naturally occurring amino acid;
$D^6$ is G or a small non-naturally occurring amino acid;
$D^7$ is P;
$D^8$ is L or a hydrophobic non-naturally occurring amino acid;
$D^9$ is Q or a polar non-naturally occurring amino acid;
$D^{10}$ is D or a polar non-naturally occurring amino acid;
$D^{11}$ is N or a polar non-naturally occurring amino acid;
$D^{12}$ is E or a non-naturally occurring amino acid;
$D^{13}$ is L or a hydrophobic non-naturally occurring amino acid;
$D^{14}$ is P;
$D^{15}$ is G or a small non-naturally occurring amino acid;
$D^{16}$ is L or a hydrophobic non-naturally occurring amino acid;
$D^{17}$ is D or a polar non-naturally occurring amino acid;
$D^{18}$ is E or a non-naturally occurring amino acid;
$D^{19}$ is R or a basic non-naturally occurring amino acid;
$D^{20}$ is P;
$D^{21}$ is P;
$D^{22}$ is R or a basic non-naturally occurring amino acid;
$D^{23}$ is A or a small non-naturally occurring amino acid;
$D^{24}$ is H or a basic non-naturally occurring amino acid;
$D^{25}$ is A or a small non-naturally occurring amino acid;
$D^{26}$ is Q or a polar non-naturally occurring amino acid;
$D^{27}$ is H or a basic non-naturally occurring amino acid;
$D^{28}$ is F or a hydrophobic non-naturally occurring amino acid;
$D^{29}$ is H or a basic non-naturally occurring amino acid;
$D^{30}$ is K or a basic non-naturally occurring amino acid;
$D^{31}$ is H or a basic non-naturally occurring amino acid;
$D^{32}$ is Q or a polar non-naturally occurring amino acid;
$D^{33}$ is L or a hydrophobic non-naturally occurring amino acid;
$D^{34}$ is W or a hydrophobic non-naturally occurring amino acid;
$D^{35}$ is P;
$D^{36}$ is S or a polar non-naturally occurring amino acid;
$D^{37}$ is P;
$D^{38}$ is F or a hydrophobic non-naturally occurring amino acid;
$D^{39}$ is R or a basic non-naturally occurring amino acid;
$D^{40}$ is A or a hydrophobic non-naturally occurring amino acid;
$D^{41}$ is L or a hydrophobic non-naturally occurring amino acid;
$D^{42}$ is K or a basic non-naturally occurring amino acid;
$D^{43}$ is P;
$D^{44}$ is R or a hydrophobic non-naturally occurring amino acid;
$D^{45}$ is P;
wherein Formula V is

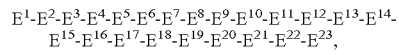

or a pharmaceutically acceptable salt thereof, wherein
$E^1$ is A or a small non-naturally occurring amino acid;
$E^2$ is H or a basic non-naturally occurring amino acid;
$E^3$ is A or a small non-naturally occurring amino acid;
$E^4$ is Q or a polar non-naturally occurring amino acid;
$E^5$ is H or a basic non-naturally occurring amino acid;
$E^6$ is F or a hydrophobic non-naturally occurring amino acid;
$E^7$ is H or a basic non-naturally occurring amino acid;
$E^8$ is K or a basic non-naturally occurring amino acid;
$E^9$ is H or a basic non-naturally occurring amino acid;
$E^{10}$ is Q or a polar non-naturally occurring amino acid;
$E^{11}$ is L or a hydrophobic non-naturally occurring amino acid;
$E^{12}$ is W or a hydrophobic non-naturally occurring amino acid;
$E^{13}$ is P;
$E^{14}$ is S;
$E^{15}$ is P;
$E^{16}$ is F or a hydrophobic non-naturally occurring amino acid;
$E^{17}$ is R or a basic non-naturally occurring amino acid;
$E^{18}$ is A or a small non-naturally occurring amino acid.
$E^{19}$ is L or a hydrophobic non-naturally occurring amino acid;
$E^{20}$ is K or a basic non-naturally occurring amino acid;
$E^{21}$ is p;
$E^{22}$ is R or a basic non-naturally occurring amino acid;
$E^{23}$ is P;
wherein Formula VI is

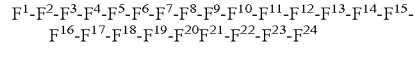

or a pharmaceutically acceptable salt thereof, wherein
$F^1$ is absent or H or a basic non-naturally occurring amino acid;
$F^2$ is absent or K or a basic non-naturally occurring amino acid;
$F^3$ is absent or R or a basic non-naturally occurring amino acid;
$F^4$ is T or a polar non-naturally occurring amino acid;
$F^5$ is I or a hydrophobic non-naturally occurring amino acid;
$F^6$ is P;
$F^7$ is M or norleucine (Nle) or another hydrophobic non-naturally occurring amino acid;
$F^8$ is F or a hydrophobic non-naturally occurring amino acid;
$F^9$ is V or a hydrophobic non-naturally occurring amino acid;
$F^{10}$ is P;
$F^{11}$ is E or a non-naturally occurring amino acid;
$F^{12}$ is S;
$F^{13}$ is T or a polar non-naturally occurring amino acid;
$F^{14}$ is S;
$F^{15}$ is K or a basic non-naturally occurring amino acid;
$F^{16}$ is L or a hydrophobic non-naturally occurring amino acid;
$F^{17}$ is Q or a polar non-naturally occurring amino acid;
$F^{18}$ is K or a basic non-naturally occurring amino acid;

$F^{19}$ is F or a polar non-naturally occurring amino acid;
$F^{20}$ is T or polar non-naturally occurring amino acid;
$F^{21}$ is S;
$F^{22}$ is W or a hydrophobic non-naturally occurring amino acid;
$F^{23}$ is F or a polar non-naturally occurring amino acid;
$F^{24}$ is M or norleucine (Nle) or another hydrophobic non-naturally occurring amino acid.

The invention in another embodiment includes any one of the foregoing peptides, wherein said peptide binds to a G-protein coupled receptor (GPCR) protein.

The invention in another embodiment includes any one of the foregoing peptides, wherein said GPCR protein belongs to the Mas-related family of proteins, selected from the group consisting of Mas, MrgX1, MrgX2 and other MrgXs; or wherein said GPCR protein belongs to the FPR-related family of proteins, selected from the group consisting of FPR, FPRL1 and FPRL2.

The invention in another embodiment includes any one of the foregoing peptides, wherein said peptide activates a GPCR protein.

The invention in another embodiment includes any one of the foregoing peptides, wherein said GPCR protein is the Mas protein, and when said peptide is Formula I or Formula II.

The invention in another embodiment includes any one of the foregoing peptides, wherein said GPCR protein is the MrgX1 protein (Mas-related G-protein coupled receptor member X1, also known as SNSR4), and when said peptide is Formula III.

The invention in another embodiment includes any one of the foregoing peptides, wherein said GPCR protein is the MrgX2 protein (Mas-related G-protein coupled receptor member X2), and when said peptide is Formula I, Formula III, Formula IV, or Formula V.

The invention in another embodiment includes any one of the foregoing peptides, wherein said GPCR protein is the FPRL1 protein when said peptide is Formula III or Formula IV.

The invention in another embodiment includes any one of the foregoing peptides, wherein said peptide is a degradation product of a naturally occurring protein isolated from a cell.

The invention in another embodiment includes any one of the foregoing peptides, wherein said peptide is isolated from a protein recombinantly produced in a cell, selected from a prokaryotic or eukaryotic cell.

The invention in another embodiment includes any one of the foregoing peptides, wherein said peptide is chemically synthesized in vitro.

The invention in another embodiment includes any one of the foregoing peptides, wherein said peptide is coupled to a biotin moiety, or wherein said peptide includes a disulfide bond, or wherein said peptide is a cyclic peptide, or wherein said peptide is a cyclic lactam, or wherein said peptide is a branched peptide, or wherein said peptide is phosphorylated, optionally wherein phosphorylation is at an S, T, or Y residue.

The invention in another embodiment includes any one of the foregoing peptides, wherein said peptide is modified at its amino terminus, optionally wherein said amino terminal modification includes an N-glycated, N-alkylated, N-acetylated or N-acylated amino acid.

The invention in another embodiment includes any one of the foregoing peptides, wherein said peptide is pegylated or sialylated.

The invention in another embodiment includes any one of the foregoing peptides, wherein said peptide includes a C-terminal amidated amino acid.

The invention in another embodiment includes any one of the foregoing peptides, wherein said non-naturally occurring amino acid is an omega-amino acid.

The invention in another embodiment includes any one of the foregoing peptides, wherein said omega-acid is beta-alanine (beta-Ala), or 3 aminopropionic (3-aP).

The invention in another embodiment includes any one of the foregoing peptides, wherein said small non-naturally occurring amino acid is sarcosine (Sar), β-alanine (β-Ala), 2,3 diaminopropionic (2,3-diaP) or alpha-aminisobutyric acid (Aib); omega-acid is beta-alanine (beta-Ala), or 3 aminopropionic (3-aP).

The invention in another embodiment includes any one of the foregoing peptides, wherein said hydrophobic non-naturally occurring amino acid is t butylalanine (t BuA), t butylglycine (t BuG), N methylisoleucine (N MeIle), norleucine (Nle), methylvaline (Mvl), cyclohexylalanine (Cha), phenylglycine (Phg), NA, β2-thienylalanine (Thi), 2 naphthylalanine (2 Nal), or 1,2,3,4-tetrahydroisoquinoline-3 carboxylic acid (Tic).

The invention in another embodiment includes any one of the foregoing peptides, wherein said basic non-naturally occurring amino acid is ornithine (Orn) or homoarginine (Har).

The invention in another embodiment includes any one of the foregoing peptides, wherein neutral/polar non-naturally occurring amino acid is citrulline (Cit), Acetyl Lys, or methionine sulfoxide (MSO).

The invention in another embodiment includes any one of the foregoing peptides, wherein said peptide is less than 75, 50, 30, 20 or 10 amino acids.

The invention in another embodiment includes any one of the foregoing peptides, wherein said peptide comprises the amino acid sequence of Formula I, wherein the peptide is selected from the group consisting of:
FLGYCIYLNRKRRGDPAFKRRLRD (SEQ ID NO. 9) monomer or dimer,
FLGYSIYLNRKRRGDPAFKRRLRD (SEQ ID NO. 10),
IYLNRKRRGDPAFKRRLRD (SEQ ID NO. 11),
FAFLGYSIYLNRKRRGDPAF (SEQ ID NO. 12),
FAFLGYCIYLNRKRRGDPAF (SEQ ID NO. 13) monomer or dimer,
FAFLGYSIYLN (SEQ ID NO. 18),
FAFLGYCIYLN (SEQ ID NO. 19) monomer or dimer,
FAFLGYCIYLNRKRRGDPAFKRRLRD (SEQ ID NO. 20) monomer or dimer,
FLGYCIYLN (SEQ ID NO. 21) monomer or dimer,
FLGYCIYLNR (SEQ ID NO. 22) monomer or dimer,
FLGYCIYLNRKRRGDPAF (SEQ ID NO. 23) monomer or dimer,
RGDPAF (SEQ ID NO. 24),
RRGDPAF (SEQ ID NO. 25),
GDPAFKRRLRD (SEQ ID NO. 28),
GDPAF (SEQ ID NO. 29),
IYLN (SEQ ID NO. 30),
IYLNRKRRGDPAF (SEQ ID NO. 31);
or
wherein the peptide comprises the amino acid sequence of Formula II, wherein the peptide is selected from the group consisting of:
monomer or dimer of SMCHRWSRAVLFPAAHRP (SEQ ID NO. 6),
SMVHRWSRAVLFPAAHRP (SEQ ID NO. 7),
RWSRAVLFPAAHRP (SEQ ID NO. 14),
HRWSRAVLFPAAHRP (SEQ ID NO. 15),
WSRAVLFPAAHRP (SEQ ID NO. 16),
AVLFPAAHRP (SEQ ID NO. 27);

or
wherein the peptide comprises the amino acid sequence of Formula III, wherein the peptide is selected from the group consisting of:
GIGSVWHWKHRVATRFTLPRFLQ (SEQ ID NO. 8),
GIGCVWHWKHRVATRFTLPRFLQ (SEQ ID NO. 39) monomer or dimer,
GIGCVWHWKHRVATRFTLPRFLQRR (SEQ ID NO. 40) monomer or dimer,
GIGCVWHWKHRVATRFTLPRFLQRRSS (SEQ ID NO. 41) monomer or dimer,
GIGCVWHWKHRVATRFTLPRFLQRRSSR (SEQ ID NO. 42) monomer or dimer,
IGCVWHWKHRVATRFTLPRFLQ (SEQ ID NO. 43) monomer or dimer,
IGCVWHWKHRVATRFTLPRFLQRR (SEQ ID NO. 44) monomer or dimer,
IGCVWHWKHRVATRFTLPRFLQRRSS (SEQ ID NO. 45) monomer or dimer,
IGCVWHWKHRVATRFTLPRFLQRRSSR (SEQ ID NO. 46) monomer or dimer,
CVWHWKHRVATRFTLPRFLQ (SEQ ID NO. 47) monomer or dimer,
CVWHWKHRVATRFTLPRFLQRR (SEQ ID NO. 48) monomer or dimer,
CVWHWKHRVATRFTLPRFLQRRSS (SEQ ID NO. 49) monomer or dimer,
CVWHWKHRVATRFTLPRFLQRRSSR (SEQ ID NO. 50) monomer or dimer;
or
wherein the peptide comprises the amino acid sequence of Formula IV, wherein the peptide is selected from the group consisting of:
AAQATGPLQDNELPGLDERPPRAHAQHF-HKHQLWPSPFRALKPRP (SEQ ID NO. 5),
AAQATGPLQDNELPGLDERPP (SEQ ID 32),
AAQATGPLQDNELPGLDERPPRAHAQHFH (SEQ ID NO. 33),
PPRAHAQHFHKHQLWPSPFRALKPRP (SEQ ID NO. 34),
HQLWPSPFRALKPRP (SEQ ID NO. 35);
or
wherein peptide comprises the amino acid sequence of Formula V, wherein the peptide is selected from the group consisting of:
AHAQHFHKHQLWPSPFRALKPRP (SEQ ID NO. 17);
or
wherein peptide comprises the amino acid sequence of Formula VI, wherein the peptide is selected from the group consisting of:
TIPMFVPESTSKLQKFTSWFM (SEQ ID NO. 1),
FTSWFM (SEQ ID NO. 2),
LQKFTSWFM (SEQ ID NO. 3),
TIPMFVPESTSTLQKFTSWFM (SEQ ID NO. 4),
HKRTIPMFVPESTSKLQKFTSWFM (SEQ ID NO. 26),
TIPMFVPESTSKLQ (SEQ ID NO. 36),
TIPMFVPESTSTLQ (SEQ ID NO. 37),
TIPMFVPESTS (SEQ ID NO. 38).

The invention in another embodiment includes any one of the foregoing peptides, wherein said peptide is conjugated or fused to a second peptide or polypeptide, optionally wherein said second peptide or polypeptide are multiple antigenic peptides (MAP), or wherein said second peptide or polypeptide comprises a portion of an immunoglobulin, or wherein said second peptide or polypeptide comprises albumin or a portion of albumin.

The invention in another embodiment includes any one of the foregoing peptides, wherein said second peptide or polypeptide includes a signal sequence.

The invention in another embodiment includes any one of the foregoing peptides, wherein signal sequence comprises: MPSVRSLLRLLAAAAACGAFA (SEQ ID NO:51) or MPSVRSLLRLLAAAAACGA (SEQ ID NO:52) when said peptide is Formula I;
MHWKMLLLLLLYYNAEA (SEQ ID NO:53) when said peptide is Formula II;
MSKSCGNNLAAISVGISLLLLLVVC (SEQ ID NO:54) when said peptide is Formula III;
MAHVPARTSPGPGPQLLLLLLPLFLLLLRDVAG (SEQ ID NO: 55) when said peptide is Formula IV;
MAHVPARTSPGPGPQLLLLLLPLFLLLLRDVAG (SEQ ID NO:55) when said peptide is Formula V; or MATASPSV-FLLMVNGQVES (SEQ ID NO:56) when said peptide is Formula VI.

The invention in another embodiment includes a pharmaceutical composition comprising any one of the foregoing peptides and a pharmaceutically acceptable carrier.

The invention in another embodiment includes a peptide comprising a fragment of any one of the foregoing peptides, wherein said peptide fragment binds or activates a G-protein coupled receptor (GPCR) protein, optionally wherein said GPCR protein belongs to the Mas-related family of proteins, selected from the group consisting of Mas, MrgX1, MrgX2 and other MrgXs; or wherein said GPCR protein belongs to the FPR-related family of proteins, selected from the group consisting of FPR, FPRL1 and FPRL2.

The invention in another embodiment includes any one of the foregoing peptide fragments, wherein said GPCR protein is the Mas protein when said peptide is Formula I or II.

The invention in another embodiment includes any one of the foregoing peptide fragments, wherein said GPCR protein is the MrgX1 protein (also known as SNSR4) when said peptide is Formula III.

The invention in another embodiment includes any one of the foregoing peptide fragments, wherein said GPCR protein is the MrgX2 protein when said peptide is Formula I, Formula III, Formula IV, or Formula V.

The invention in another embodiment includes any one of the foregoing peptide fragments, wherein said GPCR protein is the FPRL1 protein when said peptide is Formula II, Formula IV, or Formula VI.

The invention in another embodiment includes a purified nucleic acid sequence encoding any one of the foregoing peptides.

The invention in another embodiment includes a method of treating a disorder associated with hypertension, said method comprising administering to a subject in need thereof a therapeutically effective amount of any one of the foregoing peptides, wherein said peptide is Formula I, Formula II, Formula III, Formula IV or Formula V.

The invention in another embodiment includes the foregoing method, wherein said hypertension associated disorder is selected from the group consisting of hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; cardiac arrhythmias; atrial fibrillation; portal hypertension; raised intraocular pressure; vascular restenosis; chronic hypertension; valvular disease;

myocardial ischemia; acute pulmonary edema; acute coronary syndrome; hypertensive retinopathy; hypertensive pregnancy sickness; preeclampsia; Raynaud's phenomenon; erectile dysfunction and glaucoma. These peptides are also used as a vasodilator and in anti-thrombotic therapy.

The invention in another embodiment includes a method of treating a cardiovascular disorder, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said cardiovascular disorder is selected from a group consisting of peripheral vascular diseases and coronary artery diseases, myocardial infarction; heart injury; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; and platelet aggregation.

The invention in another embodiment includes a method of treating an ischemia-reperfusion injury related disorder, said method comprising administering to a subject in need thereof a therapeutically effective amount of any one of foregoing peptides, wherein said peptide is Formula I, Formula II, Formula IV, or Formula VI.

The invention in another embodiment includes the foregoing method, wherein said ischemia-reperfusion injury related disorder is associated with ischemic and post-ischemic events in organs and tissues, and the disorder is selected from a group consisting of thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation; or following conditions selected from a list comprising of procedures such as cardiac surgery; organ surgery; organ transplantation; angiography; cardiopulmonary and cerebral resuscitation.

The invention in another embodiment includes a method of treating a central nervous system (CNS) disorder or a peripheral nervous system (PNS) disorder in a subject, said method comprising administering to a subject in need thereof a therapeutically effective amount of any one of foregoing peptides, and wherein said peptide is Formula I, Formula II, Formula III, Formula IV, or Formula V.

The invention in another embodiment includes the foregoing method, wherein said CNS or PNS disorder is selected from the group consisting of central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, and locomotor activity.

The invention in another embodiment includes a method of treating an inflammatory disorder in a subject, said method comprising administering to a subject in need thereof a therapeutically effective amount of any one of the foregoing peptides, wherein said peptide is Formula I, Formula II, Formula III, Formula IV, Formula V, or Formula VI.

The invention in another embodiment includes the foregoing method, wherein said inflammatory disorder is selected from the group consisting of gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, selected from the list comprising of psoriasis, atopic dermatitis, and eczema.

The invention in another embodiment includes a method of treating inflammatory conditions associated with an infection, said infection being a bacterial infection or viral infection or an infection caused by another type of pathogen, in a subject, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said inflammatory disorder is associated with a bacterial infection or viral infection or an infection caused by another type of pathogen, selected from a group consisting of a viral infection caused by human immunodeficiency virus I (HIV-1) or HIV-2, acquired immune deficiency (AIDS), West Nile encephalitis virus, coronavirus, rhinovirus, influenza virus, dengue virus, hemorrhagic fever; an otological infection; severe acute respiratory syndrome (SARS), sepsis and sinusitis.

The invention in another embodiment includes a method of treating a metabolic disorder in a subject, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said metabolic disorder is selected from a group consisting of diabetes, diabetis mellitus, lipodystrophy, hyperthyroidism, glaucoma, hyperlipidaemia, non-insulin dependent diabetes, appetite control and obesity.

The invention in another embodiment includes a method of treating a fibrotic condition in a subject, involving tissue remodeling following inflammation or ischemia-reperfusion injury, said method comprising administering to a subject in need thereof a therapeutically effective amount of any one of the foregoing peptides, wherein said peptide is Formula I, Formula II, Formula III, Formula IV, Formula V or Formula VI.

The invention in another embodiment includes the foregoing method, wherein said fibrotic conditions is selected from a group consisting of endomyocardial fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis); fibromatosis; granulomatous lung disease; and glomerulonephritis The invention in another embodiment includes a method of prevention and treatment of a disease in a subject, involving reduction of oxygen reactive species with consequent endothelial dysfunction, said method comprising administering to a subject in need thereof a therapeutically effective amount of any one of the foregoing peptides, wherein said peptide is Formula I, or Formula II.

The invention in another embodiment includes the foregoing method, wherein said endothelial dysfunction disease is selected from a group consisting of cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

The invention in another embodiment includes a method of treating a respiratory disease in a subject, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said respiratory disease is selected from a group consisting of asthma, bronchial disease, lung diseases, cystic fibrosis, chronic obstructive pulmonary disease (COPD), Acute Respiratory Distress Syndrome (ARDS), severe acute respiratory syndrome (SARS).

The invention in another embodiment includes a method of preventing or treating a skin injury or tissue repair, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said skin injury is selected from a group selected of dermal repair, wound healing; burns, erythemas, skin or tissue lesions, and skin tumors.

The invention in another embodiment includes a method of treating a bone disease in a subject, said method comprising administering to a subject in need thereof a therapeutically effective amount of any one of the foregoing peptides, wherein said peptide is Formula II, Formula IV, or Formula VI.

The invention in another embodiment includes the foregoing method, wherein said bone disease is osteoporosis.

The invention in another embodiment includes a method of treating a urogenital disorder or a genitor-urological disorder in a subject, said method comprising administering to a subject in need thereof a therapeutically effective amount of any one of the foregoing peptides, wherein said peptide is Formula I, Formula II.

The invention in another embodiment includes the foregoing method, wherein said urogenital disorder or genitor-urological disorders is selected from group consisting of a renal disease; a bladder disorder; disorders of the reproductive system; gynecologic disorders; urinary tract disorder; incontinence; disorders of the male (spermatogenesis, spermatic motility), and female reproductive system; sexual dysfunction; erectile dysfunction; embryogenesis; pregnancy related disorders and pregnancy monitoring.

The invention in another embodiment includes a method of activating or inducing chemoattraction of blood cells to a site of injury in a subject, said method comprising administering to a subject in need thereof a therapeutically effective amount of any one of the foregoing peptides, wherein said peptide is Formula II, Formula IV or Formula VI.

The invention in another embodiment includes the foregoing method, wherein said blood cells are selected from a group consisting of phagocyte cells, platelets, monocytes, macrophages, neutrophils, eosinophils and lymphocytes.

The invention in another embodiment includes a method of treating a cytopenia in a subject, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said cytopenia is selected from a group consisting of multilineage cytopenia, a thrombocytopenia, anemia, anemia due to renal failure; lymphopenia, leucopenia, neutropenia, radio/chemotherapy-related neutropenia; and platelet disorders.

The invention in another embodiment includes a method of treating an immune related disorder in a subject, said method comprising administering to a subject in need thereof a therapeutically effective amount of any one of the foregoing peptides, wherein said peptide is Formula I, Formula II, Formula IV, or Formula VI.

The invention in another embodiment includes the foregoing method, wherein said immune related disorder is selected from a group consisting of graft versus host disease; transplant rejection, bone marrow transplantation.

The invention in another embodiment includes the foregoing method, wherein said immune related disorder is an autoimmune disease and is selected from a group consisting of multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

The invention in another embodiment includes a method of treating a cancer or inflammation associated with cancer in a patient, said method comprising administering to a subject in need thereof a therapeutically effective amount of any one of the foregoing peptides, wherein said peptide is Formula I, Formula II, Formula IV or Formula VI.

The invention in another embodiment includes the foregoing method, wherein said cancer is selected from a group consisting of colon cancer, lung cancer, breast cancer, prostate cancer, brain cancer, pancreatic cancer, ovarian cancer, kidney cancer, melanoma, glioma, a carcinoma, a sarcoma, a leukemia, or lymphoma, including their invasive and metastatic forms.

The invention in another embodiment includes a method of treating or controlling pain in a patient, said method comprising administering to a subject in need thereof a therapeutically effective amount of any one of the foregoing peptides wherein said peptide is Formula I, Formula III, Formula IV, or Formula V.

The invention in another embodiment includes the foregoing method, wherein said pain is selected from a group consisting of complex regional pain, muscoskeletal pain, neuropathic pain, post-herpetic pain, pain associated with cancer, or post-operative pain.

The invention in another embodiment includes a method of treating a kidney disease in a patient, said method comprising administering to a subject in need thereof a therapeutically effective amount of any one of the foregoing peptides, wherein said peptide is Formula I, Formula II, Formula III, Formula IV or Formula V.

The invention in another embodiment includes the foregoing method, wherein said kidney diseases is selected from a group consisting of diabetic nephropathy; glomerulosclerosis; nephropathies; renal impairment; scleroderma renal crisis and chronic renal failure.

The invention in another embodiment includes a method of treating a blood disease in a patient, said method comprising administering to a subject in need thereof a therapeutically effective amount of any one of the foregoing peptides, wherein said peptide is Formula I, or Formula II.

The invention in another embodiment includes the foregoing method, wherein said blood disease is selected from a group consisting of angioplasty (endoluminal prosthesis and post angioplasty restenosis); haematopoiesis; erythrocytosis; and disorders of the blood crasis, such as post radiotherapy.

The invention in another embodiment includes a method of treating an angiogenesis related disease in a patient, said method comprising administering to a subject in need thereof a therapeutically effective amount of any one of the foregoing peptides, wherein said peptide is Formula I, Formula II, Formula IV or Formula VI.

The invention in another embodiment includes the foregoing method, wherein said angiogenesis related disease is retinal angiogenesis in human ocular diseases and is selected from a group consisting of diabetes mellitus, retinopathy of prematury, and age-related macular degeneration.

The invention in another embodiment includes the foregoing method, wherein said angiogenesis related disease is primary or metastatic cancer, and is selected from a group consisting of prostate cancer, brain cancer, breast cancer, colorectal cancer, lung cancer, ovarian cancer, pancreatic cancer, renal cancer, cervical cancer, melanoma, soft tissue sarcomas, lymphomas, head-and-neck cancer, and glioblastomas.

The invention in another embodiment includes a method of treating a genetic polymorphism consequent diseases in a patient, said method comprising administering to a subject in need thereof a therapeutically effective amount of any one of the foregoing peptides, wherein said peptide is Formula I, or Formula II.

The invention in another embodiment includes the foregoing method, wherein said genetic polymorphism consequent diseases is selected from a group consisting of DD type of the angiotensin converting enzyme; type I and type II diabetes mellitus and complications; diabetic mellitus prophylaxis; diabetic maculopathy; and diabetic nephropathy.

The invention in another embodiment includes a method of preventing or treating a organic alterations produced by aging in a patient, said method comprising administering to a subject in need thereof a therapeutically effective amount of any one of the foregoing peptides, wherein said peptide is Formula I, or Formula II.

The invention in another embodiment includes a method of preventing or treating alopecia in a patient, including chemotherapy (such as etoposide)-induced alopecia, said method comprising administering to a subject in need thereof a therapeutically effective amount of any one of the foregoing peptides, wherein said peptide is Formula I, Formula II, Formula IV or Formula VI.

The invention in another embodiment includes a method of preventing or treating diseases that involve alterations in the muscular differentiation, maturation and regeneration in muscular atrophies in a patient, said method comprising administering to a subject in need thereof a therapeutically effective amount of any one of the foregoing peptides, wherein said peptide is Formula I, or Formula II.

The invention in another embodiment includes the foregoing method, wherein said muscular alteration or atrophy is selected from a group consisting of cachexia; prolonged restriction to bed due to numerous factors; chronic use of corticoids; and varied neurological syndromes, traumatisms and degenerative diseases that lead to muscular atrophy.

The invention in another embodiment includes the cDNA that encodes the peptide sequences of the invention, which can be used in gene therapy.

If desired, gene therapy can be used to deliver to a subject a peptide according to the invention. A nucleic acid encoding the peptide can be inserted into vectors, which are then used as gene therapy vectors. Gene therapy vectors can be delivered to a subject by, for example, intravenous injection, local administration or by stereotactic injection. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The invention in another embodiment includes combination therapy using one or more peptides of the present invention provided in combination with another therapeutic agent or agents. As used herein, the term "combination therapy" refers to treatment of a single condition or disease involving the concomitant use of more than one therapeutic agent.

The invention in another embodiment includes an antibody that selectively binds to an epitope in any one of the foregoing peptides.

The invention in another embodiment includes any one of the foregoing antibodies, wherein said peptide is
monomer or dimer of FLGYCIYLNRKRRGDPAFKRRLRD (SEQ ID NO. 9),
FLGYSIYLNRKRRGDPAFKRRLRD (SEQ ID NO. 10),
IYLNRKRRGDPAFKRRLRD (SEQ ID NO. 11),
FAFLGYSIYLNRKRRGDPAF (SEQ ID NO. 12),
monomer or dimer of FAFLGYCIYLNRKRRGDPAF, (SEQ ID NO. 13),
FAFLGYSIYLN (SEQ ID NO. 18),
monomer or dimer of FAFLGYCIYLN (SEQ ID NO. 19),
monomer or dimer of FAFLGYCIYLNRKRRGDPAFKRRLRD (SEQ ID NO. 20),
monomer or dimer of FLGYCIYLN (SEQ ID NO. 21),
monomer or dimer of FLGYCIYLNR (SEQ ID NO. 22),
monomer or dimer of FLGYCIYLNRKRRGDPAF (SEQ ID NO. 23),
RGDPAF (SEQ ID NO. 24),
RRGDPAF (SEQ ID NO. 25),
GDPAFKRRLRD (SEQ ID NO. 28),
GDPAF (SEQ ID NO. 29),
IYLN (SEQ ID NO. 30),
IYLNRKRRGDPAF (SEQ ID NO. 31),
monomer or dimer of SMCHRWSRAVLFPAAHRP (SEQ ID NO. 6),
SMVHRWSRAVLFPAAHRP (SEQ ID NO. 7)
RWSRAVLFPAAHRP (SEQ ID NO. 14),
HRWSRAVLFPAAHRP (SEQ ID NO. 15),
WSRAVLFPAAHRP (SEQ ID NO. 16),
AVLFPAAHRP (SEQ ID NO. 27),
GIGSVWHWKHRVATRFTLPRFLQ (SEQ ID NO. 8), monomer or dimer of GIGCVWHWKHRVATRFTLPRFLQ (SEQ ID NO. 39),
monomer or dimer of GIGCVWHWKHRVATRFTLPRFLQRR (SEQ ID NO. 40),
monomer or dimer of GIGCVWHWKHRVATRFTLPRFLQRRSS (SEQ ID NO. 41),
monomer or dimer of GIGCVWHWKHRVATRFTLPRFLQRRSSR (SEQ ID NO. 42),
monomer or dimer of IGCVWHWKHRVATRFTLPRFLQ (SEQ ID NO. 43),
monomer or dimer of IGCVWHWKHRVATRFTLPRFLQRR (SEQ ID NO. 44),
monomer or dimer of IGCVWHWKHRVATRFTLPRFLQRRSS (SEQ ID NO. 45),
monomer or dimer of IGCVWHWKHRVATRFTLPRFLQRRSSR (SEQ ID NO. 46),
monomer or dimer of CVWHWKHRVATRFTLPRFLQ (SEQ ID NO. 47),
monomer or dimer of CVWHWKHRVATRFTLPRFLQRR (SEQ ID NO. 48),
monomer or dimer of CVWHWKHRVATRFTLPRFLQRRSS (SEQ ID NO. 49),
monomer or dimer of CVWHWKHRVATRFTLPRFLQRRSSR (SEQ ID NO. 50),
AAQATGPLQDNELPGLDERPPRAHAQHFHKHQLWPSPFRALKPRP (SEQ ID NO. 5),
AAQATGPLQDNELPGLDERPP (SEQ ID 32),
AAQATGPLQDNELPGLDERPPRAHAQHFH (SEQ ID NO. 33),
PPRAHAQHFHKHQLWPSPFRALKPRP (SEQ ID NO. 34),
HQLWPSPFRALKPRP (SEQ ID NO.35),
AHAQHFHKHQLWPSPFRALKPRP (SEQ ID NO. 17),
TIPMFVPESTSKLQKFTSWFM (SEQ ID NO. 1),
FTSWFM (SEQ ID NO. 2),
LQKFTSWFM (SEQ ID NO. 3),
TIPMFVPESTSTLQKFTSWFM (SEQ ID NO. 4),
HKRTIPMFVPESTSKLQKFTSWFM (SEQ ID NO. 26),
TIPMFVPESTSKLQ (SEQ ID NO. 36),
TIPMFVPESTSTLQ (SEQ ID NO. 37),
TIPMFVPESTS (SEQ ID NO. 38).

The invention in another embodiment includes any one of the foregoing antibodies, wherein the antibody is a monoclonal antibody.

The invention in another embodiment includes any one of the foregoing antibodies, wherein the antibody is conjugated or coupled to a detectable label, a radioactive label, an enzyme, a fluorescent label, a luminescent label, a bioluminescent label, or a therapeutic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims

BRIEF DESCRIPTION OF THE DRAWINGS

FIG. 1 lists the peptides described in this application.

FIG. 23 is a table showing the effect of P58 and Ac2-26 on zymosan-induced leukocyte influx to air pouch cavities, at the 4 h time-point.

FIG. 24 is a table depicting the effect of P58 and Ac2-26 on zymosan-induced neutrophil (GR-1+ cells) influx into air pouch cavities, at the 4 h time-point.

FIG. 26 is a table demonstrating the effect of P58 and analogs on zymosan-induced leukocyte influx to air pouch cavities at the 4 h time-point.

FIG. 27 is a table showing the effect of P58 and analogs on zymosan induced neutrophil (GR-1+) influx to air pouch cavities at the 4 h time-point.

FIG. 28 is a representative scheme of the experiment flow showing the cumulative concentration response curve with P61_S, P61_D, P33_V, and P33_D in vessels pre-contracted with 0.1 uM phenylephrine (PHE). The X axis represents the time and the y axis depicts the level of contraction.

DETAILED DESCRIPTION OF THE INVENTION

Figure 2:
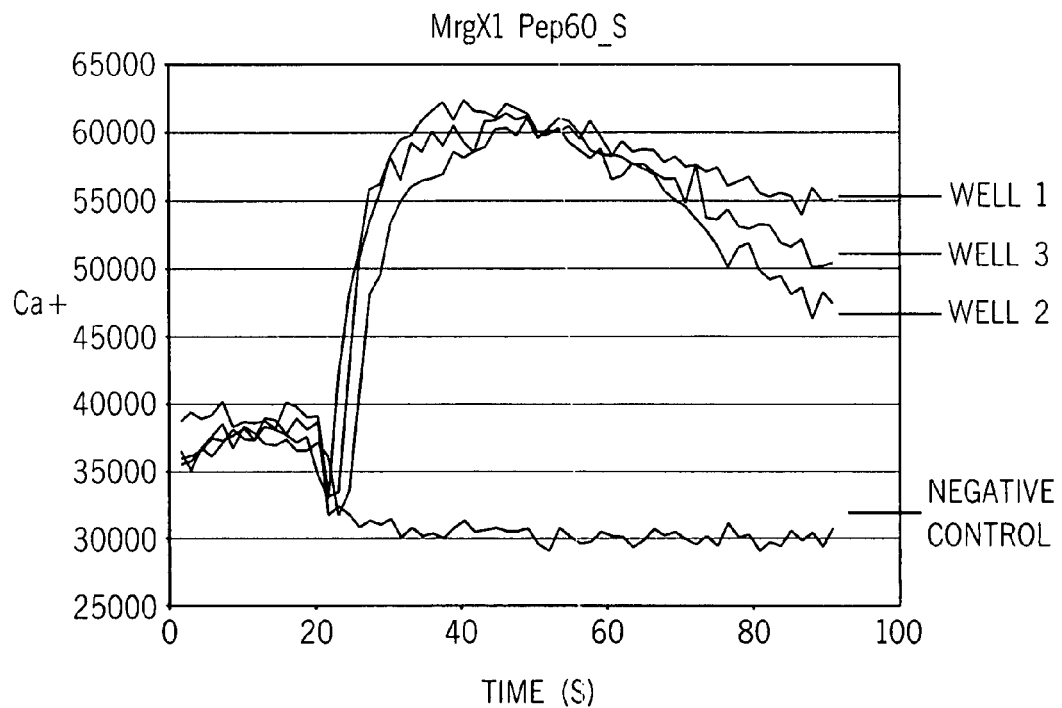
FIG. 2 is a line graph demonstrating the effect of Peptide 60_S on calcium flux in CHO—K1 cells transfected with MrgX1.

The invention provides bioactive peptides. These peptides are useful, inter alia, for treating a variety of indications and disorders, which are discussed in detail below. In some embodiments, the peptides are ligands for GPCR receptors.

Provided are bioactive peptides falling within Formula I (also known as the Peptide 61-type peptides), Formula II (Peptide 33-type peptides), Formula III (Peptide 60-type peptides), Formula IV (also known as the Peptide 94-type peptides), Formula V (Peptide 63-type peptides), or Formula VI (Peptide 58-type peptides).

Formula I includes compounds falling within the following formula:

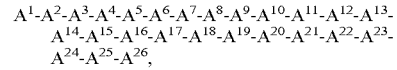

or a pharmaceutically acceptable salt thereof, wherein $A^1$ is absent or F or a hydrophobic non-naturally occurring amino acid;

$A^2$ is absent or A or a small non-naturally occurring amino acid;

$A^3$ is absent or F or a hydrophobic non-naturally occurring amino acid;

$A^4$ is absent or L or a hydrophobic non-naturally occurring amino acid;

$A^5$ is absent or G or a small non-naturally occurring amino acid;

$A^6$ is absent or Y or a hydrophobic non-naturally occurring amino acid;

$A^7$ is absent or S or C;

$A^8$ is absent or I or a hydrophobic non-naturally occurring amino acid;

$A^9$ is absent or Y or a hydrophobic non-naturally occurring amino acid;

$A^{10}$ is absent or L or a hydrophobic non-naturally occurring amino acid;

$A^{11}$ is absent or N or a polar non-naturally occurring amino acid;

$A^{12}$ is absent or R or a basic non-naturally occurring amino acid;

$A^{13}$ is absent or K or a basic non-naturally occurring amino acid;

$A^{14}$ is absent or R or a basic non-naturally occurring amino acid;

$A^{15}$ is absent or R or a basic non-naturally occurring amino acid;

$A^{16}$ is absent or G, or a small non-naturally occurring amino acid;

$A^{17}$ is absent or D or a polar non-naturally occurring amino acid;

$A^{18}$ is absent or P;

$A^{19}$ is absent or A or a hydrophobic non-naturally occurring amino acid;

$A^{20}$ is absent or F or a hydrophobic non-naturally occurring amino acid;

$A^{21}$ is absent or K or a basic non-naturally occurring amino acid;

$A^{22}$ is absent or R or a basic non-naturally occurring amino acid;

$A^{23}$ is absent or R or a basic non-naturally occurring amino acid;

$A^{24}$ is absent or L or a hydrophobic non-naturally occurring amino acid;

$A^{25}$ is absent or R or a hydrophobic non-naturally occurring amino acid;

$A^{26}$ is absent or D or a polar non-naturally occurring amino acid.

In some embodiments, a peptide of Formula I includes the amino acid sequences FLGYCIYLNRKRRGDPAFKRRLRD monomer or dimer (SEQ ID NO:9), also referred to herein is as Peptide 61 (P61), or FLGYSIYLNRKRRGDPAFKRRLRD (SEQ ID NO:10), also referred to herein is as Peptide 61_S(P61_S).

P61-type peptides falling within Formula I are listed in Table 1 below:

TABLE 1

P61-type peptides falling within Formula I.

| Name | Sequence | SEQ ID |
|---|---|---|
| P_61 | FLGYCIYLNRKRRGDPAFKRRLRD | SEQ ID 9 |
| P_61_S | FLGYSIYLNRKRRGDPAFKRRLRD | SEQ ID 10 |
| P61_4 | IYLNRKRRGDPAFKRRLRD | SEQ ID 11 |
| P61_11S | FAFLGYSIYLNRKRRGDPAF | SEQ ID 12 |
| P61_11 | FAFLGYCIYLNRKRRGDPAF | SEQ ID 13 |
| P61_5S | FAFLGYSIYLN | SEQ ID 18 |
| P61_5 | FAFLGYCIYLN | SEQ ID 19 |
| P61 derivative | FAFLGYCIYLNRKRRGDPAFKRRLRD | SEQ ID 20 |

TABLE 1-continued

P61-type peptides falling within Formula I.

| Name | Sequence | SEQ ID |
|---|---|---|
| P61 derivative | FLGYCIYLN | SEQ ID 21 |
| P61 derivative | FLGYCIYLNR | SEQ ID 22 |
| P61 derivative | FLGYCIYLNRKRRGDPAF | SEQ ID 23 |
| P61 derivative | RGDPAF | SEQ ID 24 |
| P61 derivative | RRGDPAF | SEQ ID 25 |
| P61_14 | GDPAFKRRLRD | SEQ ID 28 |
| P61_16 | GDPAF | SEQ ID 29 |
| P61_7 | IYLN | SEQ ID 30 |
| P61_13 | IYLNRKRRGDPAF | SEQ ID 31 |

Compounds of Formula II include the following:

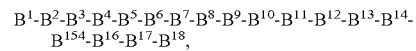

or a pharmaceutically acceptable salt thereof, wherein $B^1$ is absent or S;

$B^2$ is absent or M or norleucine (Nle) or another hydrophobic non-naturally occurring amino acid;

$B^3$ is absent or C or V;

$B^4$ is absent or H or a basic non-naturally occurring amino acid;

$B^5$ is absent or R or a basic non-naturally occurring amino acid;

$B^6$ is absent or W or a hydrophobic non-naturally occurring amino acid $B^7$ is absent or S;

$B^8$ is absent or R or a hydrophobic non-naturally occurring amino acid;

$B^9$ is A or a small non-naturally occurring amino acid;

$B^{10}$ is V or a hydrophobic non-naturally occurring amino acid;

$B^{11}$ is L or a hydrophobic non-naturally occurring amino acid;

$B^{12}$ is F or a hydrophobic non-naturally occurring amino acid;

$B^{13}$ is P;

$B^{14}$ is A or a hydrophobic non-naturally occurring amino acid;

$B^{15}$ is A or a hydrophobic non-naturally occurring amino acid;

$B^{16}$ is H or a basic non-naturally occurring amino acid;

$B^{17}$ is R or a basic non-naturally occurring amino acid;

$B^{18}$ is P.

Examples of peptides within Formula II include SMCHRWSRAVLFPAAHRP monomer or dimer (SEQ ID NO:6), also referred herein as P33; and SMVHRWSRAVLFPAAHRP (SEQ ID NO:7), also referred herein as P33_V. Other examples of P33-type peptides falling within Formula II are listed in Table 2 below:

TABLE 2

P33-type peptides falling within Formula II.

| Name | Sequence | SEQ ID |
|------|----------|--------|
| P33 | SMCHRWSRAVLFPAAHRP | SEQ ID 6 |
| P33_V | SMVHRWSRAVLFPAAHRP | SEQ ID 7 |
| P33_8 | RWSRAVLFPAAHRP | SEQ ID 14 |
| P33_9 | HRWSRAVLFPAAHRP | SEQ ID 15 |
| P33_10 | WSRAVLFPAAHRP | SEQ ID 16 |
| P33_5 | AVLFPAAHRP | SEQ ID 27 |

Formula III includes compounds falling within the following formula:

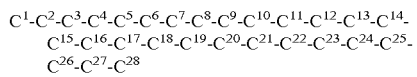

$C^1$-$C^2$-$C^3$-$C^4$-$C^5$-$C^6$-$C^7$-$C^8$-$C^9$-$C^{10}$-$C^{11}$-$C^{12}$-$C^{13}$-$C^{14}$-$C^{15}$-$C^{16}$-$C^{17}$-$C^{18}$-$C^{19}$-$C^{20}$-$C^{21}$-$C^{22}$-$C^{23}$-$C^{24}$-$C^{25}$-$C^{26}$-$C^{27}$-$C^{28}$ or a pharmaceutically acceptable salt thereof, wherein
$C^1$ is absent or G or a small non-naturally occurring amino acid;
$C^2$ is absent or I or a hydrophobic non-naturally occurring amino acid;
$C^3$ is absent or G or a small non-naturally occurring amino acid;
$C^4$ is C or S or a polar non-naturally occurring amino acid;
$C^5$ is V or a hydrophobic non-naturally occurring amino acid;
$C^6$ is W or a hydrophobic non-naturally occurring amino acid
$C^7$ is H or a basic non-naturally occurring amino acid;
$C^8$ is W or a hydrophobic non-naturally occurring amino acid;
$C^9$ is K or a basic non-naturally occurring amino acid;
$C^{10}$ is H or a basic non-naturally occurring amino acid;
$C^{11}$ is R or a basic non-naturally occurring amino acid;
$C^{12}$ is V or a hydrophobic non-naturally occurring amino acid;
$C^{13}$ is A or a hydrophobic non-naturally occurring amino acid;
$C^{14}$ is T or a polar non-naturally occurring amino acid;
$C^{15}$ is R or a basic non-naturally occurring amino acid;
$C^{16}$ is F or a hydrophobic non-naturally occurring amino acid;
$C^{17}$ is T or a polar non-naturally occurring amino acid;
$C^{18}$ is L or a hydrophobic non-naturally occurring amino acid;
$C^{19}$ is P;
$C^{20}$ is R or basic non-naturally occurring amino acid;
$C^{21}$ is F or a polar non-naturally occurring amino acid;
$C^{22}$ is L or a hydrophobic non-naturally occurring amino acid;
$C^{23}$ is Q or a polar non-naturally occurring amino acid;
$C^{24}$ is absent or R or a basic non-naturally occurring amino acid;
$C^{25}$ is absent or R or a basic non-naturally occurring amino acid;
$C^{26}$ is absent or S or a polar non-naturally occurring amino acid;
$C^{27}$ is absent or S or a polar non-naturally occurring amino acid; or
$C^{28}$ is absent or R or a basic non-naturally occurring amino acid.

Examples of peptides that include some or all of a sequence within Formula III are shown in Table 3 below.

A peptide consisting of the amino acid sequence of GIGSVWHWKHRVATRFTLPRFLQ (SEQ ID NO:8) is also referred to herein as Peptide 60_S.

TABLE 3

P60-type peptides falling within Formula III.

| Name | Sequence | SEQ ID |
|------|----------|--------|
| P60_S | GIGSVWHWKHRVATRFTLPRFLQ | SEQ ID 8 |
| P60 | GIGCVWHWKHRVATRFTLPRFLQ | SEQ ID 39 |
| P60 derivatives | GIGCVWHWKHRVATRFTLPRFLQRR | SEQ ID 40 |
| P60 derivatives | GIGCVWHWKHRVATRFTLPRFLQRRSS | SEQ ID 41 |
| P60 derivatives | GIGCVWHWKHRVATRFTLPRFLQRRSSR | SEQ ID 42 |
| P60 derivatives | IGCVWHWKHRVATRFTLPRFLQ | SEQ ID 43 |
| P60 derivatives | IGCVWHWKHRVATRFTLPRFLQRR | SEQ ID 44 |
| P60 derivatives | IGCVWHWKHRVATRFTLPRFLQRRSS | SEQ ID 45 |
| P60 derivatives | IGCVWHWKHRVATRFTLPRFLQRRSSR | SEQ ID 46 |
| P60 derivatives | CVWHWKHRVATRFTLPRFLQ | SEQ ID 47 |
| P60 derivatives | CVWHWKHRVATRFTLPRFLQRR | SEQ ID 48 |
| P60 derivatives | CVWHWKHRVATRFTLPRFLQRRSS | SEQ ID 49 |
| P60 derivatives | CVWHWKHRVATRFTLPRFLQRRSSR | SEQ ID 50 |

Formula IV includes compounds falling within the following formula:

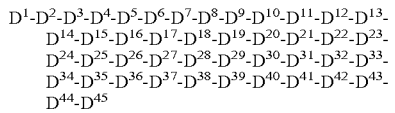

$D^1$-$D^2$-$D^3$-$D^4$-$D^5$-$D^6$-$D^7$-$D^8$-$D^9$-$D^{10}$-$D^{11}$-$D^{12}$-$D^{13}$-$D^{14}$-$D^{15}$-$D^{16}$-$D^{17}$-$D^{18}$-$D^{19}$-$D^{20}$-$D^{21}$-$D^{22}$-$D^{23}$-$D^{24}$-$D^{25}$-$D^{26}$-$D^{27}$-$D^{28}$-$D^{29}$-$D^{30}$-$D^{31}$-$D^{32}$-$D^{33}$-$D^{34}$-$D^{35}$-$D^{36}$-$D^{37}$-$D^{38}$-$D^{39}$-$D^{40}$-$D^{41}$-$D^{42}$-$D^{43}$-$D^{44}$-$D^{45}$ or a pharmaceutically acceptable salt thereof, wherein
$D^1$ is A or a small non-naturally occurring amino acid;
$D^2$ is A or a small non-naturally occurring amino acid;
$D^3$ is Q or a polar non-naturally occurring amino acid;
$D^4$ is A or a hydrophobic non-naturally occurring amino acid;
$D^5$ is T or a polar non-naturally occurring amino acid;
$D^6$ is G or a small non-naturally occurring amino acid;
$D^7$ is P;
$D^8$ is L or a hydrophobic non-naturally occurring amino acid;
$D^9$ is Q or a polar non-naturally occurring amino acid;
$D^{10}$ is D or a polar non-naturally occurring amino acid;
$D^{11}$ is N or a polar non-naturally occurring amino acid;
$D^{12}$ is E or a non-naturally occurring amino acid;
$D^{13}$ is L or a hydrophobic non-naturally occurring amino acid;
$D^{14}$ is P;
$D^{15}$ is G or a small non-naturally occurring amino acid;

$D^{16}$ is L or a hydrophobic non-naturally occurring amino acid;
$D^{17}$ is D or a polar non-naturally occurring amino acid;
$D^{18}$ is E or a non-naturally occurring amino acid;
$D^{19}$ is R or a basic non-naturally occurring amino acid;
$D^{20}$ is P;
$D^{21}$ is P;
$D^{22}$ is R or a basic non-naturally occurring amino acid;
$D^{23}$ is A or a small non-naturally occurring amino acid;
$D^{24}$ is H or a basic non-naturally occurring amino acid;
$D^{25}$ is A or a small non-naturally occurring amino acid;
$D^{26}$ is Q or a polar non-naturally occurring amino acid;
$D^{27}$ is H or a basic non-naturally occurring amino acid;
$D^{28}$ is F or a hydrophobic non-naturally occurring amino acid;
$D^{29}$ is H or a basic non-naturally occurring amino acid;
$D^{30}$ s K or a basic non-naturally occurring amino acid;
$D^{31}$ is H or a basic non-naturally occurring amino acid;
$D^{32}$ is Q or a polar non-naturally occurring amino acid;
$D^{33}$ is L or a hydrophobic non-naturally occurring amino acid;
$D^{34}$ is W or a hydrophobic non-naturally occurring amino acid;
$D^{35}$ is P;
$D^{36}$ is S or a polar non-naturally occurring amino acid;
$D^{37}$ is P;
$D^{38}$ is F or a hydrophobic non-naturally occurring amino acid;
$D^{39}$ is R or a basic non-naturally occurring amino acid;
$D^{40}$ is A or a hydrophobic non-naturally occurring amino acid;
$D^{41}$ is L or a hydrophobic non-naturally occurring amino acid;
$D^{42}$ is K or a basic non-naturally occurring amino acid;
$D^{43}$ is P;
$D^{44}$ is R or a hydrophobic non-naturally occurring amino acid;
$D^{45}$ is P.

In some embodiments, a peptide of Formula IV includes the amino acid sequence as listed in Table 4 below.

A peptide consisting of the amino acid sequence AAQAT-GPLQDNELPGLDERPPRAHAQHFHKHQL-WPSPFRALKPRP (SEQ ID NO: 5) is also referred to herein is as Peptide 94.

$E^4$ is Q or a polar non-naturally occurring amino acid;
$E^5$ is H or a basic non-naturally occurring amino acid;
$E^6$ is F or a hydrophobic non-naturally occurring amino acid;
$E^7$ is H or a basic non-naturally occurring amino acid;
$E^8$ is K or a basic non-naturally occurring amino acid;
$E^9$ is H or a basic non-naturally occurring amino acid;
$E^{10}$ is Q or a polar non-naturally occurring amino acid;
$E^{11}$ is L or a hydrophobic non-naturally occurring amino acid;
$E^{12}$ is W or a hydrophobic non-naturally occurring amino acid;
$E^{13}$ is P;
$E^{14}$ is S;
$E^{15}$ is P;
$E^{16}$ is F or a hydrophobic non-naturally occurring amino acid;
$E^{17}$ is R or a basic non-naturally occurring amino acid;
$E^{18}$ is A or a small non-naturally occurring amino acid.
$E^{19}$ is L or a hydrophobic non-naturally occurring amino acid;
$E^{20}$ is K or a basic non-naturally occurring amino acid;
$E^{21}$ is P;
$E^{22}$ is R or a basic non-naturally occurring amino acid;
$E^{23}$ is P.

Examples of P63-type peptides within Formula V include AHAQHFHKHQLWPSPFRALKPRP (SEQ ID NO:17 also referred to herein as Peptide 63 (P63).

Formula VI includes compounds falling within the following formula:

$$F^1\text{-}F^2\text{-}F^3\text{-}F^4\text{-}F^5\text{-}F^6\text{-}F^7\text{-}F^8\text{-}F^9\text{-}F^{10}\text{-}F^{11}\text{-}F^{12}\text{-}F^{13}\text{-}F^{14}\text{-}F^{15}\text{-}F^{16}\text{-}F^{17}\text{-}F^{18}\text{-}F^{19}\text{-}F^{20}F^{21}\text{-}F^{22}\text{-}F^{23}\text{-}F^{24}$$

or a pharmaceutically acceptable salt thereof, wherein
$F^1$ is absent or H or a basic non-naturally occurring amino acid;
$F^2$ is absent or K or a basic non-naturally occurring amino acid;
$F^3$ is absent or R or a basic non-naturally occurring amino acid;
$F^4$ is T or a polar non-naturally occurring amino acid;
$F^5$ is I or a hydrophobic non-naturally occurring amino acid;
$F^6$ is P;

TABLE 4

P94-type peptides falling within Formula IV.

| Name | Sequence | SEQ ID |
|---|---|---|
| P94 | AAQATGPLQDNELPGLDERPPRAHAQHFHKHQLWPSPFRALKPRP | SEQ ID 5 |
| P94/63_27 | AAQATGPLQDNELPGLDERPP | SEQ ID 32 |
| P94/63_26 | AAQATGPLQDNELPGLDERPPRAHAQHFH | SEQ ID 33 |
| P94/63_21 | PPRAHAQHFHKHQLWPSPFRALKPRP | SEQ ID 34 |
| P94/63_9 | HQLWPSPFRALKPRP | SEQ ID 35 |

Compounds of Formula V include the following:

$$E^1\text{-}E^2\text{-}E^3\text{-}E^4\text{-}E^5\text{-}E^6\text{-}E^7\text{-}E^8\text{-}E^9\text{-}E^{10}\text{-}E^{11}\text{-}E^{12}\text{-}E^{13}\text{-}E^{14}\text{-}E^{15}\text{-}E^{16}\text{-}E^{17}\text{-}E^{18}\text{-}E^{19}\text{-}E^{20}\text{-}E^{21}\text{-}E^{22}\text{-}E^{23},$$

or a pharmaceutically acceptable salt thereof, wherein
$E^1$ is A or a small non-naturally occurring amino acid;
$E^2$ is H or a basic non-naturally occurring amino acid;
$E^3$ is A or a small non-naturally occurring amino acid;

$F^7$ is M or norleucine (Nle) or another hydrophobic non-naturally occurring amino acid;
$F^8$ is F or a hydrophobic non-naturally occurring amino acid;
$F^9$ is V or a hydrophobic non-naturally occurring amino acid;
$F^{10}$ is P;
$F^{11}$ is E or a non-naturally occurring amino acid;

$F^{12}$ is S;
$F^{13}$ is T or a polar non-naturally occurring amino acid;
$F^{14}$ is S;
$F^{15}$ is K or a basic non-naturally occurring amino acid;
$F^{16}$ is L or a hydrophobic non-naturally occurring amino acid;
$F^{17}$ is Q or a polar non-naturally occurring amino acid;
$F^{18}$ is K or a basic non-naturally occurring amino acid;
$F^{19}$ is F or a polar non-naturally occurring amino acid;
$F^{20}$ is T or polar non-naturally occurring amino acid;
$F^{21}$ is S;
$F^{22}$ is W or a hydrophobic non-naturally occurring amino acid;
$F^{23}$ is F or a polar non-naturally occurring amino acid;
$F^{24}$ is M or norleucine (Nle) or another hydrophobic non-naturally occurring amino acid;

Examples of peptides that include some of the sequence within Formula VI are shown in Table 5 below.

A peptide consisting of the amino acid sequence of TIPM-FVPESTSKLQKFTSWFM (SEQ ID NO:1) is also referred to herein as Peptide 58.

TABLE 5

P58-type peptides falling within Formula VI:

| Name | Sequence | SEQ ID |
|---|---|---|
| P58 | TIPMFVPESTSKLQKFTSWFM-amide | SEQ ID 1 |
| P58_4 | FTSWFM-amide | SEQ ID 2 |
| P58_5 | LQKFTSWFM-amide | SEQ ID 3 |
| P58_10 | TIPMFVPESTSTLQKFTSWFM-amide | SEQ ID 4 |
| P58 derivative | HKRTIPMFVPESTSKLQKFTSWFM-amide | SEQ ID 26 |
| P58_7 | TIPMFVPESTSKLQ | SEQ ID 36 |
| P58_12 | TIPMFVPESTSTLQ | SEQ ID 37 |
| P58_6 | TIPMFVPESTS | SEQ ID 38 |

A peptide within Formula I, II, III, IV, V, or VI can be provided as part of a longer peptide that includes the specified amino acid sequence. For example, the peptide can be provided on a peptide that is less than 200, 150, 125, 100, 75, 50, 25, 24, 23, 22, 21, 20, 19, 18, or 17 amino acids. The invention additionally provides a peptide fragment having fewer than the amino acid sequences rected Formula I, II, III, IV, V, or VI. In preferred embodiments, the peptide fragment retains one or more of the activities associated with the full-length peptide, e.g., binding to and/or activation of a GPCR receptor, or activity against a condition described herein.

In some embodiments, a peptide within Formula I, II, or III binds a G-protein coupled receptor (GPCR) protein. For example a peptide can bind a MAS1 gene product for a peptide of Formula I or Formula II or a peptide can bind a Mas-related G-protein coupled receptor member X1 (Sensory neuron-specific G-protein coupled receptor 4) for a peptide of Formula III. A peptide can bind a Mas-related G-protein coupled receptor member X2 for a peptide of Formula I, III, IV, V or a peptide can bind a FMLP-related receptor I for a peptide of Formula II, III, IV or VI.

In some embodiments, a peptide within Formula I, II III, IV, V, or VI activates a GPCR protein. Activation of a GPCR protein can be measured using methods known in the art.

A peptide within Formula I, II, III, IV, V, or VI can be provided conjugated to a second peptide or polypeptide. Examples of second peptides or polypeptides are multiple antigenic peptides (MAP) and a signal sequence. Suitable signal sequences include, e.g., MPSVRSLLRLLAAAAAC-GAFA (SEQ ID NO:51), MPSVRSLLRLLAAAAACGA (SEQ ID NO:52); MHWKMLLLLLLYYNAEA (SEQ ID NO:53); MSKSCGNNLAAISVGISLLLLLVVC (SEQ ID NO:54); MAHVPARTSPGPGPQLLLLLLPLFLLLL-RDVAG (SEQ ID NO: 55); and MATASPSVFLLM-VNGQVES (SEQ ID NO: 56).

In some embodiments, the second peptide or polypeptide is an immunoglobulin sequence (e.g., an IgG sequence) Immunoreactive ligands for use as a targeting moiety in the invention include an antigen-recognizing immunoglobulin (also referred to as "antibody"), or antigen-recognizing fragment thereof, e.g., immunoglobulins that can recognize a tumor-associated antigen. As used herein, "immunoglobulin" refers to any recognized class or subclass of immunoglobulins such as IgG, IgA, IgM, IgD, or IgE.

Preferred are those immunoglobulins which fall within the IgG class of immunoglobulins. The immunoglobulin can be derived from any species. Preferably, however, the immunoglobulin is of human, murine, or rabbit origin. In addition, the immunoglobulin may be polyclonal or monoclonal, but is preferably monoclonal.

Conjugates of the invention may include an antigen-recognizing immunoglobulin fragment. Such immunoglobulin fragments may include, for example, the Fab', F (ab')2, Fv or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, *J. Immunology*, 131, 2895, 1983; Lamoyi et al., *J. Immunological Methods*, 56, 235, 1983.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. The terms encompass any peptide (including cyclic peptides) or protein comprising two or more amino acids joined to each other by peptide bonds or modified peptide bonds. "Polypeptide" refers to both short chains, commonly referred to as peptides, oligopeptides or oligomers, and to longer chains, generally referred to as proteins.

"Polypeptides" include amino acid sequences modified either by natural processes, or by chemical modification techniques which are well known in the art. Modifications may occur anywhere in a polypeptide, including the peptide backbone, the amino acid side-chains, and the amino or carboxyl termini. Polypeptides can be modified, e.g., by the addition of carbohydrate residues to form glycoproteins. The terms "polypeptide," "peptide" and "protein" include glycoproteins, as well as non-glycoproteins.

Peptides within the invention can be produced using methods known in the art, e.g., by purifying the peptide sequence from a naturally occurring protein or peptide. Purification can be performed along with a cleavage or degradation (either enzymatic or non-enzymatic) to produce the desired peptide using methods known in the art.

Alternatively, products can be biochemically synthesized using, e.g., solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence).

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Polypeptides or peptides can alternatively be synthesized using recombinant techniques such as those described by Bitter et al., (1987) *Methods in Enzymol.* 153:516-544, Studier et al. (1990) *Methods in Enzymol.* 185:60-89, Brisson et al. (1984) *Nature* 310:511-514, Takamatsu et al. (1987) *EMBO J.* 6:307-311, Coruzzi et al. (1984) *EMBO J.* 3:1671-1680 and Brogli et al., (1984) *Science* 224:838-843, Gurley et al. (1986) *Mol. Cell. Biol.* 6:559-565 and Weissbach & Weissbach, 1988, *Methods for Plant Molecular Biology*, Academic Press, NY, Section VIII, pp 421-463.

A peptide within the invention may include one or more modifications. For example, it may be provided phosphorylated (typically at a serine, threonine, or tyrosine residue), pegylated, coupled to a biotin moiety, or include a disulfide bond to another peptide, polypeptide or amino acid. The peptide may be provided in a cyclic form, e.g., as a cyclic peptide or as a lactam. Alternatively, or in addition, the peptide may be provided as a branched peptide.

The peptide may be additionally modified (when linear) at its amino terminus or carboxy terminus Examples of amino terminal modifications include, e.g., N-glycated, N-alkylated, N-acetylated or N-acylated amino acid. A terminal modification can include a pegylation. An example of a carboxy terminal modification is a c-terminal amidated amino acid.

A peptide of the invention may contain amino acids other than the 20 gene-encoded amino acids. When amino acids are not designated as either D- or L-amino acids, the amino acid is either an L-amino acid or could be either a D- or L-amino acid, unless the context requires a particular isomer.

The notations used herein for the polypeptide amino acid residues are those abbreviations commonly used in the art. The less common abbreviations Abu, Cpa, Nle, Pal, Tle, Dip, 4-Fpa, and Nal stand for 2-amino-butyric acid, p-chlorophenylalanine, norleucine, 3-pyridyl-2-alanine, tert-leucine, 2,2-diphenylalanine, 4-fluoro-phenylalanine, and 3-(2-naphthyl)-alanine or 3-(1-naphthyl)-alanine, respectively.

One example of a non-naturally occurring amino acid is an omega-amino acid, e.g., beta-alanine (beta-Ala), or 3 aminopropionic (3-aP). Other examples are non-naturally occurring amino acids, e.g., sarcosine (Sar), β-alanine (β-Ala), 2,3 diaminopropionic (2,3-diaP) or alpha-aminisobutyric acid (Aib); omega-acid is beta-alanine (beta-Ala), or 3 aminopropionic (3-aP); a hydrophobic non-naturally occurring amino acid, such as t-butylalanine (t BuA), t butylglycine (t BuG), N methylisoleucine (N MeIle), norleucine (Nle), methylvaline (Mvl), cyclohexylalanine (Cha), phenylglycine (Phg), Nal, β2-thienylalanine (Thi), 2 naphthylalanine (2 Nal), or 1,2,3,4-tetrahydroisoquinoline-3 carboxylic acid (Tic); a basic amino acid, such as ornithine (Orn) or homoarginine (Har); and a neutral/polar non-naturally occurring amino acid is citrulline (Cit), Acetyl Lys, or methionine sulfoxide (MSO).

Other non-conventional amino acids are listed in Table 6.

TABLE 6

| Non-conventional amino acid | Code |
|---|---|
| α-aminobutyric acid | Abu |
| α-amino-α-methylbutyrate | Mabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltrytophan | Dmtrp |
| D-α-methyltyrosine | Dmtyr |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |

TABLE 6-continued

| Non-conventional amino acid | Code |
|---|---|
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval |
|  | nbhm |
| N-(N-(2,2-diphenylethyl) carbamylmethyl-glycine | Nnbhm |
| 1-carboxy-1-(2,2-diphenyl ethylamino)cyclopropane | Nmbc |
| L-N-methlylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyl-α-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

Modifications

Fusion Proteins

A fusion protein may be prepared from a peptide according to the present invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein are known in the art, (see for example M. Clark, "Chemical Immunol and Antibody Engineering", pp 1-31 for a description of these mutations and their effect). The construct for the Fc chain which features such changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331 proline for serine may block the ability to activate complement, which may optionally be considered an undesired function (see M. Clark, "Chemical Immunol and Antibody Engineering", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al. vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Addition of Groups

If a peptide according to the present invention is a linear molecule, it is possible to place various functional groups at various points on the linear molecule which are susceptible to or suitable for chemical modification. Functional groups can be added to the termini of linear forms of the peptide. In some embodiments, the functional groups improve the activity of the peptide with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are optionally independently an aliphatic, substituted aliphatic, benzyl, substituted benzyl, aryl or a substituted aryl group. In addition, taken together with the nitrogen atom, R$_2$ and R$_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native peptide protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, *Tetrahedron Lett.* 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

Exemplary, illustrative but non-limiting non-natural amino acids include beta-amino acids (beta3 and beta2), homoamino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a peptide may optionally be chemically modified, i.e. changed by addition of functional groups. For example the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Covalent modifications of the peptides of the present invention are included within the scope of this invention. Other types of covalent modifications of the peptides are introduced into the molecule by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyepropionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125 I or 131 I to prepare labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking CHF to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

Altered Glycosylation

Peptides of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to peptides of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on peptides of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

By "variant" is meant a polypeptide that differs from a reference polypeptide, but retains essential properties. Generally, differences are limited so that the sequences of the reference polypeptide and the variant are closely similar overall and, in many regions, identical. A variant and reference polypeptide may differ in amino acid sequence by one or more substitutions, additions, and/or deletions, in any combination. A substituted or inserted amino acid residue may or may not be one encoded by the genetic code. A variant of a polypeptide may be a naturally occurring such as an allelic variant, or it may be a variant that is not known to occur naturally. Non-naturally occurring variants of polypeptides may be made by mutagenesis techniques or by direct synthesis.

Generally, the variant differs from the reference polypeptide by conservative amino acid substitutions, whereby a residue is substituted by another with like characteristics (e.g. acidic, basic, aromatic, etc.). Typical substitutions are among Ala, Val, Leu and Ile; among Ser and Thr; among the acidic residues Asp and Glu; among Asn and Gln; and among the basic residues Lys and Arg; or aromatic residues Phe and Tyr.

Antibodies to Bioactive Peptides

The invention also includes an antibody to a bioactive peptide disclosed herein, or a fragment of the bioactive peptide. In some embodiments, the bioactive peptide is a GPCR ligand.

"Antibody" refers to a polypeptide ligand substantially encoded by an immunoglobulin gene or immunoglobulin genes, or fragments thereof, which specifically binds and recognizes an epitope (e.g., an antigen). The antibody can be provided as, e.g., an intact immunoglobulin or as fragment, e.g., a fragment produced by digestion with various peptidases. This includes, e.g., Fab' and F(ab)'$_2$ Fv (defined as a genetically engineered fragment containing the variable region of the light chain and the variable region of the heavy chain expressed as two chains); and (5) Single chain antibody ("SCA"), a genetically engineered molecule containing the variable region of the light chain and the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies. It includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

Antibodies are raised against, e.g., an epitope in a peptide of Formula I, II III, IV, V, or VI. In some embodiments, anti-GPCR peptide ligand antibodies are raised against FLGYCIYLNRKRRGDPAFKRRLRD monomer or dimer (SEQ ID NO. 9)
FLGYSIYLNRKRRGDPAFKRRLRD (SEQ ID NO. 10)
IYLNRKRRGDPAFKRRLRD (SEQ ID NO. 11)
FAFLGYSIYLNRKRRGDPAF (SEQ ID NO. 12)
FAFLGYCIYLNRKRRGDPAF monomer or dimer (SEQ ID NO. 13)
FAFLGYSIYLN (SEQ ID NO. 18)
FAFLGYCIYLN monomer or dimer (SEQ ID NO. 19)
FAFLGYCIYLNRKRRGDPAFKRRLRD (SEQ ID NO. 20)
FLGYCIYLN (SEQ ID NO. 21)
FLGYCIYLNR (SEQ ID NO. 22)
FLGYCIYLNRKRRGDPAF (SEQ ID NO. 23)
RGDPAF (SEQ ID NO. 24)
RRGDPAF (SEQ ID NO. 25)
GDPAFKRRLRD (SEQ ID NO. 28)
GDPAF (SEQ ID NO. 29)
IYLN (SEQ ID NO. 30)
IYLNRKRRGDPAF (SEQ ID NO. 31)
SMCHR SRAVLFPAAHRP—monomer or dimer (SEQ ID NO. 6)
SMVHRWSRAVLFPAAHRP (SEQ ID NO. 7)
RWSRAVLFPAAHRP (SEQ ID NO. 14)
HRWSRAVLFPAAHRP (SEQ ID NO. 15)
WSRAVLFPAAHRP (SEQ ID NO. 16)
AVLFPAAHRP (SEQ ID NO. 27)
GIGSVWHWKHRVATRFTLPRFLQ (SEQ ID NO. 8)
GIGCVWHWKHRVATRFTLPRFLQ (SEQ ID NO. 39)
GIGCVWHWKHRVATRFTLPRFLQRR (SEQ ID NO. 40)
GIGCVWHWKHRVATRFTLPRFLQRSS (SEQ ID NO. 41)
GIGCVWHWKHRVATRFTLPRFLQRSSR (SEQ ID NO. 42)
IGCVWHWKHRVATRFTLPRFLQ (SEQ ID NO. 43)
IGCVWHWKHRVATRFTLPRFLQRR (SEQ ID NO. 44)
IGCVWHWKHRVATRFTLPRFLQRSS (SEQ ID NO. 45)
IGCVWHWKHRVATRFTLPRFLQRSSR (SEQ ID NO. 46)
CVWHWKHRVATRFTLPRFLQ (SEQ ID NO. 47)
CVWHWKHRVATRFTLPRFLQRR (SEQ ID NO. 48)
CVWHWKHRVATRFTLPRFLQRSS (SEQ ID NO. 49)
CVWHWKHRVATRFTLPRFLQRSSR (SEQ ID NO. 50)
AAQATGPLQDNELPGLDERPPRAHAQHFHKHQLWPSPFRALKPRP (SEQ ID NO. 5)
AAQATGPLQDNELPGLDERPP (SEQ ID 32)
AAQATGPLQDNELPGLDERPPRAHAQHFH (SEQ ID NO. 33)
PPRAHAQHFHKHQLWPSPFRALKPRP (SEQ ID NO. 34)
HQLWPSPFRALKPRP (SEQ ID NO.35)
AHAQHFHKHQLWPSPFRALKPRP (SEQ ID NO. 17)
TIPMFVPESTSKLQKFTSWFM (SEQ ID NO. 1)
FTSWFM (SEQ ID NO. 2)
LQKFTSWFM (SEQ ID NO. 3)
TIPMFVPESTSTLQKFTSWFM (SEQ ID NO. 4)
HKRTIPMFVPESTSKLQKFTSWFM (SEQ ID NO. 26)
TIPMFVPESTSKLQ (SEQ ID NO. 36)
TIPMFVPESTSTLQ (SEQ ID NO. 37)
TIPMFVPESTS (SEQ ID NO. 38)

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods.

The bioactive peptide antibody can additionally be provided as a peptide coding corresponding a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [*Methods*, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321: 522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

The antibody preferably binds specifically (or selectively) to a GPCR peptide ligand. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

If desired, the antibody can be provided conjugated or coupled to a detectable label, a radioactive label, an enzyme, a fluorescent label, a luminescent label, a bioluminescent label, or a therapeutic agent.

Methods of Treatment

According to an additional aspect of the present invention there is provided a method of treating disease, disorder or condition, as described hereinabove, in a subject.

The subject according to the present invention is a mammal, preferably a human which is diagnosed with one of the disease, disorder or conditions described hereinabove, or alternatively is predisposed to at least one type of disease, disorder or conditions described hereinabove.

As used herein the term "treating" refers to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the polypeptides of the present invention in the subject.

Optionally, upregulation may be effected by administering to the subject at least one of the polypeptides of the present invention (e.g., recombinant or synthetic) or an active portion thereof, as described herein. The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy). Thus, treatment of malignancies using the agents of the present invention may be combined with, for example, radiation therapy, antibody therapy and/or chemotherapy.

Alternatively or additionally, an upregulating method may optionally be effected by specifically upregulating the amount (optionally expression) in the subject of at least one of the polypeptides of the present invention or active portions thereof.

Upregulating expression of the therapeutic peptides of the present invention may be effected via the administration of at least one of the exogenous polynucleotide sequences of the present invention, ligated into a nucleic acid expression construct designed for expression of coding sequences in eukaryotic cells (e.g., mammalian cells). Accordingly, the exogenous polynucleotide sequence may be a DNA or RNA sequence encoding the peptides of the present invention or active portions thereof.

It will be appreciated that the nucleic acid construct can be administered to the individual employing any suitable mode of administration including in vivo gene therapy (e.g., using viral transformation as described hereinabove). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Such cells (i.e., which are transfected with the nucleic acid construct of the present invention) can be any suitable cells, such as kidney, bone marrow, keratinocyte, lymphocyte, adult stem cells, cord blood cells, embryonic stem cells which are derived from the individual and are transfected ex vivo with an expression vector containing the polynucleotide designed to express the polypeptide of the present invention as described hereinabove.

Administration of the ex vivo transfected cells of the present invention can be effected using any suitable route such as intravenous, intra peritoneal, intra kidney, intra gastrointestinal track, subcutaneous, transcutaneous, intramuscular, intracutaneous, intrathecal, epidural and rectal. According to presently preferred embodiments, the ex vivo transfected cells of the present invention are introduced to the individual using intravenous, intra kidney, intra gastrointestinal track and/or intra peritoneal administrations.

The ex vivo transfected cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

Pharmaceutical Compositions and Delivery Thereof

The bioactive peptide ligand is typically provided in a pharmaceutically acceptable carrier suitable for administering the pharmaceutical composition to a human patient. As would be appreciated by one of skill in this art, the carriers may be chosen based on the route of administration as described below, the location of the target issue, the drug being delivered, the time course of delivery of the drug, etc.

The term "pharmaceutically acceptable carrier" means a non-toxic, inert solid, semi-solid or liquid filler, diluent, encapsulating material or formulation auxiliary of any type. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), A. Gennaro, 1990, Mack Publishing Company, Easton, Pa. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

By "pharmaceutically acceptable salt" is meant non-toxic acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

The pharmaceutical compositions can be administered to a patient by any means known in the art including oral and parenteral routes. The term "patient", as used herein, refers to humans as well as non-humans, including, for example, mammals, birds, reptiles, amphibians and fish. Preferably, the non-humans are mammals (e.g., a rodent (including a mouse or rat), a rabbit, a monkey, a dog, a cat, sheep, cow, pig, horse). The non-human animal could alternatively be a bird, e.g., a chicken or turkey.

In certain embodiments parenteral routes are preferred since they avoid contact with the digestive enzymes that are found in the alimentary canal. According to such embodiments, inventive compositions including a therapeutic agent may be administered by injection (e.g., intravenous, subcutaneous or intramuscular, intraperitoneal injection), rectally, vaginally, topically (as by powders, creams, ointments, or drops), or by inhalation (as by sprays), intranasal, pulmonary, or intrabuccal.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, a therapeutic agent is suspended in a carrier fluid comprising 1% (w/v) sodium carboxymethyl cellulose and 0.1% (v/v) TWEEN80™. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the therapeutic agent with suitable non-irritating excipients or carriers such as cocoa butter, polyethylene glycol, or a suppository wax which are solid at ambient temperature but liquid at body temperature and therefore melt in the rectum or vaginal cavity and release the therapeutic agent.

Dosage forms for topical or transdermal administration of a pharmaceutical composition including a therapeutic agent include ointments, pastes, creams, lotions, gels, powders, solutions, sprays, inhalants, or patches. The therapeutic agent is admixed under sterile conditions with a pharmaceutically acceptable carrier and any needed preservatives or buffers as may be required. Ophthalmic formulations, ear drops and eye drops are also contemplated as being within the scope of this invention. The ointments, pastes, creams and gels may contain, in addition to the therapeutic agents of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Transdermal patches have the added advantage of providing controlled delivery of a compound to the body. Such dosage forms can be made by dissolving or dispensing the therapeutic agents in a proper medium. Absorption enhancers can also be used to increase the flux of the compound across the skin. The rate can be controlled by either providing a rate controlling membrane or by dispersing the therapeutic agents in a polymer matrix or gel.

Powders and sprays can also contain excipients such as lactose, talc, silicic acid, aluminum hydroxide, calcium silicates and polyamide powder, or mixtures of these drugs. Sprays can additionally contain customary propellants such as chlorofluorohydrocarbons.

When administered orally, the therapeutic agent is optionally encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al., *Reactive Polymers* 6:275, 1987; Mathiowitz et al., *J. Appl. Polymer Sci.* 35:755, 1988; Langer *Acc. Chem. Res.* 33:94, 2000; Langer *J. Control. Release* 62:7, 1999; Uhrich et al., *Chem. Rev.* 99:3181, 1999; Zhou et al., *J. Control. Release* 75:27, 2001; and Hanes et al., *Pharm. Biotechnol.* 6:389, 1995). For example, the therapeutic agent can be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters) and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups and elixirs. In addition to an encapsulated or unencapsulated therapeutic agent, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants, wetting agents, emulsifying and suspending agents, sweetening, flavoring and perfuming agents. As used herein, the term "adjuvant" refers to any compound which is a nonspecific modulator of the immune response. In certain preferred embodiments, the adjuvant stimulates the immune response. Any adjuvant may be used in accordance with the present invention. A large number of adjuvant compounds are known in the art (Allison, *Dev. Biol. Stand.* 92:3, 1998; Unkeless et al., *Annu. Rev. Immunol.* 6:251, 1998; and Phillips et al., *Vaccine* 10: 151, 1992).

Solid dosage forms for oral administration include capsules, tablets, pills, powders and granules. In such solid dosage forms, the encapsulated or unencapsulated therapeutic agent is mixed with at least one inert, pharmaceutically acceptable excipient or carrier such as sodium citrate or dicalcium phosphate and/or (a) fillers or extenders such as starches, lactose, sucrose, glucose, mannitol and silicic acid, (b) binders such as, for example, carboxymethylcellulose, alginates, gelatin, polyvinylpyrrolidinone, sucrose and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art.

The exact dosage of the therapeutic agent is chosen by the individual physician in view of the patient to be treated. In general, dosage and administration are adjusted to provide an effective amount of the therapeutic agent to the patient being treated. As used herein, the "effective amount" of an therapeutic agent refers to the amount necessary to elicit the desired biological response. As will be appreciated by those of ordinary skill in this art, the effective amount of therapeutic agent may vary depending on such factors as the desired biological endpoint, the drug to be delivered, the target tissue, the route of administration, etc. For example, the effective amount of therapeutic agent containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

The therapeutic agents of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compositions of the present invention will be decided by the attending physician within the scope of sound medical judgment. For any therapeutic agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of therapeutic agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies is used in formulating a range of dosage for human use.

If several different therapeutic modalities (e.g., with different therapeutic agents) are to be administered simultaneously then they may be combined into a single pharmaceutical composition. Alternatively, they may be prepared as separate compositions that are then mixed or simply administered one after the other. If several different therapeutic agents (e.g., with different therapeutic agents) are to be administered at different times then they are preferably prepared as separate compositions. If additional drugs are going to be included in a combination therapy they can be added to one or more of these therapeutic agents or prepared as separate compositions.

A peptide could be chemically modified in order to alter its properties such as biodistribution, pharmacokinetics and solubility. Various methods have been used to increase the solubility and stability of drugs, among them the use of organic solvents, their incorporation within emulsions or liposomes, the adjustment of pH, their chemical modifications and their complexation with the cyclodextrins. The cyclodextrins are oligosacharides cyclic family, which include six, seven or eight units of glucopyranose. Due to sterics interactions, the cyclodextrins form a cycle structure in the shape of a cone with an internal cavity. Those are compounds chemically stable that can be modified. The cyclodextrins hosts form complexes with various hydrophobic guests in their cavity. The cyclodextrins are used for the solubilization and encapsulation of drugs.

Liposomes and controlled release:

In order to design a drug delivery system, various kinds of high performance carrier materials are being developed to deliver the necessary amount of drug to the targeted site for a necessary period of time, both efficiently and precisely.
Cyclodextrins, biodegradable or non biodegradable polymers, liposomes, emulsions. Multiple emulsions are potential candidates for such a role, because of their ability to alter physical, chemical and biological properties of guest molecules.
There are number of drug delivery systems including but not limited to polymer microcapsules, microparticles, nanoparticles, liposomes and emulsion. Many of these are prepared from synthetic biodegradable polymers such as polyanhydrides and poly hydroxy acids. In these systems the drugs incorporate in polymeric microspheres, which release the drug inside the organism in small and controlled daily doses during days months or until years.

Several polymers already were tested in controlled release systems. Such as: polyuretans for its elasticity, polysiloxans or silicons for being a good one insulating, polymethylmetacrilate for its physical form; polyvinylalcohol for its hydrofobicity and resistance, polyethylene for its hardness and impermeability (Gilding, D. K. Biodegradable polymers. Biocompat. Clin. Impl Mater. 2:209-232, 1981). Biodegradable polymers and biocompatible polymers, have been extensively investigated as vehicle for controlled release systems due to their ability to undergo surface degradation. These kind of polymers can be chose from: poly(2-hydroxiethylmetacrilate), polyacrilamide, polymer from lactic acid (PLA), from glicolic acid (PGA), and the respective ones co-polymers, (PLGA) and the poly(anidrides), as described by Tamada and Langer, J. Biomater. Sci. Polym. Edn, 3(4):315-353.

Suitable controlled release vehicles include, but are not limited to, biocompatible polymers, other polymeric matrices, capsules, microcapsules, nanocapsules, microparticles, nanoparticles, bolus preparations, osmotic pumps, diffusion devices, liposomes, lipospheres and transdermal delivery systems, implantable or not.

Satisfactory systems of controlled release include, but are not limited to, the ciclodextrines, biocompatible polymers, biodegradable polymers, other polymeric matrixes, capsules, micro-capsules, microparticles, bolus preparations, osmotic pumps, diffusion devices, lipossomes, lipoesferes, and systems of transdermic administration. Other compositions of controlled release include liquids that, when submitted the temperature changes, form a solid or a gel in situ.

Liposomes are lipid vesicles that include aqueous internal compartments in which molecules, for example drugs, are encapsulated with the objective of reaching a controlled release of the drug after administration in individuals. Many different techniques have been proposed for the preparation of liposomes [U.S. Pat. No. 4,552,803, Lenk; U.S. Pat. No. 4,310,506, Baldeschwieler; U.S. Pat. No. 4,235,871, Papahadjopoulos; U.S. Pat. No. 4,224,179, Schneider; U.S. Pat. No. 4,078,052, Papahadjopoulos; U.S. Pat. No. 4,394,372, Tailor; U.S. Pat. No. 4,308,166, Marchetti; U.S. Pat. No. 4,485,054, Mezei; and U.S. Pat. No. 4,508,703, Redziniak; Woodle and Papahadjopoulos, Methods Enzymol. 171:193-215 (1989]; Unilamellar vesicles display a single membrane [Huang, Biochemistry 8:334-352 (1969] while muitilamellar vesicles (MLVs) have numerous concentric membranes [Bangham et al., J. Mol. Biol. 13:238-252 (1965]. The procedure of Bangham [J. Mol. Biol. 13:238-252 (1965] produces "ordinary MLVs", that present unequal solute distributions among the aqueous compartments and, consequently, differences of osmotic pressure. Lenk et al. (U.S. Pat. No. 4,522,803; U.S. Pat. No. 5,030,453 and U.S. Pat. No. 5,169,637), Fountain et al. (U.S. Pat. No. 4,588,578), Cullis et al. (U.S. Pat. No. 4,975,282) and Gregoriadis et al. (Pat. W.O. 99/65465) introduced methods for the preparation of MLVs that present substantially equal solute distributions among the compartments. Similar solute distributions among the different compartments mean a larger drug encapsulation efficiency as well as smaller differences of osmotic pressure that turns these MLVs more stable than ordinary MLVs. Unilamellar vesicles can be produced by sonication of MLVs [Papahadjopoulos et al. (1968)] or by extrusion through polycarbonate membranes [Cullis et al. (U.S. Pat. No. 5,008,050) and Loughrey et al. (U.S. Pat. No. 5,059,421)].

Satisfactory lipids include for example, phosphatidylcholine, phosphatidylserine, phosphatidylglycerol, cardiolipin, cholesterol, phosphatidic acid, sphingolipids, glycolipids, fatty acids, sterols, phosphatidylethanolamine, polymerizable lipids in their polymerized or non-polymerized form, mixture of these lipids.

The composition of the liposomes can be manipulated such as to turn them specific for an organ or a cell type. The targeting of liposomes has been classified either on the basis of anatomical factors or on the basis of the mechanism of their interaction with the environment. The anatomical classification is based on their level of selectivity, for example, organ-specific or cell-specific. From the point of view of the mechanisms, the-targeting can be considered as passive or active.

The passive targeting exploits the natural tendency of conventional liposomes to be captured by the cells of the reticuloendothelial system, i.e. mainly the fixed macrophages in the liver, spleen and bone marrow.

Sterically stabilized liposomes (also well-known as "PEG-liposomes") are characterized by a reduced rate of elimination from the blood circulation [Lasic and Martin, Stealth Liposomes, CRC Press, Inc., Boca Raton, Fla. (1995)].

PEG-liposomes present a polyethylene glycol polymer conjugated to the head group of some phospholipid that reduces their interaction with plasma proteins, such as opsonins, and reduces the rate of their uptake by cells. The resulting steric barrier allows these liposomes to remain for a longer period of time within the circulation than conventional liposomes [Lasic and Martin, Stealth Liposomes, CRC Press, Inc., Boca Raton, Fla. (1995); Woodle et al., Biochim. Biophys. Acta 1105:193-200 (1992); Litzinger et al., Biochim Biophys. Acta 1190:99-107 (1994); Bedu Addo, et al., Pharm. Res. 13:718-724 (1996]. The drug encapsulation within PEG-liposomes has resulted in the improvement of the effectiveness of many chemotherapeutic agents [Lasic and Martin, Stealth liposomes, CRC Press, Inc., Boca Raton, Fla. (1995)] and bioactive peptides [Allen T. M. In: Liposomes, New Systems, New Trends in their Applications (F. Puisieux, P. Couvreur, J. Delattre, J.-P. Devissaguet Ed.), Editions de la Sante, France, 1995, pp. 125].

Studies in this area demonstrated that different factors affect the effectiveness of PEG-liposomes. Ideally, the diameter of the vesicles should be below 200 nm, the number of units in PEG of approximately 2.000 and the proportion of Pegylated lipid from 3 to 5 mol % [Lasic and Martin, Stealth Liposomes, CRC Press, Inc., Boca Raton, Fla. (1995); Woodle et al., Biochim. Biophys. Acta 1105:193-200 (1992); Litzinger et al., Biochim. Biophys. Acta 1190:99-107 (1994); Bedu Addo et al., Pharm. Res. 13:718-724 (1996)].

The active targeting involves alteration of liposomes through their association with a ligand, such as a monoclonal antibody, a sugar, a glycolipid, protein, a polymer or by changing the lipid composition or the liposome size to target them to organs and cells different from those which accumulate conventional liposomes.

Mucosal Delivery Enhancing Agents

"Mucosal delivery enhancing agents" are defined as chemicals and other excipients that, when added to a formulation comprising water, salts and/or common buffers and peptide within the present invention (the control formulation) produce a formulation that produces a significant increase in transport of peptide across a mucosa as measured by the maximum blood, serum, or cerebral spinal fluid concentration (Cmax) or by the area under the curve, AUC, in a plot of concentration versus time. A mucosa includes the nasal, oral, intestional, buccal, bronchopulmonary, vaginal, and rectal mucosal surfaces and in fact includes all mucus-secreting membranes lining all body cavities or passages that communicate with the exterior. Mucosal delivery enhancing agents are sometimes called carriers.

Compositions and Methods of Sustained Release

The present invention provides improved mucosal (e.g., nasal) delivery of a formulation comprising the peptide within the present invention in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration (Cmax) to enhance the therapeutic activity of mucosally-administered peptide. A second factor affecting therapeutic activity of the peptide in the blood plasma and CNS is residence time (RT). Sustained release-enhancing agents, in combination with intranasal delivery-enhancing agents, increase Cmax and increase residence time (RT) of the peptide. Polymeric delivery vehicles and other agents and methods of the present invention that yield sustained release-enhancing formulations, for example, polyethylene glycol (PEG), are disclosed herein. Within the mucosal delivery formulations and methods of the invention, the peptide is frequently combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the U.S. Pharmacopeia National Formulary, 1857-1859, (1990). As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of the peptide or other biologically active compound(s). Within certain aspects of the invention, absorption-promoting agents for coordinate administration or combinatorial formulation with the peptide of the invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the peptide. In additional aspects, surfactants (e.g., polysorbates) are employed as adjunct compounds, processing agents, or formulation additives to enhance intranasal delivery of the peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the peptide from the vehicle into the mucosa. The mucosal therapeutic and prophylactic compositions of the present invention may be supplemented with any suitable penetration-promoting agent that facilitates absorption, diffusion, or penetration of the peptide across mucosal barriers. The penetration promoter may be any promoter that is pharmaceutically acceptable.

Charge Modifying and pH Control Agents and Methods

To improve the transport characteristics of biologically active agents (including the peptide within the present invention), for enhanced delivery across hydrophobic mucosal membrane barriers, the invention also provides techniques and reagents for charge modification of selected biologically active agents or delivery-enhancing agents described herein. In this regard, the relative permeabilities of macromolecules is generally be related to their partition coefficients. The degree of ionization of molecules, which is dependent on the pKa of the molecule and the pH at the mucosal membrane surface, also affects permeability of the molecules. Permeation and partitioning of biologically active agents, including the peptide within the present invention, for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent. Consistent with these general teachings, mucosal delivery of charged macromolecular species, including the peptide within the present invention is substantially improved when the active agent is delivered to the mucosal surface in a substantially un-ionized, or neutral, electrical charge state.

Certain peptide and protein components of mucosal formulations for use within the invention will be charge modified to yield an increase in the positive charge density of the peptide or protein. These modifications extend also to cationization of peptide and protein conjugates, carriers and other delivery forms disclosed herein.

Degradative Enzyme Inhibitory Agents and Methods

Another excipient that may be included in a trans-mucosal preparation is a degradative enzyme inhibitor. Any inhibitor that inhibits the activity of an enzyme to protect the biologically active agent(s) may be usefully employed in the compositions and methods of the invention. Useful enzyme inhibitors for the protection of biologically active proteins and peptides include, for example, soybean trypsin inhibitor, pancreatic trypsin inhibitor, chymotrypsin inhibitor and trypsin and chrymotrypsin inhibitor isolated from potato (*solanum tuberosum* L.) tubers. A combination or mixtures of inhibitors may be employed. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation. Additional enzyme inhibitors for use within the invention are selected from a wide range of non-protein inhibitors that vary in their degree of potency and toxicity. As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors for use within the invention are organophosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). Yet another type of enzyme inhibitory agent for use within the methods and compositions of the invention are amino acids and modified amino acids that interfere with enzymatic degradation of specific therapeutic compounds.

The therapeutic agents of the invention can be used to treat disorders for which modulation of GPCR-related signal transduction pathways is efficacious. For example, the peptides of the invention falling within Formulas II, IV, and VI are used to treat disorders for which modulation of FPLR1 is efficacious. Examples of such peptides are depicted in SEQ ID NOs: 1-7, 14-16, 26-27, 32-38. These peptides are used to treat any disease or condition that involves neutrophil (polymorphonuclear leukocyte, PMN)-dependent damage or neutrophil regulation. The peptides of the invention are also used to treat disorders associated with TNFα-initiated cytokine activity in a subject.

The peptides of the invention falling within Formulas I, III, IV and V are used to treat disorders for which modulation of MrgX2 is efficacious. Examples of such peptides are depicted in SEQ ID NOs: 5, 8-13, 17-25, 28-35, 39-50. The peptides of the invention falling within Formula III are used to treat disorders for which modulation of MrgX1 is efficacious. Examples of such peptides are depicted in SEQ ID NOs: 8, 39-50. The peptides of the invention falling within Formulas I and II are also used to treat disorders for which modulation of Mas is efficacious. Examples of such peptides are depicted in SEQ ID NOs:6-7, 9-16, 18-25, 27-31.

The peptides of the invention falling within Formulas I, II, III, IV, V and VI, such as for example, peptides as depicted in SEQ ID NOs: 1-50, are useful for the treatment of inflammatory diseases including but not limited to gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

The peptides of the invention falling within Formulas I, II, III, IV, V and VI, such as for example, peptides as depicted in SEQ ID NOs:1-50, are also useful for the treatment of fibrotic conditions involving tissue remodeling following inflammation or ischemia-reperfusion injury, including but not limited to endomyocardial fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis); fibromatosis; granulomatous lung disease; and glomerulonephritis The peptides of the invention falling within Formulas I, II, IV, and VI, such as for example, peptides as depicted in SEQ ID NOs:1-7, 9-16, 18-38, are also useful in the treatment of autoimmune disease, including but not limited to multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

The peptides of the invention falling within Formulas I, II, IV, and VI, such as for example, peptides as depicted in SEQ ID NOs: 1-7, 9-16, 18-38, are also useful in treating cardiovascular diseases and their complications, peripheral vascular diseases and coronary artery diseases, including but not limited to myocardial infarction; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; or platelet aggregation.

The peptides of the invention falling within Formulas I, II, IV, and VI, such as for example, peptides as depicted in SEQ ID NOs: 1-7, 9-16, 18-38, are useful in treating ischemia-reperfusion injury associated with ischemic and post-ischemic events in organs and tissues, including but not limited to thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation.

The peptides of the invention falling within Formulas I, II, IV, and VI, such as for example, peptides as depicted in SEQ ID NOs: 1-7, 9-16, 18-38, are useful in treating ischemia-reperfusion injury following conditions including but not limited to procedures such as cardiac surgery; organ surgery; organ transplantation; angiography; cardiopulmonary and cerebral resuscitation.

The peptides of the invention falling within Formulas I, II, IV, and VI, such as for example, peptides as depicted in SEQ ID NOs: 1-7, 9-16, 18-38, are useful in the inhibition of alopecia, such as chemotherapy-induced alopecia; and treatment of bone disease, such as osteoporosis.

In another aspect, the peptides of the invention falling within Formulas I, II, III, IV, and V, such as for example, peptides as depicted in SEQ ID NOs:5-25, 27-35, 39-50, are used for prevention and treatment of hypertension and its complications including but not limited to hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; preeclampsia; Raynaud's phenomenon; erectile dysfunction and glaucoma. These peptides are also used as a vasodilator and in antithrombotic therapy.

The peptides of the invention falling within Formulas I, II, IV, and VI, such as for example, peptides as depicted in SEQ ID NOs: 1-7, 9-16, 18-38, are also useful in treating inflammatory conditions associated with an infection, e.g., a bacterial infection or a viral infection, including but not limited to a viral infection caused by human immunodeficiency virus I (HIV-1) or HIV-2, acquired immune deficiency (AIDS), West Nile encephalitis virus, coronavirus, rhinovirus, influenza virus, dengue virus, hemorrhagic fever; an otological infection; severe acute respiratory syndrome (SARS), sepsis and sinusitis.

The peptides of the invention falling within Formulas I, II, IV, and VI, such as for example, peptides as depicted in SEQ ID NOs: 1-7, 9-16, 18-38, are also useful in the prevention or treatment of cancer, or inflammation associated with cancer such as solid cancer, including but not limited to colon cancer, lung cancer, breast cancer, prostate cancer, brain cancer, pancreatic cancer, ovarian cancer or kidney cancer. The cancer can alternatively be a melanoma, glioma, a sarcoma, a leukemia, or lymphoma. These peptides are also useful in the prevention or treatment of invasive and metastatic cancer.

The peptides of the invention falling within Formulas I and II, such as for example, peptides as depicted in SEQ ID NOs:6-7, 9-16, 18-25, 27-31, are used in the prevention and treatment of diseases that involve reduction of oxygen reactive species with consequent endothelial dysfunction, including but not limited to cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

In another aspect, the peptides of the invention falling within Formulas I and II, such as for example, peptides as depicted in SEQ ID NOs:6-7, 9-16, 18-25, 27-31, are used in the prevention and/or treatment of organic alterations produced by aging and as ergogenic aids.

The peptides of the invention falling within Formulas I and II, such as for example, peptides as depicted in SEQ ID NOs:6-7, 9-16, 18-25, 27-31, are used in the prevention and treatment of diseases that involve alterations in the muscular differentiation, maturation and regeneration in muscular atrophies, including but not limited to as cachexia; prolonged restriction to bed due to numerous factors; chronic use of corticoids; and varied neurological syndromes, traumatisms and degenerative diseases that lead to muscular atrophy. The peptides of the invention are used for the prevention or treatment of organic alterations produced by aging and as ergogenic aids.

The peptides of the invention falling within Formulas I, II, IV and VI, such as for example, peptides as depicted in SEQ ID NOs: 1-7, 9-16, 18-38, are used for the prevention and treatment in skin injuries, including but not limited to dermal repair, wound healing; burns, erythemas, lesions, and skin tumors.

The peptides of the invention falling within Formulas I, II, IV and VI, such as for example, peptides as depicted in SEQ ID NOs: 1-7, 9-16, 18-38, are used for the prevention or treatment of immune related conditions including but not limited to graft versus host disease; transplant rejection, bone marrow transplantation.

The peptides of the invention falling within Formulas II, IV and VI, such as for example, peptides as depicted in SEQ ID NOs:1-7, 14-16, 26-27, 32-38, are used for mobilization, activation or inducing chemoattraction of blood cells to a site of injury. The blood cells can include platelets, phagocytes, monocytes, macrophages, eosinophils, neutrophils, and/or lymphocytes.

The peptides of the invention falling within Formulas I and II, such as for example, peptides as depicted in SEQ ID NOs:6-7, 9-16, 18-25, 27-31, are used for prevention or treatment of genetic polymorphism consequent diseases such as the DD type of the angiotensin converting enzyme; type I and type II diabetes mellitus and complications; diabetic mellitus prophylaxis; diabetic maculopathy; and diabetic nephropathy.

The peptides of the invention falling within Formulas I and II, such as for example, peptides as depicted in SEQ ID NOs:6-7, 9-16, 18-25, 27-31, are used in the prevention or treatment of a urogenital disorder or a genitor-urological disorders including but not limited to renal disease; a bladder disorder; disorders of the reproductive system; gynecologic disorders; urinary tract disorder; incontinence; disorders of the male (spermatogenesis, spermatic motility), and female reproductive system; sexual dysfunction; erectile dysfunction; embryogenesis; and pregnancy related disorders. These are also used in pregnancy monitoring.

The peptides of the invention falling within Formulas I, II, IV and VI, such as for example, peptides as depicted in SEQ ID NOs: 1-7, 9-16, 18-38, are used in the prevention or treatment of a cytopenia, including but not limited to a multilineage cytopenia, a thrombocytopenia, anemia, anemia due to renal failure; lymphopenia, leucopenia, neutropenia, radio/chemotherapy-related neutropenia; and platelet disorders.

The invention also provides peptides falling within Formulas I, II, IV and VI, such as for example, peptides as depicted in SEQ ID NOs: 1-7, 9-16, 18-38, that are used in the prevention or treatment of respiratory diseases, including but not limited to asthma, bronchial disease, lung diseases, chronic obstructive pulmonary disease (COPD), Acute Respiratory Distress Syndrome (ARDS), severe acute respiratory syndrome (SARS)

The invention also provides peptides falling within Formulas I, II, IV, and VI, such as for example, peptides as depicted in SEQ ID NOs: 1-7, 9-16, 18-38, that are used in the prevention or treatment of metabolic disorders including but not limited to diabetes, diabetis mellitus, lipodystrophy, hyperthyroidism, glaucoma, hyperlipidaemia, non-insulin dependent diabetes, appetite control and obesity.

The peptides of the invention falling within Formulas I, II, III, IV, and V, such as for example, peptides as depicted in SEQ ID NOs:5-25, 27-35, 39-50, are also used in the prevention and treatment of kidney diseases including but not limited to diabetic nephropathy; glomerulosclerosis; nephropathies; renal impairment; scleroderma renal crisis and chronic renal failure. These peptides can also be used as antidiuretics.

The peptides of the invention falling within Formulas I and II, such as for example, peptides as depicted in SEQ ID NOs:6-7, 9-16, 18-25, 27-31, are also used in the prevention and treatment of blood diseases including but not limited to angioplasty (endoluminal prosthesis and post angioplasty restenosis); haematopoiesis; erythrocytosis; disorders of the blood crasis, such as post radiotherapy.

The peptides of the invention falling within Formulas I, II, IV, and VI, such as for example, peptides as depicted in SEQ ID NOs: 1-7, 9-16, 18-38, are also used in the prevention and treatment of angiogenesis related conditions including but not limited to retinal angiogenesis in a number of human ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

The peptides of the invention falling within Formulas I, II, III, IV, and V, such as for example, peptides as depicted in SEQ ID NOs:5-25, 27-35, 39-50, are also used to treat a central nervous system (CNS) disorder, including but not limited to central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, locomotor activity and a peripheral nervous system disorder.

The peptides of the invention falling within Formulas I, III, IV, and V, such as for example, peptides as depicted in SEQ ID NOs:5, 8-13, 17-25, 28-35, 39-50, are also used to treat and control pain including but not limited to complex regional pain, muscoskeletal pain, neuropathic pain, post-herpetic pain, pain associated with cancer, or post-operative pain.

Compounds of Formula I, II, III, IV, V, or VI can be used to treat disorders, diseases and/or conditions as described herein, by administering to a subject in need thereof a therapeutically effective amount of a peptide falling within Formula I, II, III, IV, V, or VI.

Also provided by the invention is a method of treating disorders for which modulation of GPCR-related signal transduction pathways is efficacious. For example, provided by the invention is a method of treating disorders for which modulation of FPLR1 is efficacious in a subject by administering to a subject in need thereof a therapeutically effective amount of a compound falling within Formulas II, IV, and VI, such as for example, peptides as depicted in SEQ ID NOs: 1-7, 9-16, 18-38. Such diseases disorders and/or condition can involves neutrophil (polymorphonuclear leukocyte, PMN)-dependent damage or neutrophil regulation, and/ordisorders associated with TNFα-initiated cytokine activity in a subject.

Also provided by the invention is a method of treating disorders for which modulation of MrgX2 is efficacious in a subject by administering to a subject in need thereof a therapeutically effective amount of a compound falling within Formulas I, III, IV and V such as for example, peptides as depicted in SEQ ID NOs: 5, 8-13, 17-25, 28-35, 39-50.

Also provided by the invention is a method of treating disorders for which modulation of MrgX1 is efficacious in a subject by administering to a subject in need thereof a therapeutically effective amount of a compound falling within Formula III, such as for example, peptides as depicted in SEQ ID NOs: 8, 39-50.

Also provided by the invention is a method of treating treat disorders for which modulation of Mas is efficacious in a subject by administering to a subject in need thereof a therapeutically effective amount of a compound falling within Formulas I and II, such as for example, peptides as depicted in SEQ ID NOs.6-7, 9-16, 18-25, 27-31.

Also provided by the invention is a method of treating an inflammatory disorder in a subject by administering to a subject in need thereof a therapeutically effective amount of a compound falling within Formula I, II, III, IV, V and VI, such as for example, peptides as depicted in SEQ ID NOs: 1-50. The inflammatory disorder can be gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

Also provided by the invention is a method of treating fibrotic conditions involving tissue remodeling following inflammation or ischemia-reperfusion injury in a subject by administering to a subject in need thereof a therapeutically effective amount of a compound falling within Formula I, II, III, IV, V and VI, such as for example, peptides as depicted in SEQ ID NOs:1-50. These fibrotic conditions can be endomyocardial fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis); fibromatosis; granulomatous lung disease; and glomerulonephritis.

Also provided by the invention is a method of treating an autoimmune disease or disorder in a subject by administering to a subject in need thereof a therapeutically effective amount of a compound falling within Formula I, II, IV, and VI, such as for example, peptides as depicted in SEQ ID NOs: 1-7, 9-16, 18-38. The autoimmune disease can be multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Goodpasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

Also provided by the invention is a method of treating cardiovascular diseases and their complications in a subject by administering to a subject in need thereof a therapeutically effective amount of a compound falling within Formula I, II, IV, and VI, such as for example, peptides as depicted in SEQ ID NOs: 1-7, 9-16, 18-38. The cardiovascular diseases can be peripheral vascular diseases and coronary artery diseases, including but not limited to myocardial infarction; coronary heart disease; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; or platelet aggregation.

Also provided by the invention is a method of treating an ischemia-reperfusion injury in a subject by administering to a subject in need thereof a therapeutically effective amount of a compound falling within Formula I, II, IV, and VI, such as for example, peptides as depicted in SEQ ID NOs: 1-7, 9-16, 18-38. The ischemia-reperfusion injury can be associated with ischemic and post-ischemic events in organs and tissues, including but not limited to thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation. The ischemia-reperfusion injury can be alternatively following conditions including but not limited to procedures such as cardiac surgery; organ surgery; organ transplantation; angiography; cardiopulmonary and cerebral resuscitation.

Also provided by the invention is a method of treating other various disorders, diseases and/or conditions in a subject by administering to a subject in need thereof a therapeutically effective amount of a compound falling within Formula I, II, IV, and VI, such as for example, peptides as depicted in SEQ ID NOs: 1-7, 9-16, 18-38. Such disorders, diseases and/or conditions can be inhibition of alopecia, such as chemotherapy-induced alopecia; or treatment of bone disease, such as osteoporosis.

Also provided by the invention is a method of preventing and treating an hypertension and its complications in a subject by administering to a subject in need thereof a therapeutically effective amount of a compound falling within Formula I, II, III, IV, and V, such as for example, peptides as depicted in SEQ ID NOs:5-25, 27-35, 39-50. The hypertension and its complications can be hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; preeclampsia; Raynaud's phenomenon; erectile dysfunction and glaucoma. These peptides are also used as a vasodilator and in antithrombotic therapy.

Also provided by the invention is a method of treating an inflammatory disorder and/or conditions associated with an infection in a subject by administering to a subject in need thereof a therapeutically effective amount of a compound falling within Formulas I, II, IV, and VI, such as for example, peptides as depicted in SEQ ID NOs: 1-7, 9-16, 18-38. The inflammatory conditions associated with an infection, can be a bacterial infection or a viral infection, including but not limited to a viral infection caused by human immunodeficiency virus I (HIV-1) or HIV-2, acquired immune deficiency (AIDS), West Nile encephalitis virus, coronavirus, rhinovirus, influenza virus, dengue virus, hemorrhagic fever; an otological infection; severe acute respiratory syndrome (SARS), sepsis and sinusitis.

Also provided by the invention is a method of treating cancer, or inflammation associated with cancer in a subject by administering to a subject in need thereof a therapeutically effective amount of a compound falling within Formulas I, II, IV, and VI, such as for example, peptides as depicted in SEQ ID NOs: 1-7, 9-16, 18-38. The cancer, or inflammation associated with cancer can be solid cancer, including but not limited to colon cancer, lung cancer, breast cancer, prostate cancer, brain cancer, pancreatic cancer, ovarian cancer or kidney cancer. The cancer can alternatively be a melanoma, glioma, a sarcoma, a leukemia, or lymphoma. These peptides are also useful in the prevention or treatment of invasive and metastatic cancer.

Also provided by the invention is a method of treating of diseases that involve reduction of oxygen reactive species with consequent endothelial dysfunction in a subject by administering to a subject in need thereof a therapeutically effective amount of a compound falling within Formulas I and II, such as for example, peptides as depicted in SEQ ID NOs:6-7, 9-16, 18-25, 27-31. The diseases that involve reduction of oxygen reactive species with consequent endothelial dysfunction, can be cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

Also provided by the invention is a method of prevention and/or treatment of organic alterations produced by aging in a subject by administering to a subject in need thereof a therapeutically effective amount of a compound falling within Formulas I and II, such as for example, peptides as depicted in SEQ ID NOs:6-7, 9-16, 18-25, 27-31.

Also provided by the invention is a method of prevention and treatment of diseases that involve alterations in the muscular differentiation, maturation and regeneration in muscular atrophies in a subject by administering to a subject in need thereof a therapeutically effective amount of a compound falling within Formulas I and II, such as for example, peptides as depicted in SEQ ID NOs:6-7, 9-16, 18-25, 27-31. The diseases that involve alterations in the muscular differentiation, maturation and regeneration in muscular atrophies, including but not limited to as cachexia; prolonged restriction to bed due to numerous factors; chronic use of corticoids; and varied neurological syndromes, traumatisms and degenerative diseases that lead to muscular atrophy. The peptides of the invention are used for the prevention or treatment of organic alterations produced by aging and as ergogenic aids.

Also provided by the invention is a method of treating skin injury diseases, disorders and/or conditions in a subject by administering to a subject in need thereof a therapeutically effective amount of a compound falling within Formulas I, II, IV and VI, such as for example, peptides as depicted in SEQ ID NOs: 1-7, 9-16, 18-38. The skin injury diseases, disorders and/or conditions can be dermal repair, wound healing; burns, erythemas, lesions, and skin tumors.

Also provided by the invention is a method of prevention or treatment of immune related conditions in a subject by administering to a subject in need thereof a therapeutically effective amount of a compound falling within Formulas I, II, IV and VI, such as for example, peptides as depicted in SEQ ID NOs: 1-7, 9-16, 18-38. The immune related conditions including but not limited to graft versus host disease; transplant rejection, bone marrow transplantation.

Also provided by the invention is a method of mobilization, activation or inducing chemoattraction of blood cells to a site of injury in a subject by administering to a subject in need thereof a therapeutically effective amount of a compound falling within Formulas II, IV and VI, such as for example, peptides as depicted in SEQ ID NOs:1-7, 14-16, 26-27, 32-38. The blood cells can include platelets, phagocytes, monocytes, macrophages, eosinophils, neutrophils, and/or lymphocytes.

Also provided by the invention is a method of treating genetic polymorphism consequent diseases in a subject by administering to a subject in need thereof a therapeutically effective amount of a compound falling within Formulas I and II, such as for example, peptides as depicted in SEQ ID NOs:6-7, 9-16, 18-25, 27-31. The genetic polymorphism consequent diseases can be DD type of the angiotensin converting enzyme; type I and type II diabetes mellitus and complications; diabetic mellitus prophylaxis; diabetic maculopathy; and diabetic nephropathy.

Also provided by the invention is a method of prevention or treatment of a urogenital disorder or a genitor-urological disorders in a subject by administering to a subject in need thereof a therapeutically effective amount of a compound falling within Formulas I and II, such as for example, peptides as depicted in SEQ ID NOs:6-7, 9-16, 18-25, 27-31. The a urogenital disorder or a genitor-urological disorders can be renal disease; a bladder disorder; disorders of the reproductive system; gynecologic disorders; urinary tract disorder; incontinence; disorders of the male (spermatogenesis, spermatic motility), and female reproductive system; sexual dysfunction; erectile dysfunction; embryogenesis; and pregnancy related disorders. These are also used in pregnancy monitoring.

Also provided by the invention is a method of treating cytopenia in a subject by administering to a subject in need thereof a therapeutically effective amount of a compound falling within Formulas I, II, IV and VI, such as for example, peptides as depicted in SEQ ID NOs: 1-7, 9-16, 18-38. The cytopenia can be multilineage cytopenia, a thrombocytopenia, anemia, anemia due to renal failure; lymphopenia, leucopenia, neutropenia, radio/chemotherapy-related neutropenia; and platelet disorders.

Also provided by the invention is a method of prevention or treatment of respiratory diseases in a subject by administering to a subject in need thereof a therapeutically effective amount of a compound falling within Formulas I, II, IV and VI, such as for example, peptides as depicted in SEQ ID NOs: 1-7, 9-16, 18-38. The respiratory diseases can be asthma, bronchial disease, lung diseases, chronic obstructive pulmonary disease (COPD), Acute Respiratory Distress Syndrome (ARDS), severe acute respiratory syndrome (SARS).

Also provided by the invention is a method of prevention or treatment of metabolic disorders in a subject by administering to a subject in need thereof a therapeutically effective amount of a compound falling within Formulas I, II, IV, and VI, such as for example, peptides as depicted in SEQ ID NOs: 1-7, 9-16, 18-38. The metabolic disorders can be diabetes, diabetis mellitus, lipodystrophy, hyperthyroidism, glaucoma, hyperlipidaemia, non-insulin dependent diabetes, appetite control and obesity.

Also provided by the invention is a method of prevention and treatment of kidney diseases in a subject by administering to a subject in need thereof a therapeutically effective amount of a compound falling within I, II, III, IV, and V, such as for example, peptides as depicted in SEQ ID NOs:5-25, 27-35, 39-50. The kidney diseases can be diabetic nephropathy; glomerulosclerosis; nephropathies; renal impairment; scleroderma renal crisis and chronic renal failure.

Also provided by the invention is a method of prevention and treatment of blood diseases in a subject by administering to a subject in need thereof a therapeutically effective amount of a compound falling within Formula I and II, such as for example, peptides as depicted in SEQ ID NOs:6-7, 9-16, 18-25, 27-31. The blood diseases can be angioplasty (endoluminal prosthesis and post angioplasty restenosis); haematopoiesis; erythrocytosis; disorders of the blood crasis, such as post radiotherapy.

Also provided by the invention is a method of prevention and treatment of angiogenesis related conditions in a subject by administering to a subject in need thereof a therapeutically effective amount of a compound falling within Formulas I, II, IV, and VI, such as for example, peptides as depicted in SEQ ID NOs: 1-7, 9-16, 18-38. The angiogenesis related conditions including but not limited to retinal angiogenesis in a number of human ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

Also provided by the invention is a method of treating central nervous system (CNS) disorder, in a subject by administering to a subject in need thereof a therapeutically effective amount of a compound falling within Formulas I, II, III, IV, and V, such as for example, peptides as depicted in SEQ ID NOs:5-25, 27-35, 39-50. The central nervous system (CNS) disorder, including but not limited to central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, locomotor activity and a peripheral nervous system disorder.

Also provided by the invention is a method of treating and controlling pain in a subject by administering to a subject in need thereof a therapeutically effective amount of a compound falling within Formulas I, III, IV, and V, such as for example, peptides as depicted in SEQ ID NOs:5, 8-13, 17-25, 28-35, 39-50. The pain includes but not limited to complex regional pain, muscoskeletal pain, neuropathic pain, post-herpetic pain, pain associated with cancer, or post-operative pain.

Optionally, the cDNA that encodes the peptide sequences of the invention are used in gene therapy to treat the respective diseases, disorders and/or conditions, as detailed hereinabove.

The invention will be further illustrated in the following examples.

Method for analysis of peptides' ability to influence Calcium Flux (Revelant to Examples 1-4, below)

The assay was carried out in CHO cells were transiently transfected with the GPCR of choice, by utilizing the promiscuous Gα16 to divert signaling to the Gq pathway, thus enabling readout of GPCR activation by testing for Calcium flux as described by Liu et al 2003 (Biomol Screen 8, 39-49).

Peptides (listed in FIG. 1) were synthesized by the solid phase peptide synthesis (SPPS) method, cleaved from the resin, and purified by RP-HPLC unless stated otherwise. The peptide's identity was verified by mass spectrometry. Final purity of peptide was >90% as measured by RP-HPLC. Peptides were diluted in PBS containing 0.1% BSA. All plates were stored at −80 C until use.

All the peptides thus obtained were tested for their ability to change calcium flux in CHO—K1 cells (ATCC-CCL-61) transiently co-transfected with an expression vector containing the GPCR of choice and expression vector containing the Gα16 encoding cDNA. Expression constructs containing cDNA clones for MrgX1, MrgX2, Mas or FPRL1 were commercially obtained in one of the following expression vectors: pcDNA3.1, pCMV6, or MO2.

Transient transfections were performed using CHO—K1 cells as host cells. Cells (12 million) were plated into T75 flasks on the day preceding transfection. Cells were transfected with the appropriate GPCR expression vector and with a vector expressing $G_{\alpha 16}$ using a lipid-based reagent, MTI, according to the manufacturer's recommendation. Cells were transfected for 5 hours, then re-plated into 96-well dishes (60,000 cells per well) and grown overnight.

On the day of the experiment, cells were loaded with Fluo4-NW (Invitrogen) according to the manufacturer's recommendation. Plates were loaded into a FlexStation™ (Molecular Devices) plate reader and fluorescence was monitored. Seventeen seconds following initiation of reading, cells were stimulated with the indicated agonist/compound at final concentration of 1 μM. Each 96 well plate contained cells transfected with one GPCR expression vector and each of the examined peptides was tested in triplicate.

We defined a hit as a peptide which elicited a clear and distinct increase in intracellular calcium that is clearly visible and statistically significant upon examination of the calcium trace for at least two repeats. The criterion for statistical significance was a p-value lower than 0.001 in a t-test comparing the levels of calcium before and after peptide addition.

Based on dose response experiments, EC50 best fit values were calculated by non-linear regression of sigmoidal dose-response curves, using Prism version 4 (GraphPad Software Inc., San Diego, Calif.). The formulae for the sigmoidal dose-response curves was defined as Y=Bottom+(Top−Bottom)/(1+10^(LogEC50−X)*HillSlope))

EXAMPLE 1

Induction of Calcium Flux in MrgX1-Transfected CHO Cells

The ability of Peptides to change calcium flux was examined as described above in CHO—K1 cells co-transfected with MrgX1 and Gα16. The following results were obtained:
Peptide 60_S (SEQ ID NO:8)

Figure 3:
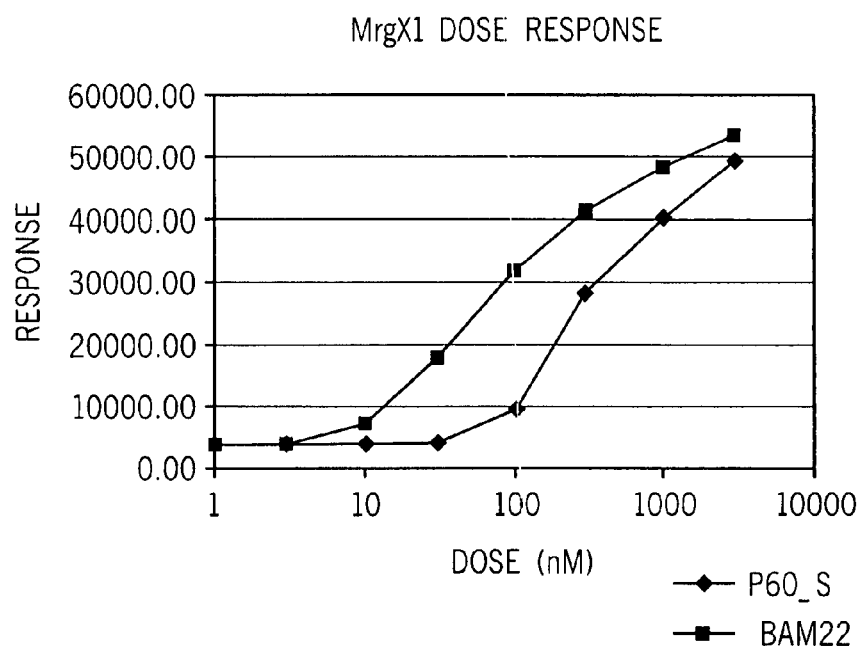
FIG. 3 is a line graph demonstrating the dose response of CHO—K1 cells transfected with MrgX1 to Peptide 60_S.

As shown in FIG. 2, P60_S (SEQ ID NO:8) present in all three wells increased calcium flux of MrgX1-transfected CHO cells during the time period between 20 seconds and 90 seconds relative to the negative control. In addition, P60_S induced a dose dependent activation of MrgX1 (FIG. 3) when examined at 1, 3, 10, 30, 100, 300, 1000, and 3000 nM. The response to P60_S at the highest concentration was similar to that of the positive control, BAM22 (FIG. 3). From these results, the EC50 was calculated to be at least 300 nM for Peptide 60_S (SEQ ID NO:8), while the EC50 for BAM22 is at least 50 nM.

EXAMPLE 2

Induction of Calcium Flux in MrgX2-Transfected CHO Cells

The ability of Peptides to change calcium flux was examined in CHO—K1 cells co-transfected with MrgX2 and Gal 6. Several peptides were found to induce calcium flux in this experimental system as follows:
Peptide 60_S (SEQ ID NO:8)

Figure 4:
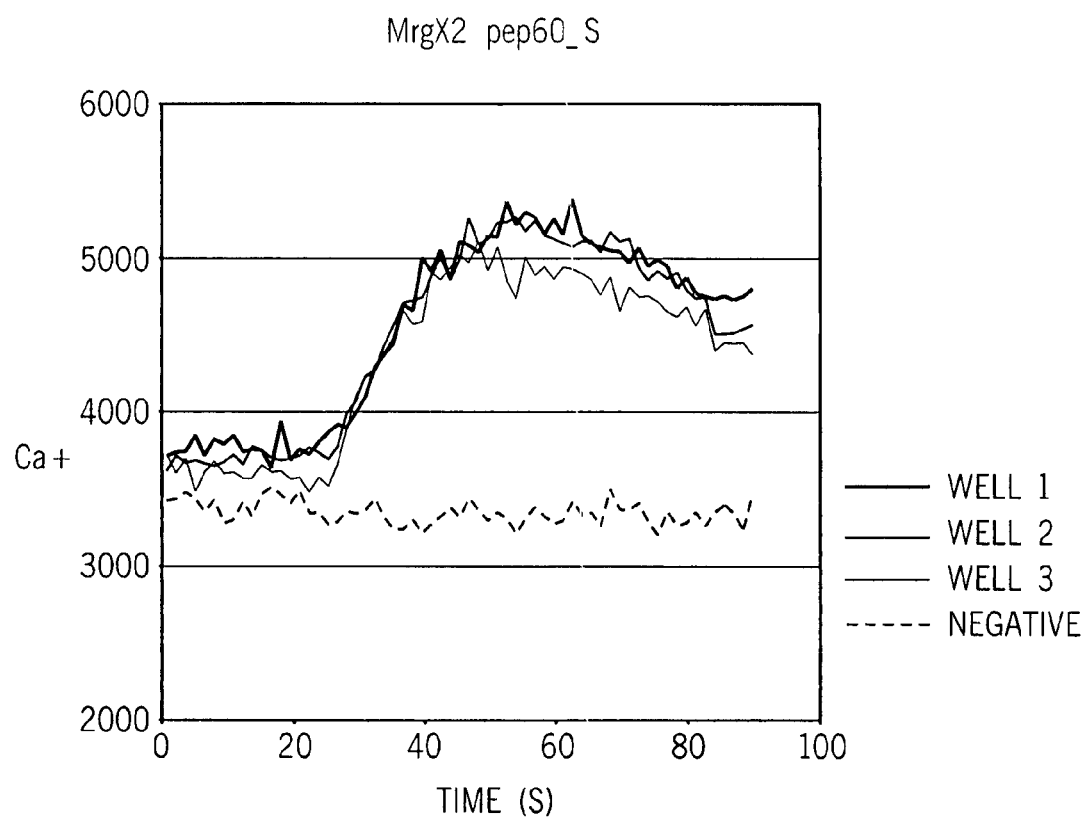
FIG. 4 is a line graph demonstrating the effect of Peptide 60_S on calcium flux in CHO—K1 cells transfected with MrgX2.

As shown in FIG. 4, the sample of P60_S (SEQ ID NO:8) present in all three wells increased calcium flux during the time period between about 20 seconds and 90 seconds relative to the negative control.

Peptide 94 (SEQ ID NO:5)

Figure 5:
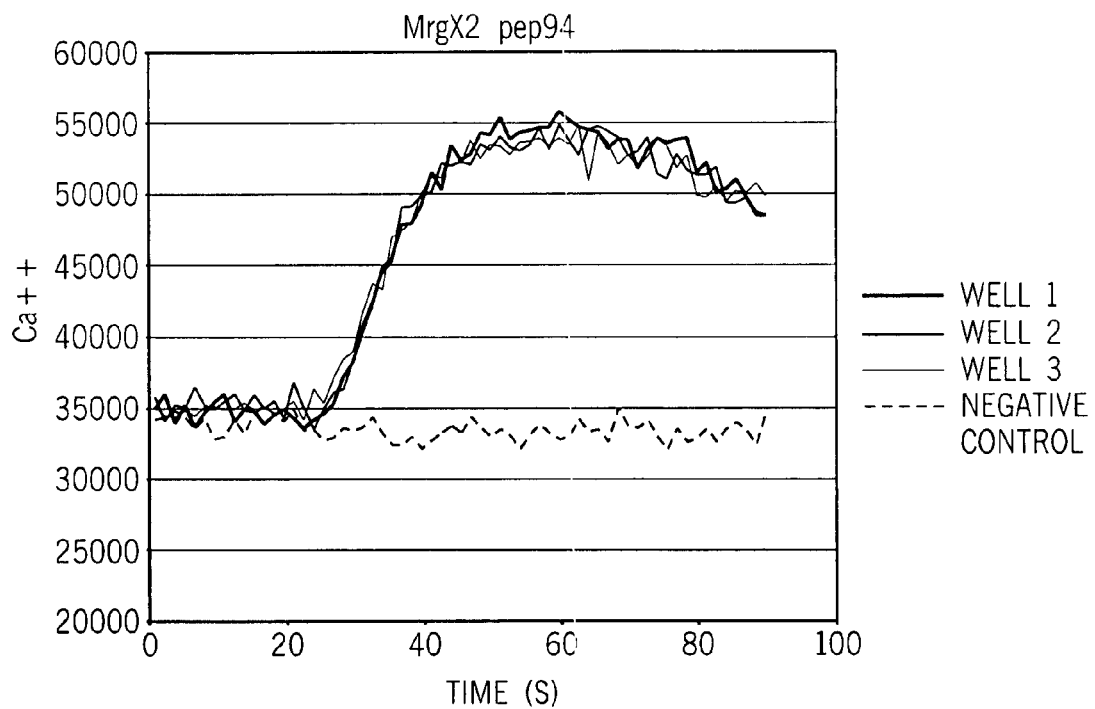
FIG. 5 is a line graph demonstrating the effect of Peptide 94 on calcium flux in CHO—K1 cells transfected with MrgX2.

As shown in FIG. 5 the sample of P94 (SEQ ID NO:5) present in all three wells increased calcium flux during the time period between about 20 seconds and 90 seconds relative to the negative control.

Peptide 61_S (SEQ ID NO:10)

Figure 6:
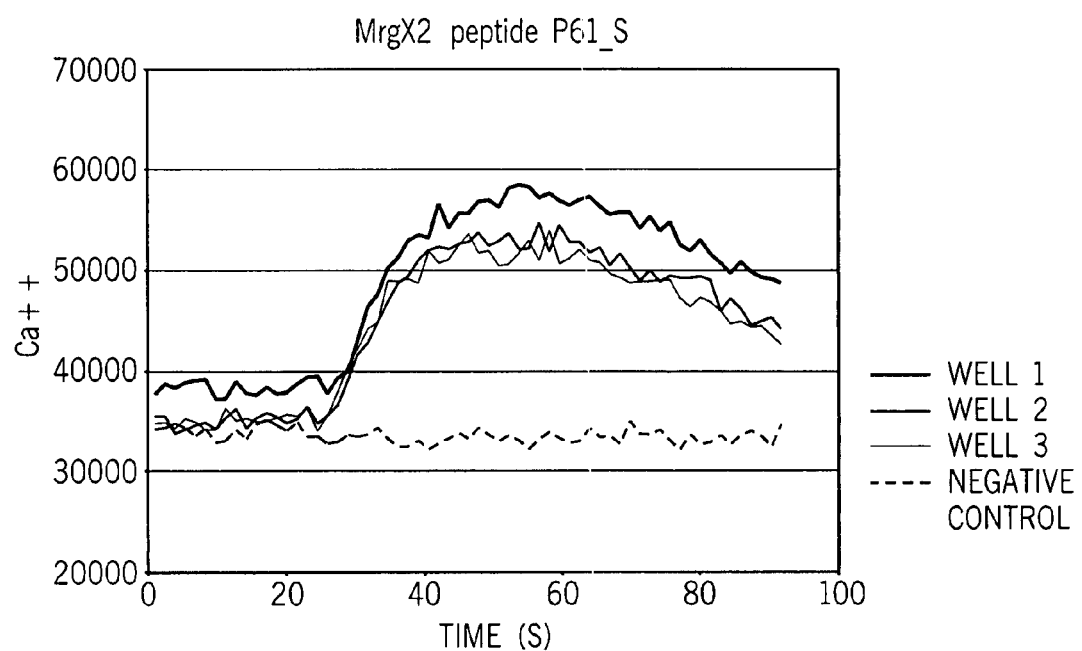
FIG. 6 is a line graph demonstrating the effect of Peptide 61_S on calcium flux in CHO—K1 cells transfected with MrgX2.

As shown in FIG. 6, the samples of Peptide 61_S (SEQ ID NO:10) present in all three wells increased calcium flux during the time period between about 20 seconds and 90 seconds relative to the negative control.

Peptide 63 (SEQ ID NO:17)

Figure 7:
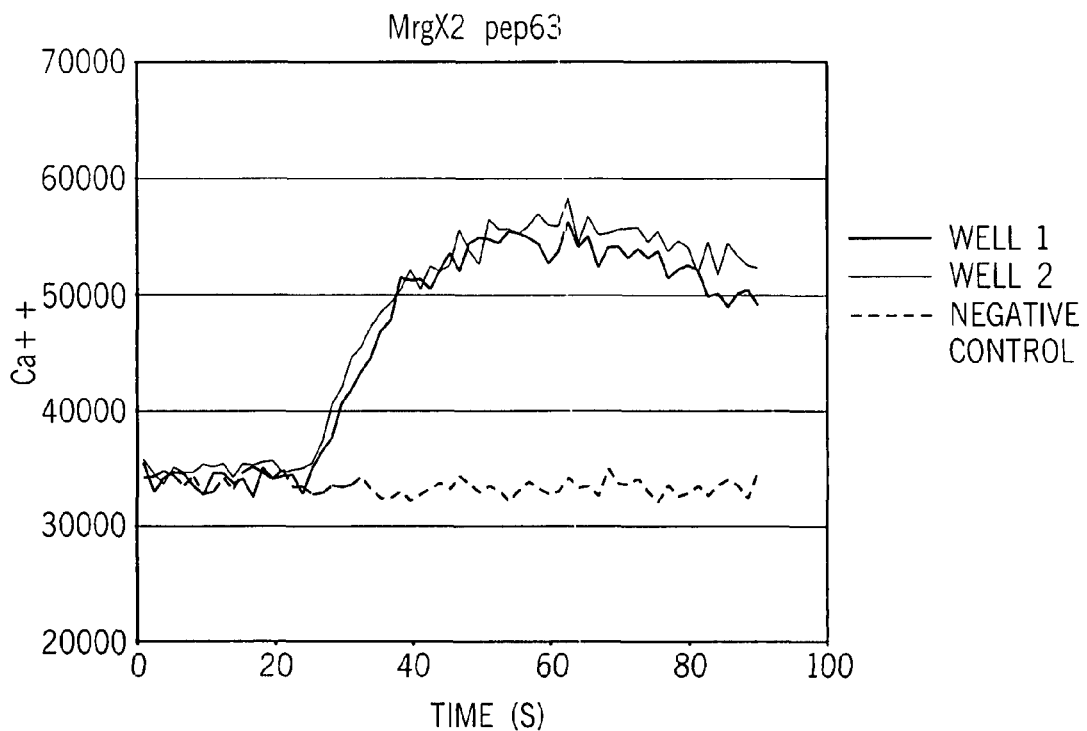
FIG. 7 is a line graph demonstrating the effect of Peptide 63 on calcium flux in CHO—K1 cells transfected with MrgX2.

As shown in FIG. 7, the sample of Peptide 63 (SEQ ID NO:17) present in both wells increased calcium flux during the time period between about 20 seconds and 90 seconds relative to the negative control.

EXAMPLE 3

Induction of Calcium Flux in Mas-Transfected CHO Cells

The ability of Peptides to change calcium flux was examined in CHO—K1 cells co-transfected with Mas receptor and Gα16. The following peptides were found to induce calcium flux in this experimental system:

A. Activation of Mas by P33 Family a. P33

Figure 8:
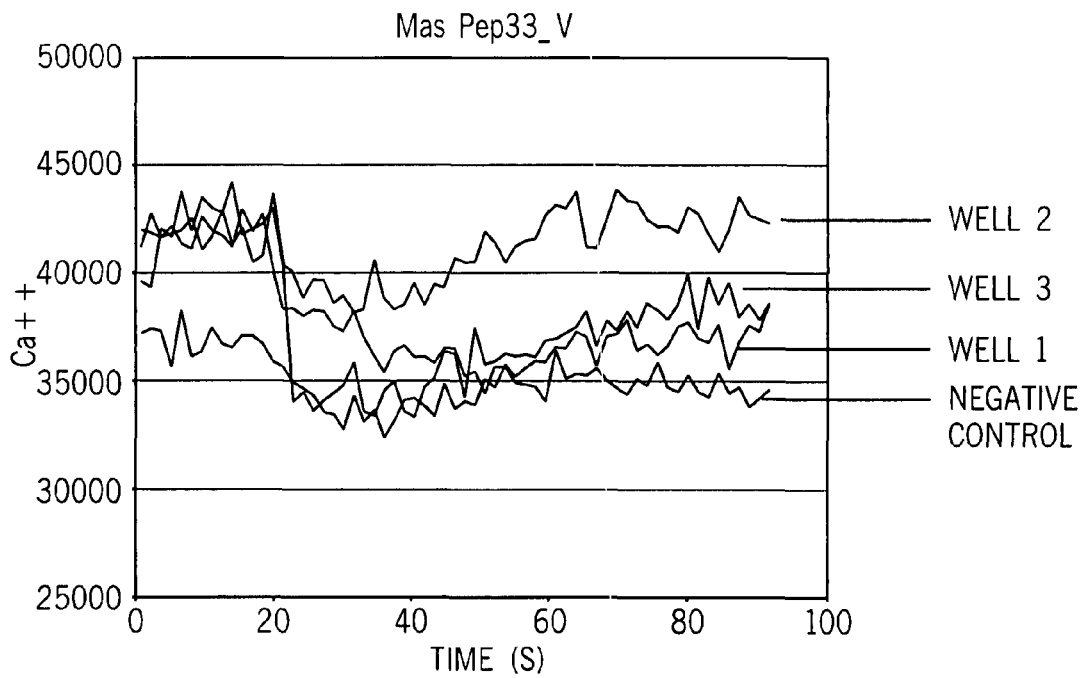
FIG. 8 is a line graph showing the effect of Peptide 33_V on calcium flux in CHO—K1 cells transfected with Mas.

As detailed in FIG. 1, Peptide 33 (SEQ ID NO:6) contains a Cysteine in position 3. In order to avoid dimerization or other interaction of the peptide via the Cysteine, this amino acid was substituted for Val to create P33_V (SEQ ID NO:7) which allowed the synthesis of a homogenously monomeric peptide. As shown in FIG. 8, the sample of P33_V (SEQ ID NO:7) present in well 2 increased calcium flux in the transfected cells during the time period between 20 seconds and 90 seconds relative to the negative control. The samples of P33_V (SEQ ID NO:7) present in wells 1 and 3 increased calcium flux during the time period between 60 seconds and 90 seconds relative to the negative control.

Figure 39:
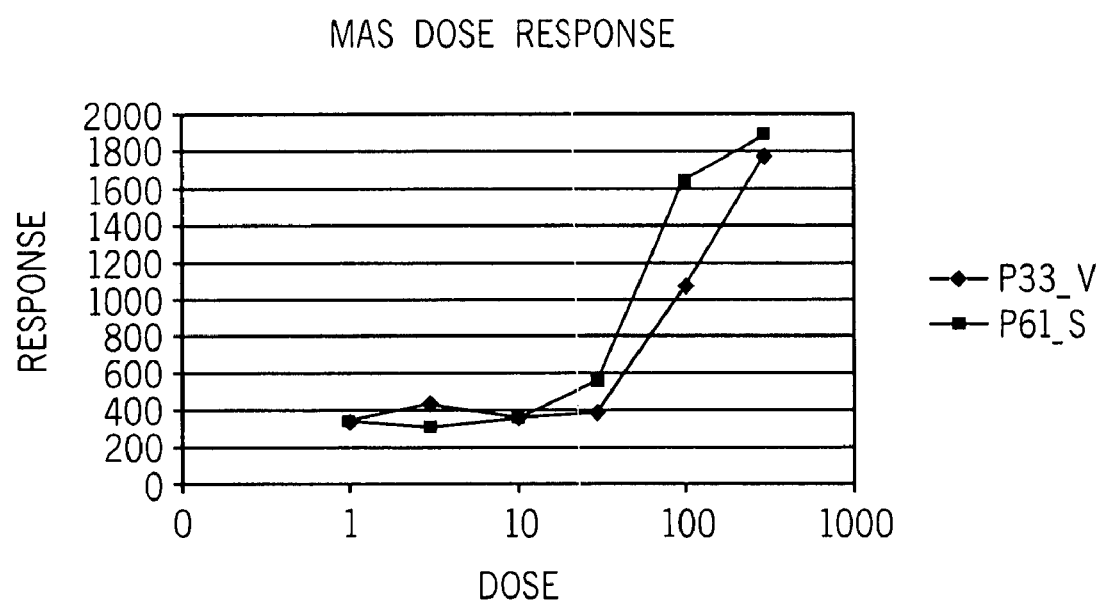
FIG. 39 is a line graph demonstrating the dose response of CHO—K1 cells transfected with Mas to P33_V and P61_S.
Figure 40:
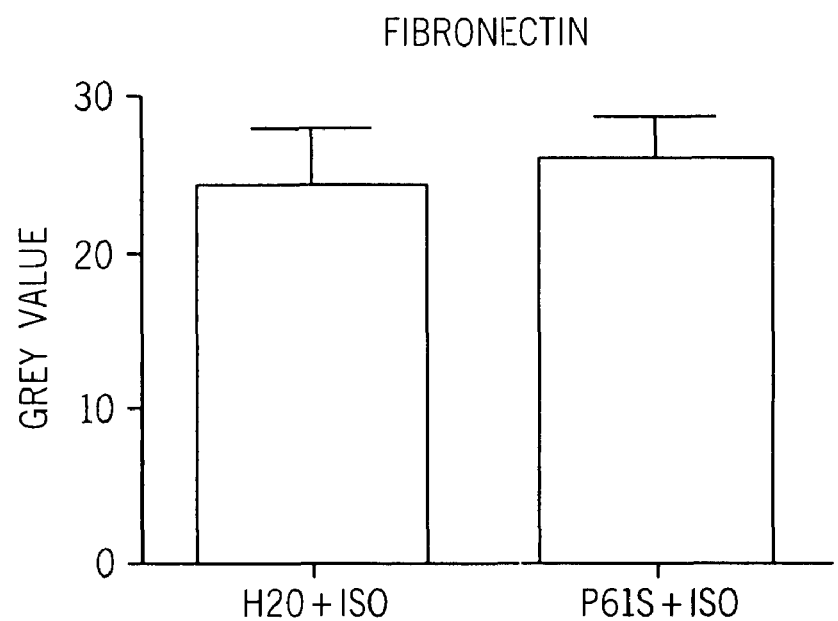
FIG. 40 is a histogram depicting Fibronectin deposition in Isoproterenol induced rats in control animals and in the presence of P61_D.
Figure 41:
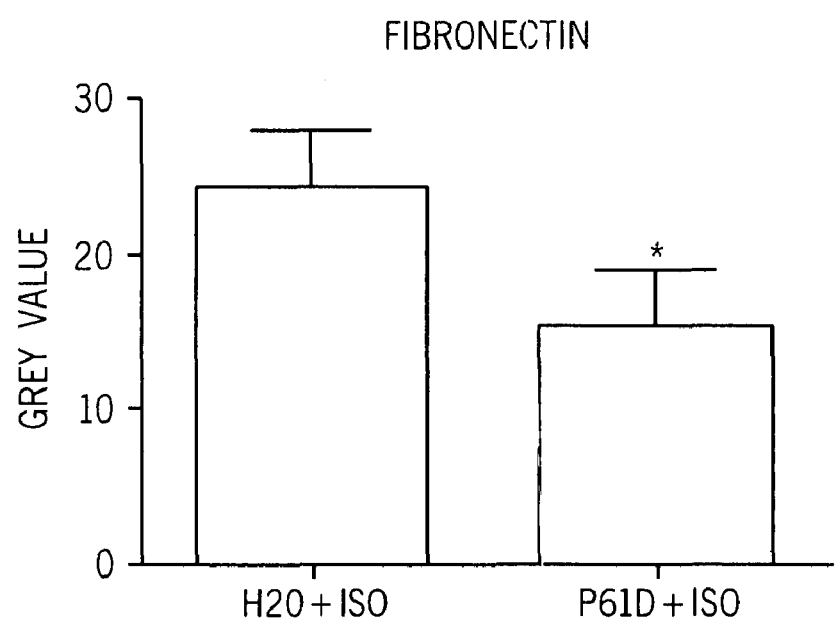
FIG. 41 demonstrates Fibronectin deposition in Isoproterenol induced rats in the presence or absence of P61_S.
Figure 42:
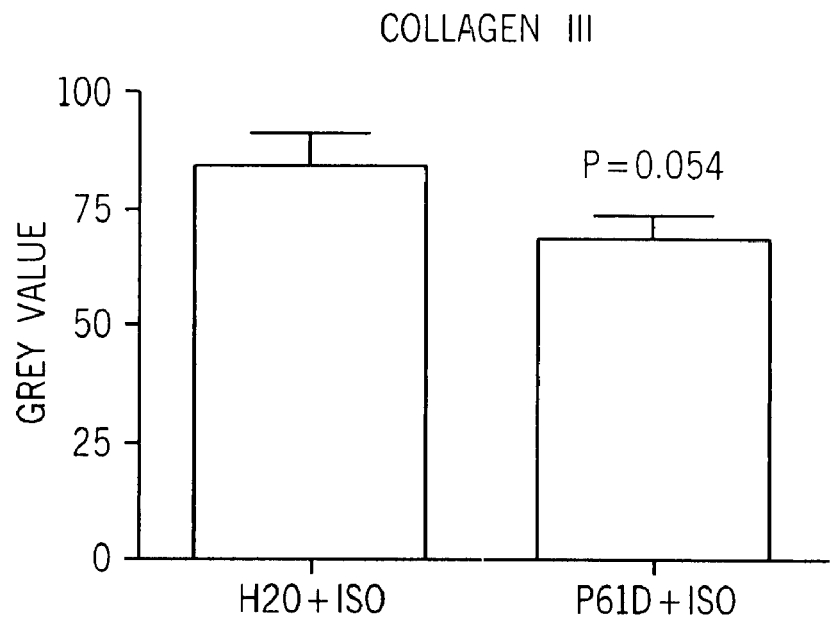
FIG. 42 demonstrates Collagen III deposition in Isoproterenol induced rats in the presence or absence of P61_D.
Figure 43:
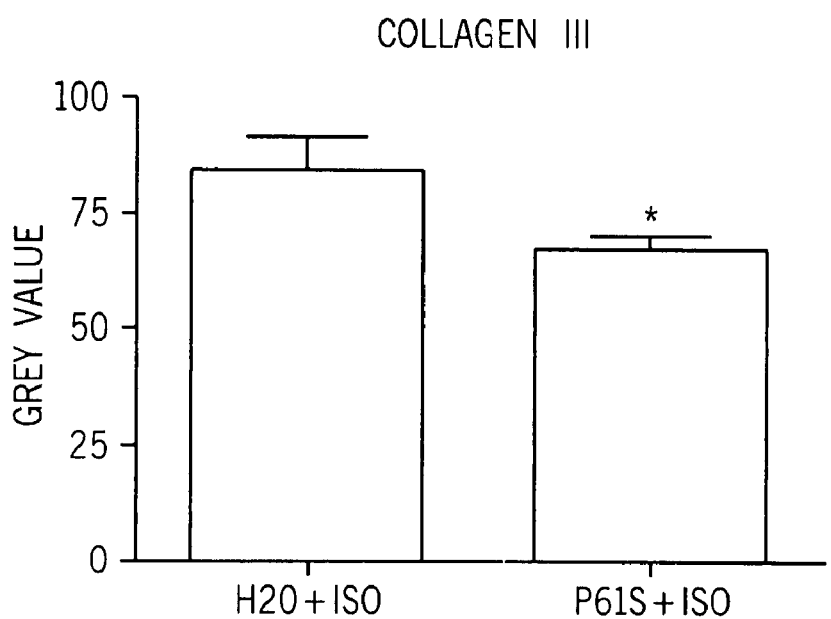
FIG. 43 demonstrates Collagen III deposition in Isoproterenol induced rats in the presence or absence of P61_S.
Figure 44:
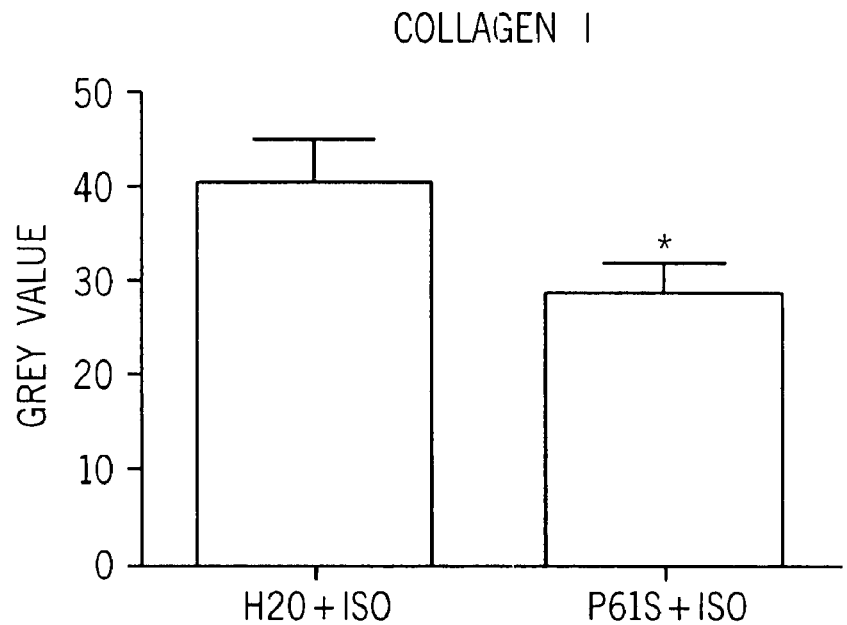
FIG. 44 demonstrates Collagen I deposition in Isoproterenol induced rats in the presence or absence of P61_S.
Figure 45:
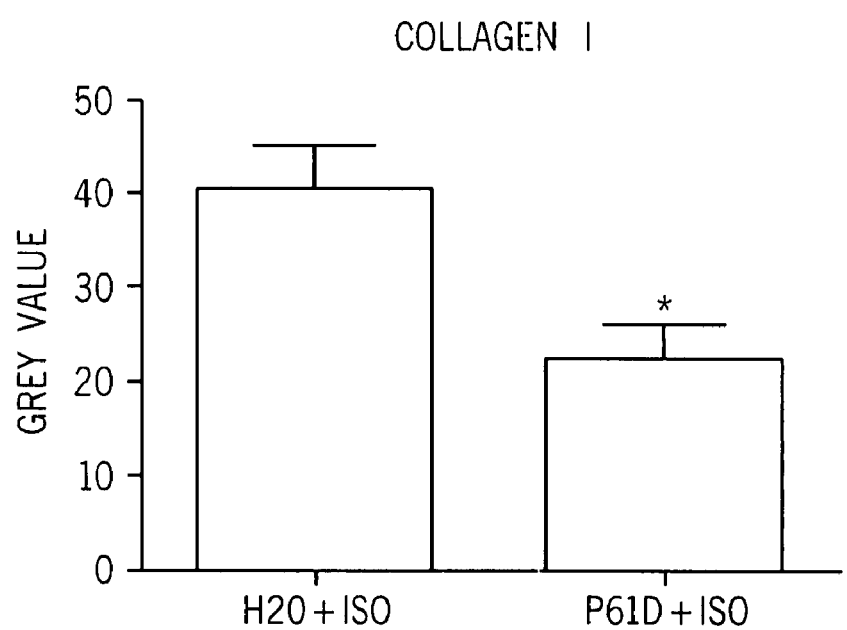
FIG. 45 demonstrates Collagen I deposition in Isoproterenol induced rats in the presence or absence of P61_D.
Figure 46:
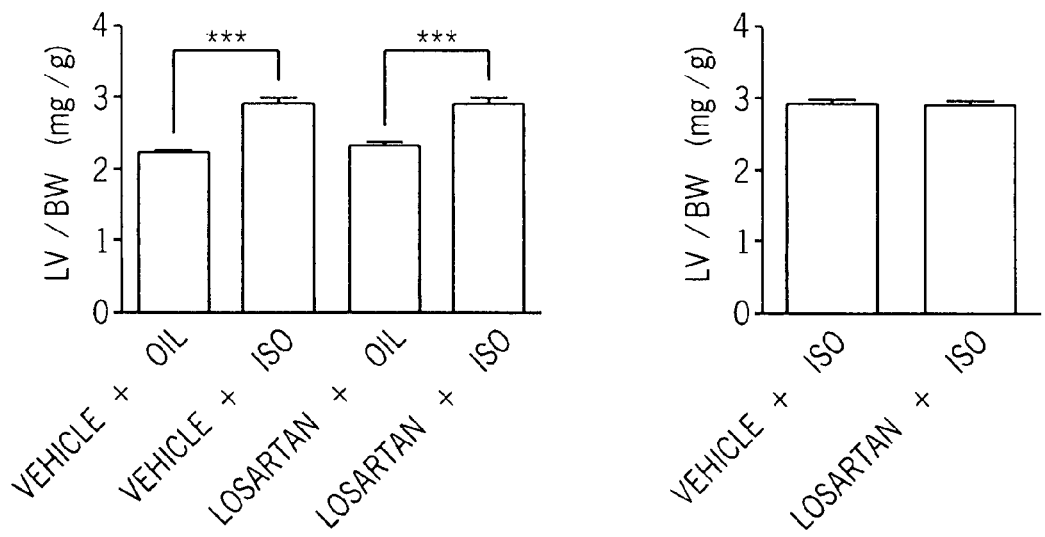
FIG. 46 demonstrates a ratio of left ventricular mass to body weight in control and Isoproterenol treated rats in the presence or absence of Losartan.
Figure 47:
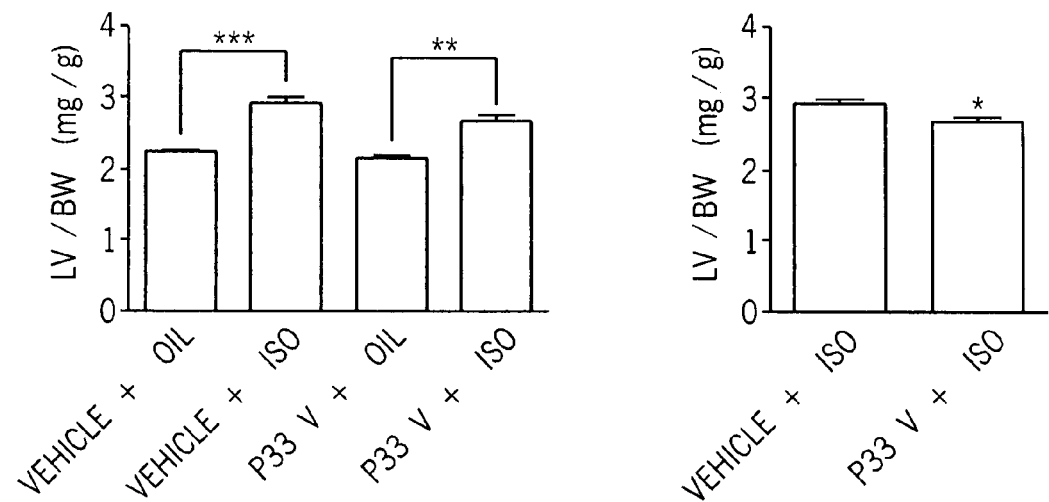
FIG. 47 demonstrates a ratio of left ventricular mass to body weight in control and Isoproterenol treated rats in the presence or absence of P33_V.
Figure 48:
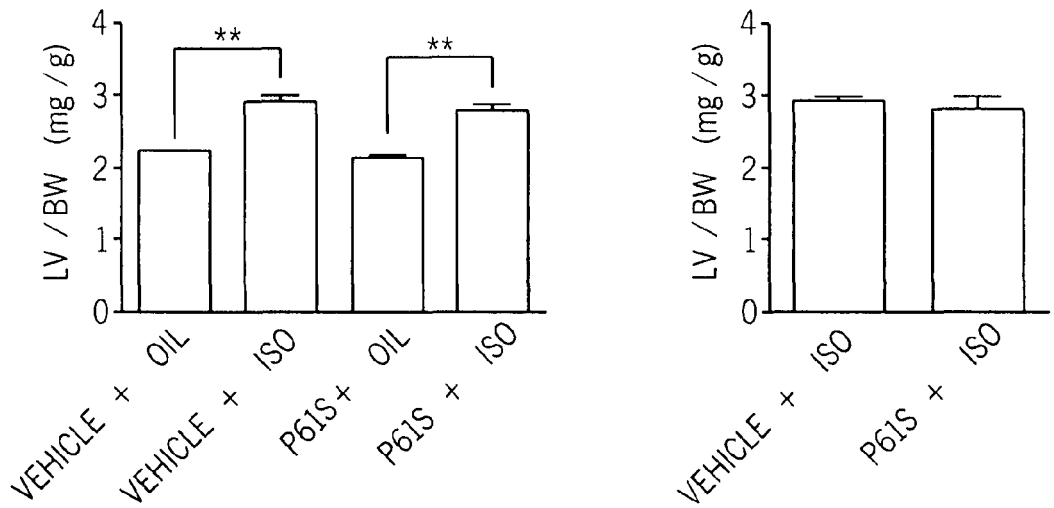
FIG. 48 ratio of left ventricular mass to body weight in control and Isoproterenol treated rats in the presence or absence of P61_S.
Figure 49:
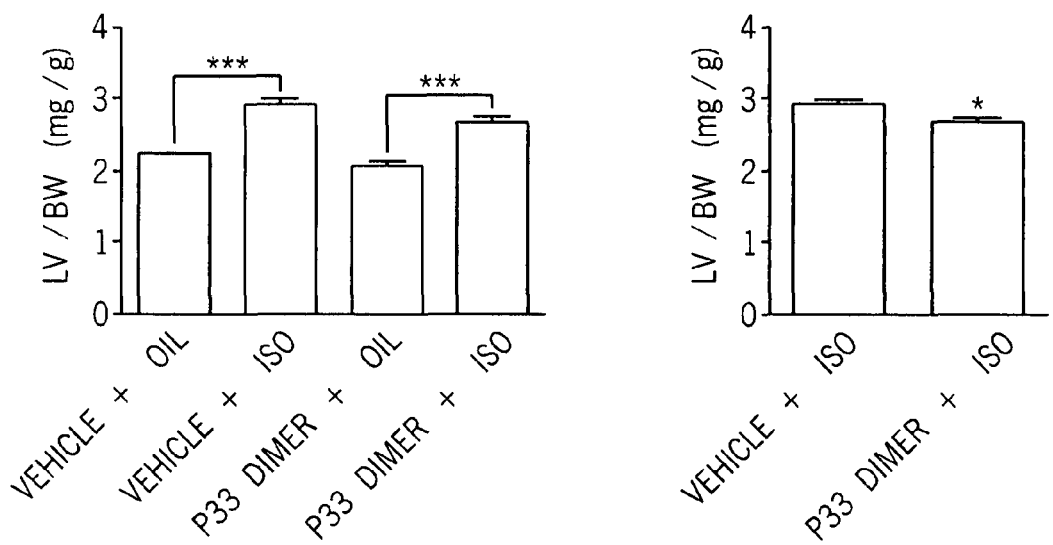
FIG. 49 demonstrates a ratio of left ventricular mass to body weight in control and Isoproterenol treated rats in the presence or absence of P33_D.
Figure 50:
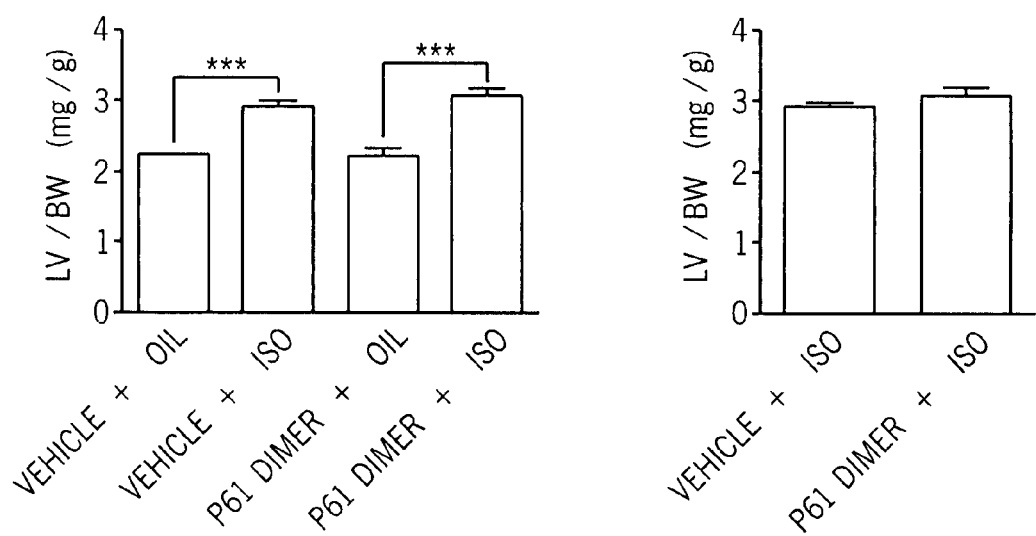
FIG. 50 demonstrates a ratio of left ventricular mass to body weight in control and Isoproterenol treated rats in the presence or absence of P61_D.

FIG. 39 shows the dose response of Mas to Peptide 33_V (SEQ ID NO. 7). The doses examined in this experiment were 10, 30, 100, 300, 1000 and 3000 nM. The known endogenous Mas ligand, Ang (1-7) (data not-shown), did not induce Ca response in this assay, as reported in the literature (Santos et al., (2003), PNAS: 100, 8258-8263). The highest response to Peptide 33_V was not reached. The results indicate that the EC50 for Peptide 33_V is at least 1000 nM.

b. P33 Peptide Derivatives

In order to further characterize the activity of P33, the original, Cys bearing P33, was synthesized both as a monomer and a dimer (P33_mono and P33_dimer also named P33_D, respectively; (SEQ ID NO. 6)). The monomeric and dimeric forms of P33 were synthesized by the solid phase peptide synthesis (SPPS) with the "FMOC" strategy. The crude peptides were then obtained by cleavage form the resin by TFA solution. Purification of the crude peptides was done on HPLC to the degree of 95%. Dimerization of the Cysteine was performed by air oxidation and the dimer was again purified to 95%. To avoid dimerization or other interaction of a peptide that contains Cysteine (P33_mono), the sulfhydryl moiety of the Cysteine was protected with Acm group which remains stable under the acidic cleavage of the peptide from resin. For P33_V, the TFA salt was further replaced to acetate salt with the aid of ammonium acetate and acetic acid followed by HPLC purification. The identity of the peptides was determined by Mass Spectroscopy.

In addition, shorter derivates of P33 (P33_5, P33_8, P33_9, P33_10; SEQ ID NOs:27, 14, 15, 16, respectively, FIG. 1) were synthesized and studied for their ability to induce calcium flux in the Mas-transfected CHO—K1 cells. The shorter derivates of Peptide 33 were synthesized by the solid phase peptide synthesis (SPPS) with the "FMOC" strategy, followed by cleavage form the resin by TFA solution and purification using HPLC to the degree of 95% as described above.

Figure 9:
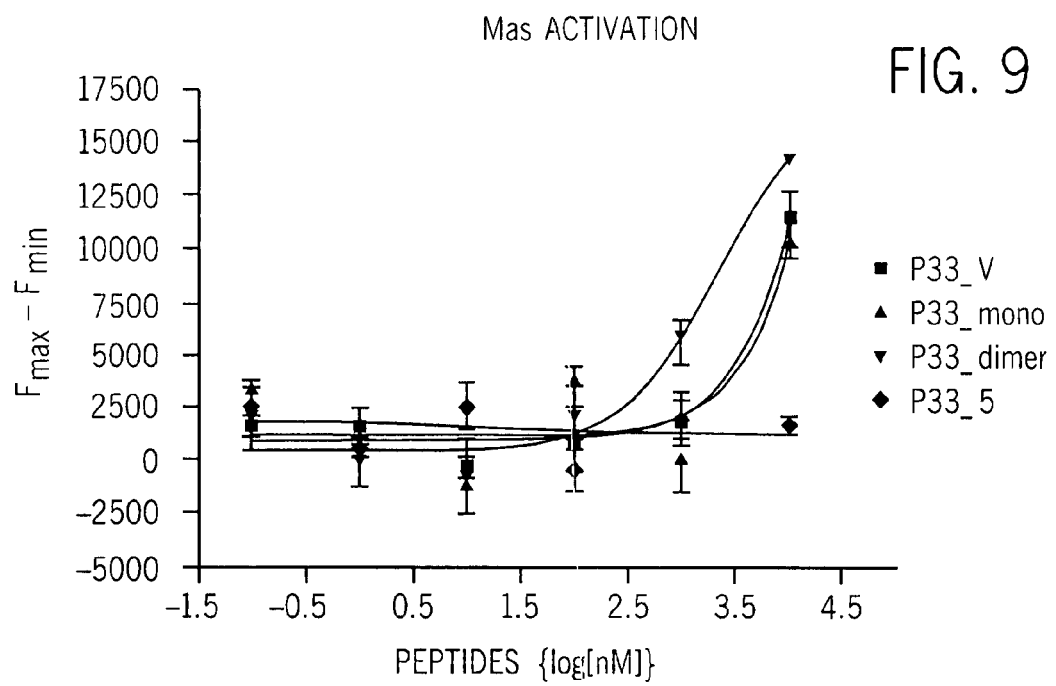
FIG. 9 is a line graph demonstrating the dose response of CHO—K1 cells transfected with Mas to Peptides P33_V, P33_mono, P33_dimer, and P33__5.
Figure 10:
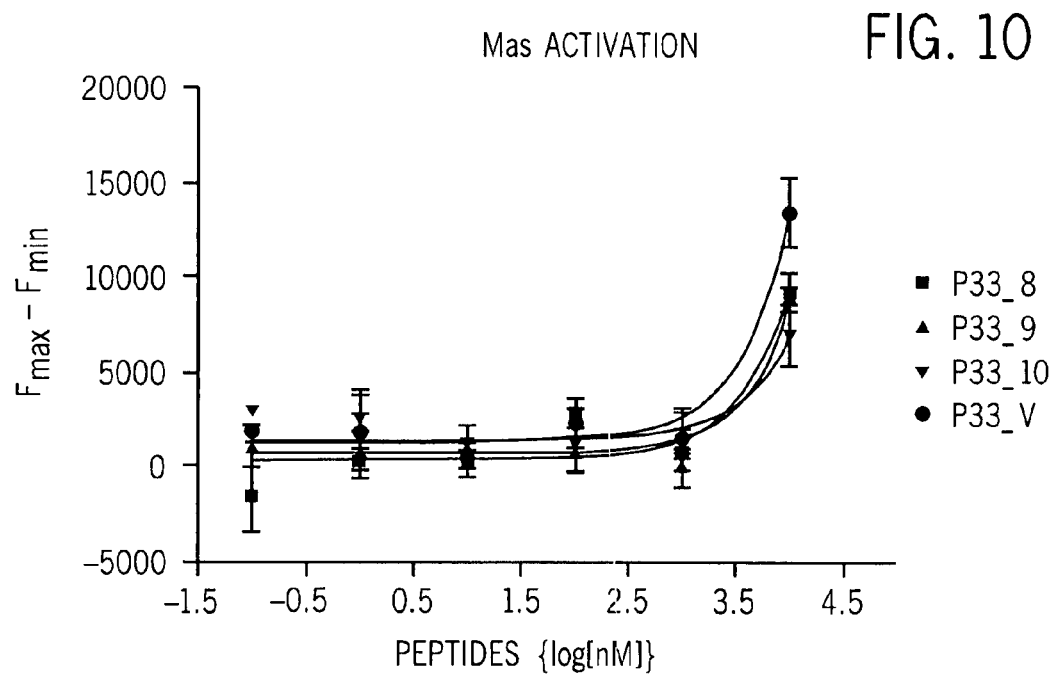
FIG. 10 is a line graph demonstrating the dose response of CHO—K1 cells transfected with Mas to Peptides P33__8, P33__9, P33__10, and P33_V.

The P33 monomer and dimer, as well as other P33 derivative peptides were compared for their ability to induce calcium flux in the Mas-transfected cells at 0.1, 1, 10, 100, 1000 and 10000 nM. As shown in FIG. 9, the monomeric forms of P33 (P33_mono and P33_V) are equally potent while the P33_dimer is superior to the monomeric peptides. P33_5 showed no activity in this assay (FIG. 9), while the other P33 derivatives (P33_8, P33_9 and P33_10) induced calcium flux, albeit at a somewhat lower degree compared to P33_V (FIG. 10).

B. Activation of Mas by P61 Family a. Peptide 61

Figure 11:
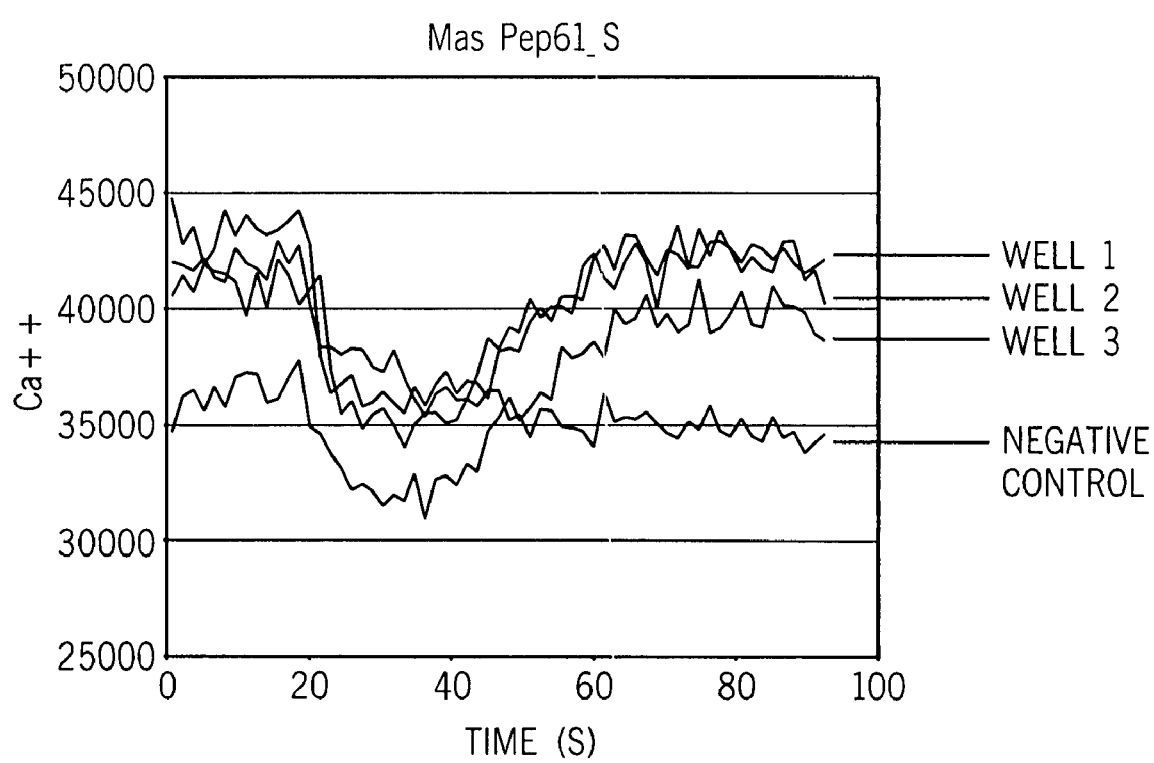
FIG. 11 is a line graph illustrating the effect of Peptide 61_S on calcium flux in CHO—K1 cells transfected with Mas).

Peptide 61 (SEQ ID NO:9) has a Cysteine in position 5 which was substituted for Serine in order to avoid dimerization or other interactions of the peptide. The peptide thus obtained was named P61_S (SEQ ID NO:10) (FIG. 1). As shown in FIG. 11, P61_S induced calcium flux in the Mas-transfected cells: samples of Peptide 61_S present in wells 1 and 2 increased calcium flux during the time period between 45 seconds and 90 seconds relative to the negative control whereas the sample of Peptide 61_S present in well 3 increased calcium flux during the time period between 50 seconds and 90 seconds relative to the negative control.

FIG. 39 shows the dose response of Peptide 61_S. The doses examined in this experiment were 10, 30, 100, 300, 1000 and 3000 nM. The highest response to Peptide 61_S was not reached. The results indicate that the EC50 for Peptide 61_S is at least 500 nM. As explained above, the known endogenous Mas ligand, Ang (1-7), did not induce a Ca response.

b. P61 Peptide Derivatives

Figure 12:
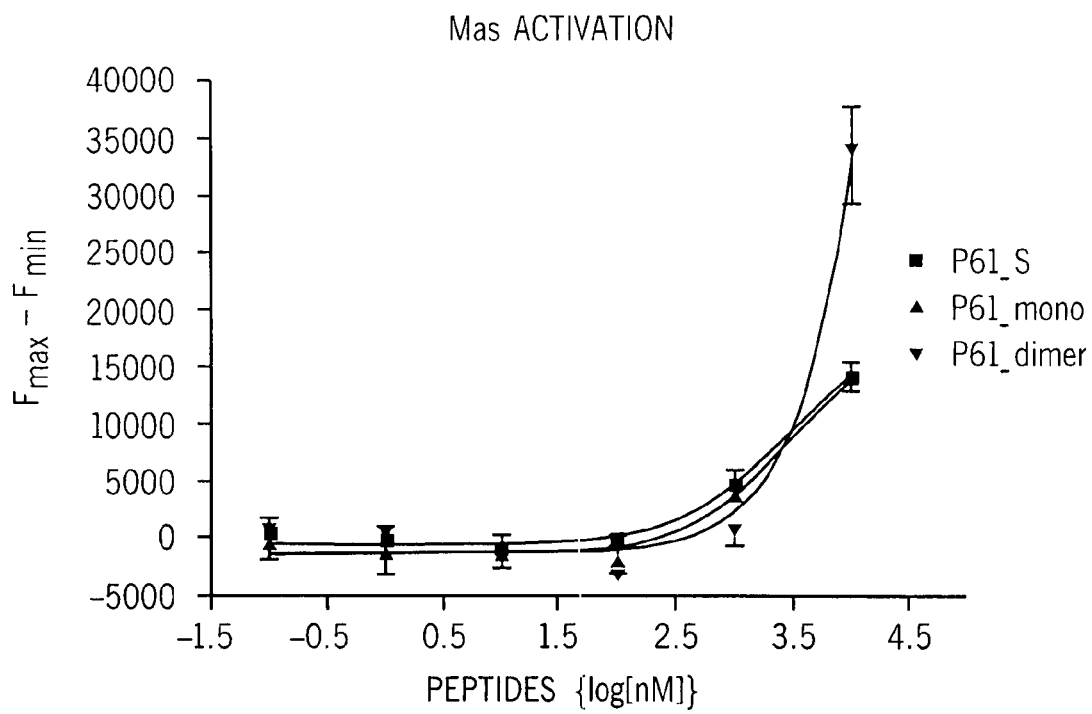
FIG. 12 is a line graph demonstrating the dose response of CHO—K1 cells transfected with Mas to P61_S, P61_mono, and P61_dimer.
Figure 13:
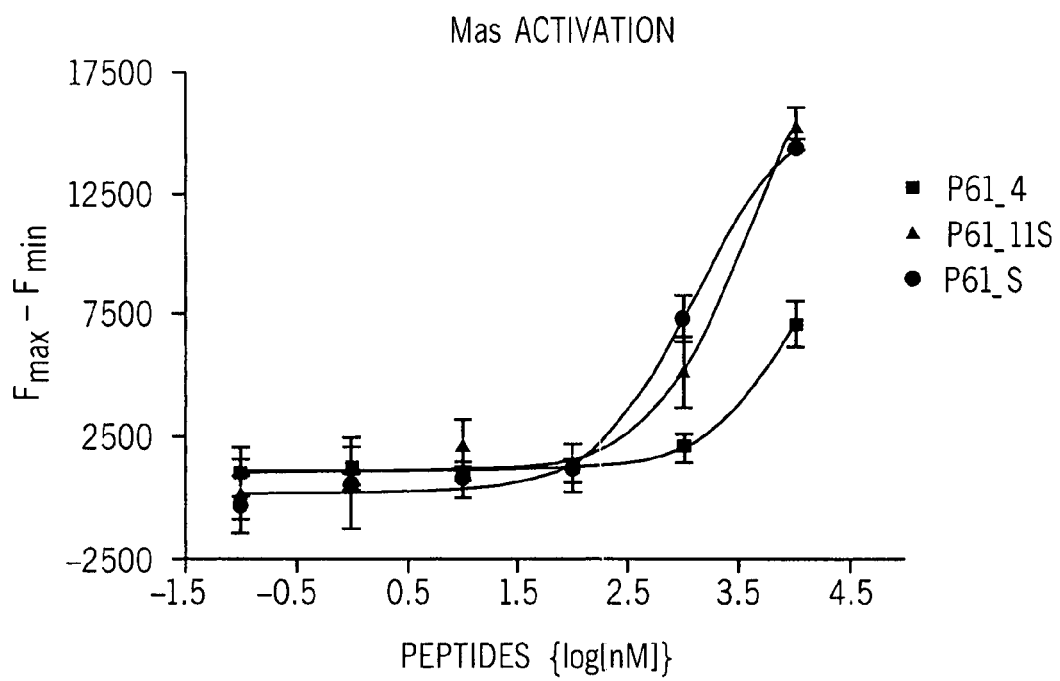
FIG. 13 is a line graph demonstrating the dose response of CHO—K1 cells transfected with Mas to P61__4, P61__11S, and P61_S.

Similarly to P33 (see above), the original cysteine-bearing P61 was synthesized both as a monomer (P61_mono) and as a dimer (P61_dimer) (SEQ ID NO. 9). Shorter derivates of P61 were also synthesized (FIG. 1). These P61-related peptides were studied for their ability to induce calcium flux in the Mas-transfected cells. As shown in FIG. 12, the P61_dimer (SEQ ID NO:9) was more potent than the monomeric P61 peptides: P61_S (SEQ ID NO:10) and P61_mono (SEQ ID NO:9). FIG. 13 indicates that P61_11S (SEQ ID NO:12) was as potent as P61_S, while P61_4 (SEQ ID NO:11) was somewhat weaker.

Mas activation is not always linked to calcium flux, for example, Mas endogenous ligand, Ang 1-7 does not elicit calcium flux. Thus, it is still possible that the peptides which did not induce calcium flux in the Mas-transfected cells would activate Mas via other pathways. In addition, it is possible that the experimental system is not sufficiently sensitive or that these peptides interact with the receptor in a different manner, or via different binding site than the "active" peptides. Thus, this interaction should be further characterized.

Out of the 16 peptides (of families P33 and P61) that were screened by the calcium flux assay (P61_5S was not tested in this assay due to its low solubility in water), four peptides were chosen to be further examined by ex vivo and in vivo assays (P61_S (SEQ ID NO:10); P61-dimer (SEQ ID NO:9);

P33_V (SEQ ID NO:7) and P33-dimer (SEQ ID NO:6)), as described below in Examples 9-12.

EXAMPLE 4

Induction of Calcium Flux in FPRL1-Transfected CHO Cells

Figure 14:
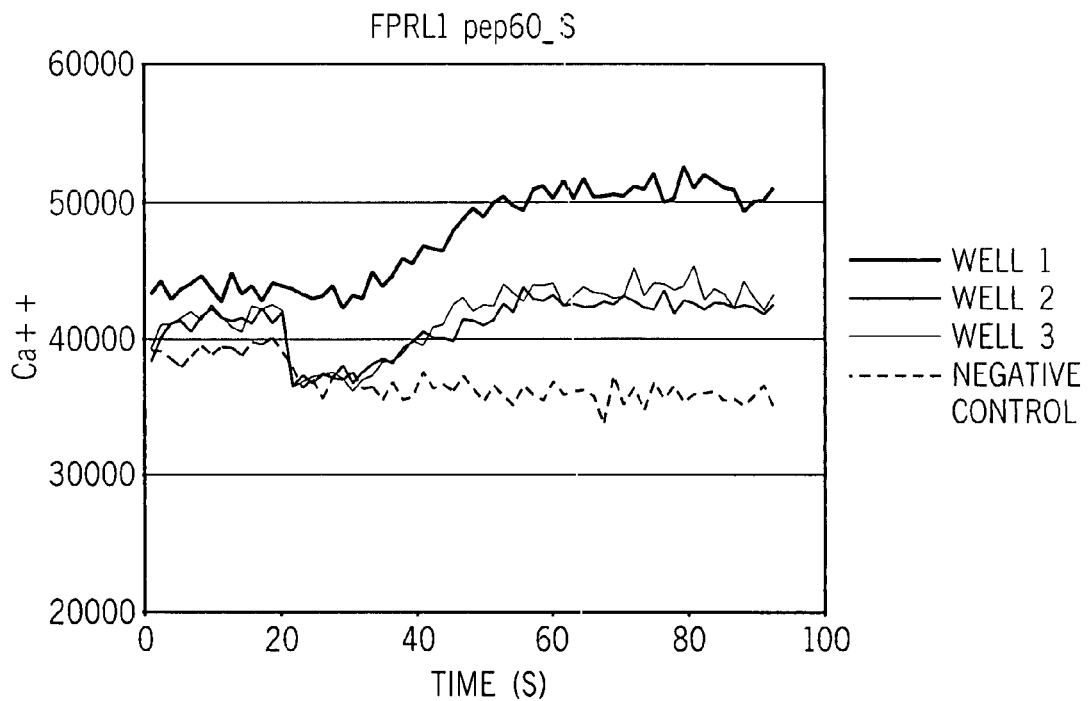
FIG. 14 is a line graph demonstrating the effect of Peptide 60_S on calcium flux in CHO—K1 cells transfected with FPRL1.
Figure 15:
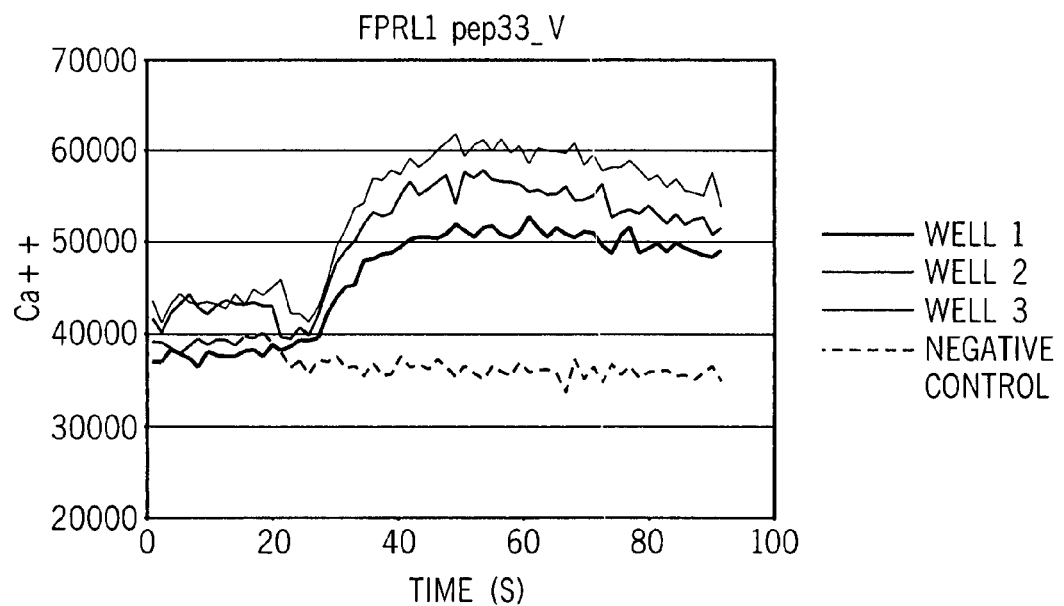
FIG. 15 is a line graph demonstrating the effect of Peptide 33_V on calcium flux in CHO—K1 cells transfected with FPRL1.

The ability of Peptides to change calcium flux was examined in CHO—K1 cells co-transfected with FPRL1 and Gal 6. Several peptides were found to induce calcium flux in this experimental system as follows:
Peptide P60_S (SEQ ID NO:8):
As shown in FIG. 14 the sample of P60_S present in all three wells increased calcium flux during the time period between about 20 seconds and 90 seconds relative to the negative control.
Peptide P33_V (SEQ ID NO:7):
As shown in FIG. 15, the sample of Peptide 33_V present in all three wells increased calcium flux during the time period between about 20 seconds and 90 seconds relative to the negative control.

Figure 16:
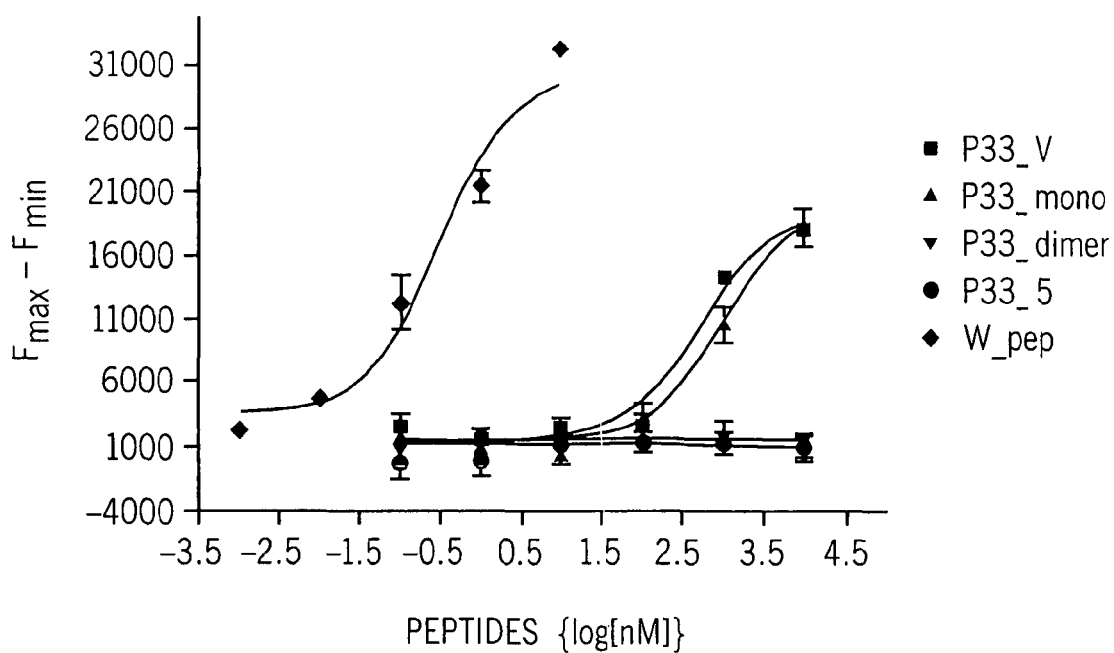
FIG. 16 is a line graph showing the effect of Peptide 33 and its derivatives on calcium flux in CHO—K1 cells transfected with FPRL1, as compared to W peptide.
Figure 17:
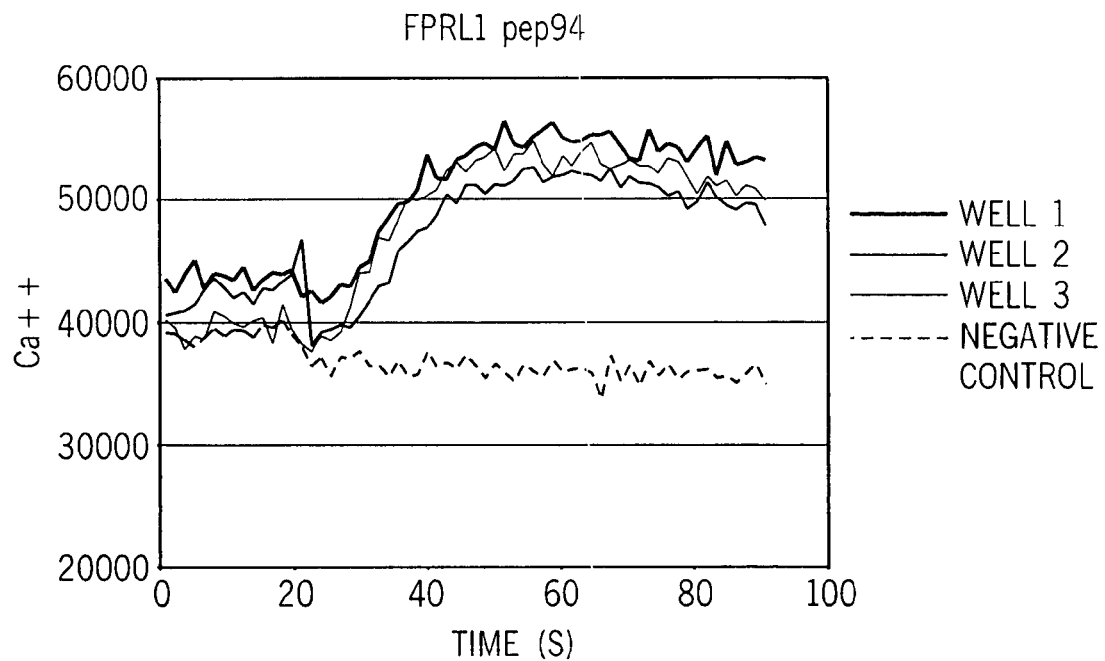
FIG. 17 is a line graph demonstrating the effect of Peptide 94 on calcium flux in CHO—K1 cells transfected with FPRL1.

The P33-derived peptides (see FIG. 1): P33_V (SEQ ID NO:7), P33 (SEQ ID NO:6)-mono, P33 (SEQ ID NO:6)-dimer, P33_5 (SEQ ID NO:27), P33_8 (SEQ ID NO:14), P33_9 (SEQ ID NO:15) and P33_10 (SEQ ID NO:16) were tested for their ability to activate FPRL1 using the calcium flux assay in FPRL1-transfected CHO cells. As shown in FIG. 16, the monomeric forms of Peptide 33, P33_V and P33_mono, were similarly potent in their ability to induce calcium flux in the concentrations tested (0.1, 1, 10, 100, 1000, 10000 nM) while P33_dimer was inactive. The shorter derivates of P33 (P33_5, P33_8, P33_9 and P33_10) also failed to induce calcium flux in the tested concentrations (FIG. 16, and data not shown). The lack of activity of these peptides might be due to reduced potency; insufficient sensitivity of the experimental system, alternative interaction of the receptor, or activation of other pathways, which are not related to calcium flux. Thus, this interaction should be further characterized.
Peptide 94 (SEQ ID NO:5)
As shown in FIG. 17, the sample of P94 (SEQ ID NO:5) present in all three wells increased calcium flux during the time period between about 20 seconds and 90 seconds relative to the negative control.

Figure 18:
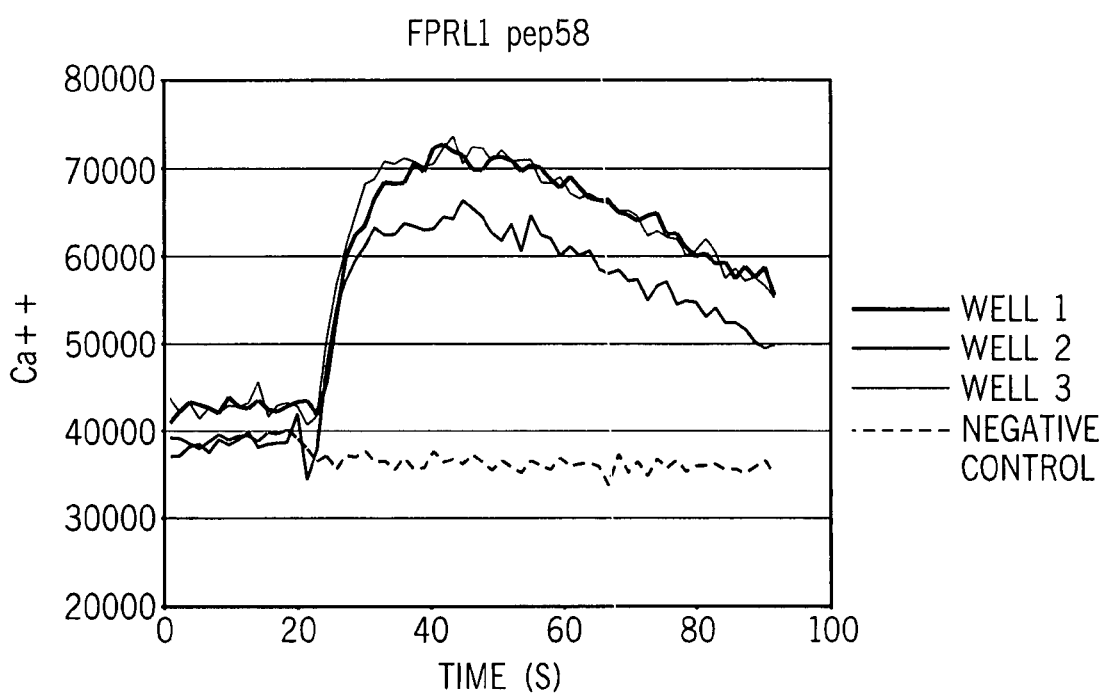
FIG. 18 is a line graph demonstrating the effect of Peptide 58 on calcium flux in CHO—K1 cells transfected with FPRL1.

Shorter peptides derived from Peptide 94 (listed in FIG. 1) were synthesized and purified as previously described. These peptides failed to induce calcium flux (data not shown). This could result from insufficient sensitivity of the experimental system, alternative interaction of the receptor, or activation of other pathways, which are not related to calcium flux. Thus, this interaction should be further characterized.
Peptide 58 (SEQ ID NO:1)
As shown in FIG. 18, the samples of P58 (SEQ ID NO:1) present in all three wells increased calcium flux during the time period between about 20 seconds and 90 seconds relative to the negative control.

Figure 19:
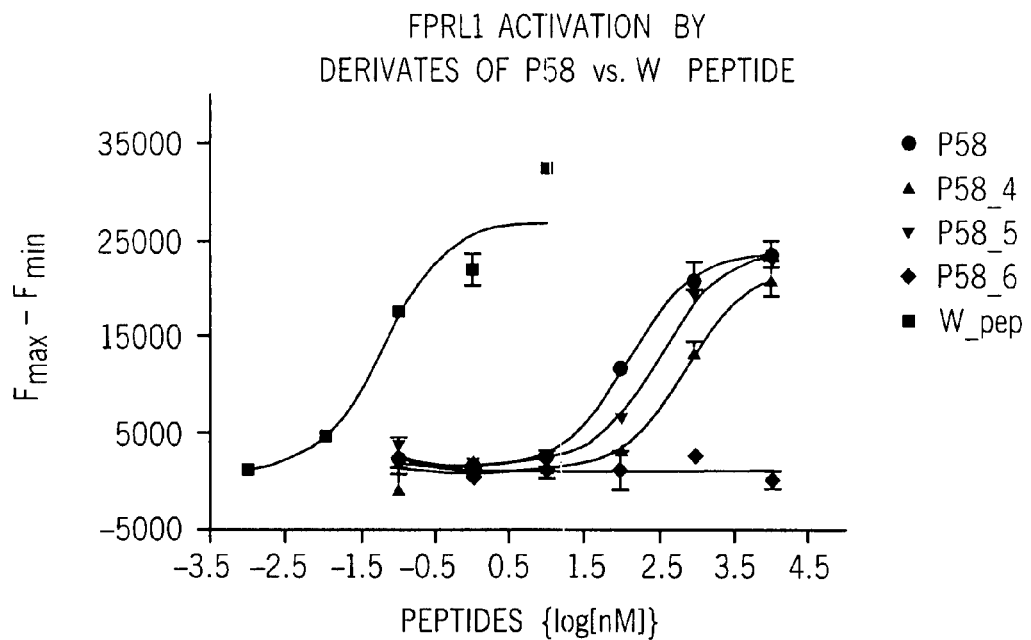
FIG. 19 is a line graph demonstrating the effect of Peptide P58 and some of its derivatives on calcium flux in CHO—K1 cells transfected with FPRL1, as compared to W peptide.
Figure 20:
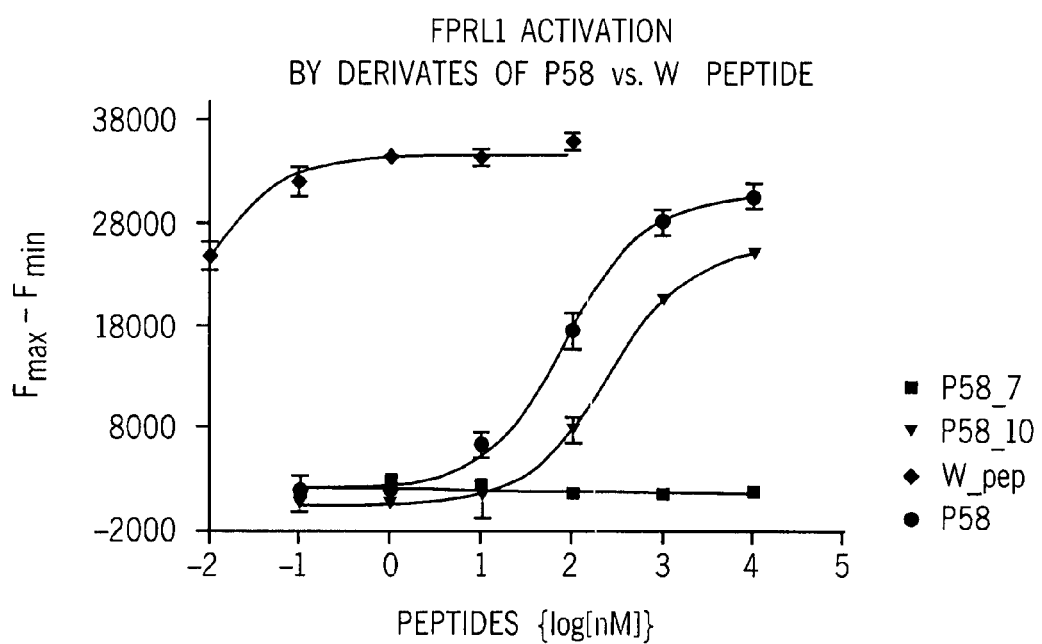
FIG. 20 is a line graph demonstrating the effect of Peptide P58 and some of its derivatives on calcium flux in CHO—K1 cells transfected with FPRL1, as compared to W peptide.
Figure 21:
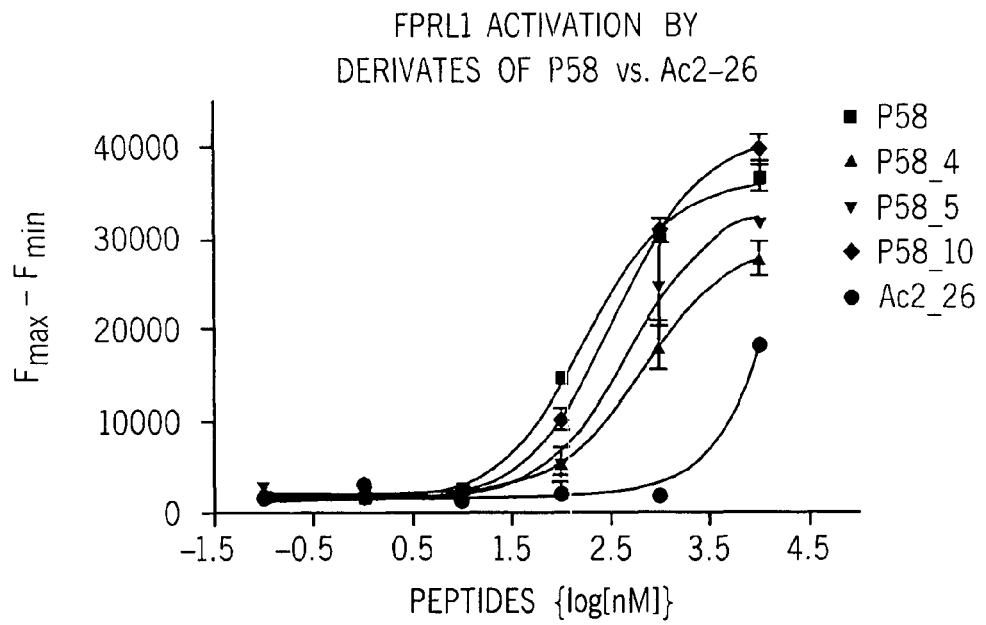
FIG. 21 is a line graph demonstrating the effect of Peptide 58 and its derivatives on calcium flux in CHO—K1 cells transfected with FPRL1, as compared to Ac2-26.

In order to further characterize P58, shorter peptides derived from its sequence were synthesized and studied in the calcium flux assay. As shown in FIGS. 19-21, P58 and its derivates P58_4 (SEQ ID NO:2), P58_5 (SEQ ID NO:3) and P58_10 (SEQ ID NO:4), elicited calcium flux in the FPRL1 transfected CHO cells in a dose dependent manner. All peptides induced calcium flux via FPRL1, but were less potent than W peptide that served as a positive control (FIGS. 19-20). W peptide is known for its very high affinity to FPRL1 (ref?). However, W peptide is an artificial peptide with no beneficial therapeutic activity. The P58 peptides were also compared to Ac2-26, a known FPRL1 agonist possessing anti-inflammatory activity, and were found to be more potent in eliciting calcium flux (FIG. 21).

The following P58 derivative peptides did not induce calcium flux in the FPRL1-transfected cells: P58_6 (SEQ ID NO:38), P58_7 (SEQ ID NO:36), P58_12 (SEQ ID NO:37) (FIGS. 19-20 and data not shown). However, FPRL1 activation is not always linked to calcium flux; for example, lipoxin A4 and its analogs evoke anti-inflammatory activity via FPRL1, but do not eliciting calcium flux. Thus, it is still possible that these peptides would activate FPRL1 via other pathways. In addition, it is possible that the experimental system is not sufficiently sensitive or that these peptides interact with the receptor in a different manner, or via different binding site than the calcium-inducing peptides.

Out of the 20 peptides screened by the calcium flux assay for FPRL1 activation, three peptides were chosen to be further examined in in vivo assays: P58 (SEQ ID NO:1), P58_4 (SEQ ID NO:2) and P58_5 (SEQ ID NO:3).

EXAMPLE 5

Competitive Radioligand Binding Assay of Peptide 58 to FPRL1

Figure 22:
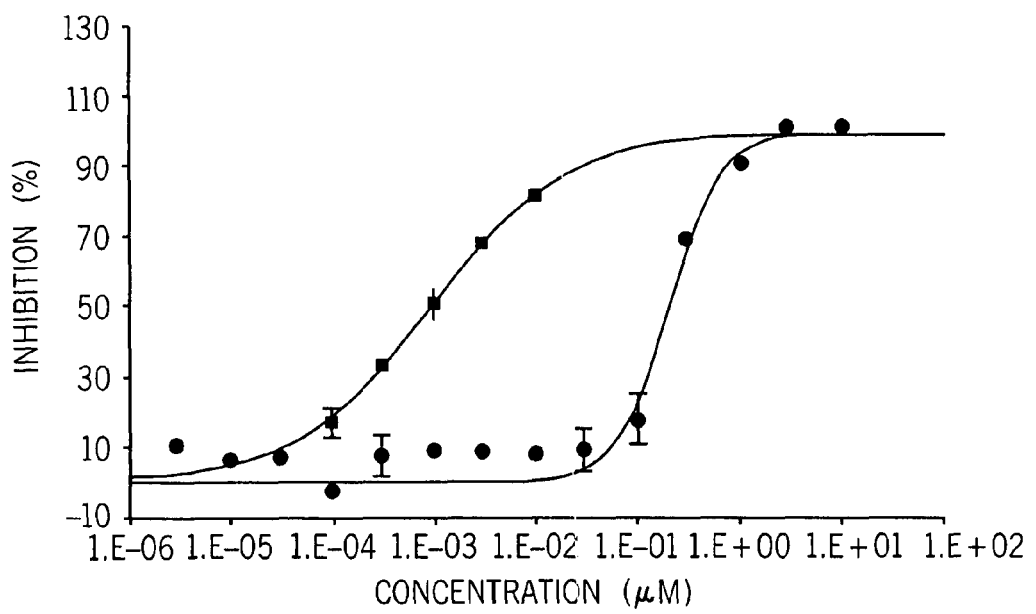
FIG. 22 is a response curve depicting the results of a competitive radioligand binding assay for Peptide 58 to FPRL-1.

The specific binding of Peptide 58 (SEQ ID NO:1) to FPRL1 was analyzed by testing its ability to compete with 0.025 nM [$^{125}$I] WKYMVm (W peptide), a known agonist of FPRL1, for binding to FPRL1 in CHO transfected cells. CKβ8-1 (aa 46-137), another known ligand of FPRL1 was used as a positive control in this assay (Chiang et al 2006, Pharmacological Reviews 58, 463-487). Peptides were incubated with cells for 90 minutes at 25° C., in the presence of Incubation Buffer (50 mM HEPES, pH 7.4, 100 mM NaCl, 5 mM KCl, 5 mM MgCl2, 2 mM Ca Cl2, 0.5% BSA) and the amount of radioactive W peptide was measured. The results in FIG. 22 show inhibition of W peptide binding, and indicate that P58 inhibited W peptide binding to FPRL1 in a dose dependent manner, with an IC50 0.189 μM and a Ki 0.0541 μM.

EXAMPLE 6

The In Vivo Effect of Peptide 58 on Zymosan-Induced Polymorphonuclear Leukocyte Influx into Air Pouches In order to analyze the ability of P58 to exert in vivo effects via the FPRL1 receptor, an acute experimental model of inflammation, the Zymosan-induced murine dorsal air pouch model, was used. The Zymosan-induced infiltration of PMNs in this model has previously been shown to be inhibited by agonists of the FPRL1 receptor, such as lipoxins and Annexin 1-derived peptides (Perretti et al 2002, Nature Medicine 8, 1296-1302).
Animals:
Male out-bred Swiss albino mice were purchased from Harlan, UK (T.O. strain) and maintained on a standard chow pellet diet with tap water ad libitum and a 12:00 h light/dark cycle. All animals were housed for 7 days prior to experimentation to allow body weight to reach ~30 g on the day of the experiment.
Drug Treatment and Experimental Design:
Drugs were stored at −20° C. and defrosted on the day of the experiment. Peptide P58 was provided lyophilized; it was taken back to room temperature and dissolved with sterile PBS before use to make an initial 1 mg/ml solution. Peptide Ac2-26 (positive control) was also dissolved with sterile PBS before use to make an initial 1 mg/ml solution. Vehicle consisted of sterile pyrogen free PBS (Gibco, cat no. 14190-094). Once dissolved, P58 (SEQ ID NO:1) and Ac2-26 gave a clear solution. Drugs or vehicle were administered i.v. at a final volume of 200-μl, this volume containing the doses described below.

Experimental Schedule:
Day −6: injection of 2.5 ml of sterile air for air pouch formation.
Day −3: injection of 2.5 ml of sterile air for air pouch maintenance.
Day 0:
Time 0—Intravenous administration of vehicle (Group A), P58 (Group B & C) or Ac2-26 (Group D), immediately before intra-pouch injection of 1 mg zymosan A (Sigma). Another group of mice received P58 (Group E), and a control group received vehicle (Group F), directly into the air-pouch in the absence of zymosan A.
Time+4 h—Air pouches were washed with 2 ml of ice cold PBS containing 3 mM EDTA.

Lavage fluids were kept all the time on ice, then used to determine the number of migrated leukocytes, by taking an aliquot (100 μl) and diluting it 1:10 in Turk's solution (0.01% crystal violet in 3% acetic acid). The samples were then vortexed and 10 μl of the stained cell solution were placed in a Neubauer haematocymometer. Differential cell count was done using a light microscope (Olympus B061). In view of their chromatic characteristics and their nucleus and cytoplasm appearance, polymorphonuclear leukocytes (PMN; >95% neutrophils) could be easily identified.

Experimental Groups:
group A, vehicle (200 μl i.v.)+zymosan A (n=8)
group B, peptide P58 (50-μg i.v.)+zymosan A (n=8)
group C, peptide P58 (200-μg i.v.)+zymosan A (n=8)
group D, peptide Ac2-26 (200-μg i.v.)+zymosan A (n=8)
group E, peptide P58 (100 μg in situ) (n=8)
group F, vehicle (100 μl in situ) (n=5)

FACS Staining and Analysis:
For FACS analyses, an aliquot of lavage fluid was stained with the PE-conjugated anti-GR-1 monoclonal antibody (1:100 dilution, BD Biosciences; Cat 553128) to mark polymorphonuclear leukocytes. Staining was performed at 4° C.

Flow cytometry was performed using FACScan analyser (Becton Dickinson, Cowley, UK) with air-cooled 100 mW argon laser tuned to 488 nm connected to an Apple Macintosh G3 computer running Cell Quest II software. Forward and sidescatter characteristics were initially used to distinguish between the three distinct cell populations (lymphocytes, monocytes and granulocytes). Cells positive for GR-1 were detected in the FL2 channel (wavelength of 548 nm). Data are expressed as percentage of positive cells (in relation to the specific mAb). Determination of positive and negative populations was performed based on the control staining with irrelevant IgG isotype (rat IgG2b) labelled with PE. Once determined, quadrants were rigorously maintained for all analyses.

Statistics:
Data are shown for single mice, and also shown as mean±S.E. of (n) mice per group. Statistical differences were determined by ANOVA, plus Student Newman Keuls test. A P value<0.05 was taken as significant.

Leukocyte Migration:
Intra-pouch challenge with zymosan A triggered a marked leukocyte accumulation into the air-pouches, (as determined by differential cell count). FIG. 23 demonstrates the cumulative data on leukocyte accumulation. This leukocyte accumulation was inhibited significantly by the treatment with Ac2-26 (FIG. 23). Administration of P58 (SEQ ID NO:1) reduced the leukocyte accumulation triggered by zymosan A, 38% and 26% of inhibition for 50 μg and 200 μg/mouse, respectively (FIG. 23). These results did not reach statistical significance (comparing with the vehicle-treated zymosan A), probably due to the small number of animals in each group.

Figure 25:
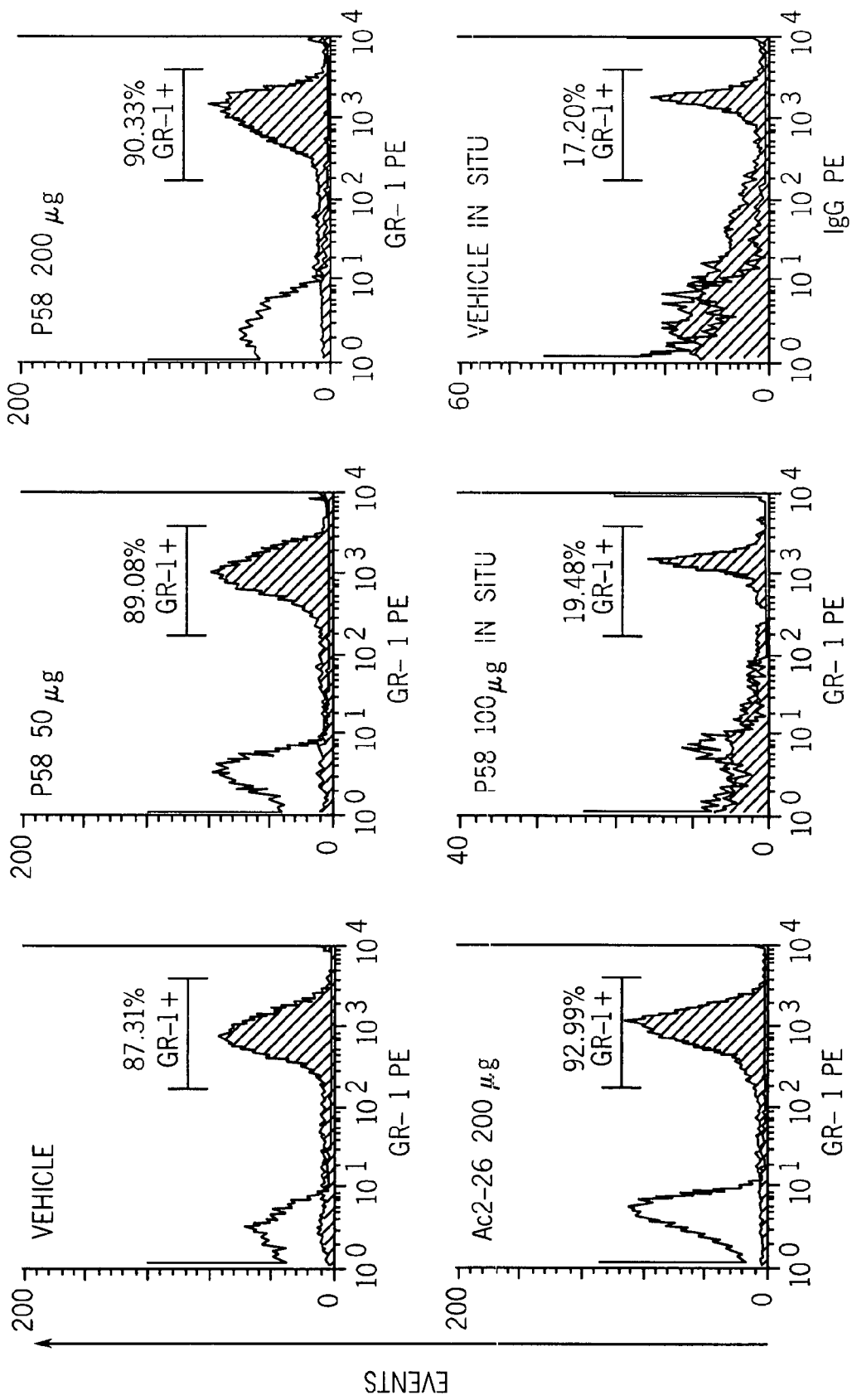
FIG. 25 is a representative flow cytometry histogram for GR-1 staining. Histograms demonstrate a representative staining from one mouse from each of the experimental groups. Grey Line: non specific background staining with IgG labeled with phycoerithrin. Black Histograms show GR-1+ staining. The numbers above the black histograms show the percentage of GR-1+ events in the leukocyte population.

PMNs Migration:
Injection of zymosan A into the air pouch produced a marked neutrophil migration, as determined by FACS analysis with the Gr1 marker. Leukocytes recovered from air pouches were stained for GR-1 as described above. FIG. 24 demonstrates the cumulative data on accumulation of neutrophils (GR-1$^+$ cells). Administration to mice of peptide P58 (SEQ ID NO:1) at 50 μg/mouse inhibited 40% of the neutrophil accumulation triggered by zymosan A ($p<0.05$; FIG. 24). This degree of inhibition is comparable to the 52% of inhibition observed in the group treated with Ac2-26 (200 μg/mouse). The treatment with P58 at 200 μg/mouse led to a lower degree of inhibition (30%) that did not reach statistical significance, perhaps due to the pharmacodynamics of the peptide. Representative FACS histograms are presented in FIG. 25.

Pro-Inflammatory Effects of P58:
The possible pro-inflammatory effects of P58 (SEQ ID NO:1) (100 μg given locally) were evaluated by its injection directly into the mouse air-pouch, and compared with the injection of the same volume (100 μl) of vehicle (sterile pyrogen free PBS). Peptide P58 failed to trigger leukocyte or neutrophil accumulation into the mouse air pouch (FIGS. 23 and 24), suggesting that this peptide does not possess any pro-inflammatory or chemotactic properties. This result also suggests that the peptide preparation was LPS-free.

Conclusions:
This study demonstrates that peptide P58 (SEQ ID NO:1), given at the dose of 50 μg/mouse, is effective in reducing PMN accumulation in an experimental model of cell recruitment, that is in response to local application of zymosan A in the mouse air-pouch cavity. Peptide 58 displayed a significant inhibition at 50 μg/mouse, comparable to the inhibition triggered by the peptide Ac2-26, despite lower inhibition was observed at 200 μg/mouse. It is uncertain if the dose-response profile for peptide P58 reflects unfavorable PK or if it is within the nature of activation of this endogenous receptor (target for P58). Construction of full dose-response curves (e.g. 10-25-50-100 μg/mouse) would allow better assessment of the potency of P58, and possibly also closer comparison to the potency of peptide Ac2-26 and other known anti-inflammatory drugs (e.g. indomethacin, 10 mg/kg).

EXAMPLE 7

The In Vivo Effect of Peptide 58 and its Shorter Derivatives, Peptide 58_4 and Peptide 58_5, on Polymorphonuclear Leukocyte Trafficking The anti-inflammatory activity of P58 shorter derivatives was tested in the same model of acute inflammation used in Example 6, the Zymosan-induced murine dorsal air pouch model.

Animals:
Male out-bred Swiss albino mice were purchased from Harlan, UK (T.O. strain) and maintained on a standard chow pellet diet with tap water ad libitum and a 12:00 h light/dark cycle. All animals were housed for 7 days prior to experimentation to allow body weight to reach ~25 g on the day of the experiment.

Drug Treatment and Experimental Design:

Drugs were stored at −20° C. and defrosted on the day of the experiment. Peptide P58 (SEQ ID NO:1) was provided lyophilized; it was taken back to room temperature and dissolved with sterile PBS before use to make an initial 1 mg/ml solution. Peptide P58-4 (SEQ ID NO:2) was provided lyophilized; it was taken back to room temperature and dissolved with sterile PBS before use to make an initial 327 µg/ml solution. Peptide P58-5 (SEQ ID NO:3) was provided lyophilized; it was taken back to room temperature and dissolved with sterile PBS before use to make an initial 476 µg/ml solution. Vehicle consisted of sterile pyrogen free PBS (Gibco, cat no. 14190-094). Once dissolved, peptides P58 (SEQ ID NO:1), P58-4 (SEQ ID NO:2) and P58-5 (SEQ ID NO:3) gave a clear solution. Drugs or vehicle were administered i.v. at a final volume of 200 µl in the doses described below.

Experimental Schedule:

Day −6: injection of 2.5 ml of sterile air for air pouch formation.

Day −3: injection of 2.5 ml of sterile air for air pouch maintenance.

Day 0:

Time 0—Intravenous administration of vehicle (Group A), P58 (SEQ ID NO:1) (Group B & C), P58-4 (SEQ ID NO:2) (Group D & E), P58-5 (SEQ ID NO:3) (Group F & G) immediately before intra-pouch injection of 1 mg zymosan A (Sigma).

Time+4 h—Air pouches were washed with 2 ml of ice cold PBS containing 3 mM EDTA and 25 U/mL of Heparin.

Lavage fluids were kept all the time on ice, then used to determine the number of migrated leukocytes, by taking an aliquot (100 µl) and diluting it 1:10 in Turk's solution (0.01% crystal violet in 3% acetic acid). The samples were then vortexed and 10 µl of the stained cell solution were placed in a Neubauer haematocymometer. Differential cell count was done using a light microscope (Olympus B061). In view of their chromatic characteristics and their nucleus and cytoplasm appearance, polymorphonuclear leukocytes (PMN; >95% neutrophils) could be easily identified.

Experimental Groups:

group A, vehicle (200 µl i.v.)+zymosan (n=7)
group B, peptide P58 (200 µg; 80 nmole i.v.)+zymosan (n=7)
group C, peptide P58 (50 µg; 20 nmole i.v.)+zymosan (n=7)
group D, peptide P58-4 (65.4 µg; 80 nmole i.v.)+zymosan (n=7)
group E, peptide P58-4 (16.35 µg; 20 nmole i.v.)+zymosan (n=7)
group F, peptide P58-5 (95.2 µg; 80 nmole i.v.)+zymosan (n=7)
group G, peptide P58-5 (24 µg; 20 nmole i.v.)+zymosan (n=7)

FACS Staining and Analysis:

For FACS analyses, an aliquot of lavage fluid was stained with the PE-conjugated anti-GR-1 monoclonal antibody (1:100 dilution, eBiosciences; Cat 11-5931) to mark polymorphonuclear leukocytes. Staining was performed at 4° C. Flow cytometry was performed using FACScan analyser (Becton Dickinson, Cowley, UK) with air-cooled 100 mW argon laser tuned to 488 nm connected to an Apple Macintosh G3 computer running Cell Quest II software. Forward and sidescatter characteristics were initially used to distinguish between the three distinct cell populations (lymphocytes, monocytes and granulocytes). Cells positive for GR-1 were detected in the FL2 channel (wavelength of 548 nm). Data are expressed as percentage of positive cells (in relation to the specific mAb). Determination of positive and negative populations was performed based on the control staining with irrelevant IgG isotype (rat IgG2b) labelled with PE. Once determined, quadrants were rigorously maintained for all analyses.

Statistics:

Data are shown for single mice, and also shown as mean±S.E. of (n) mice per group. Statistical differences were determined by ANOVA, plus Student Newman Keuls test. A P value<0.05 was taken as significant.

Leukocyte Migration:

Intra-pouch challenge with zymosan A triggered a marked leukocyte accumulation into the air-pouches (as determined by differential cell count). Administration of P58 (SEQ ID NO:1) reduced the leukocyte accumulation triggered by zymosan A, 47% and 33% of inhibition for 20 nmole and 80 nmole/mouse, respectively (FIG. 26). Administration of peptide P58-4 (SEQ ID NO:2), reduced the leukocyte accumulation triggered by zymosan A, 35% and 47% of inhibition for 20 nmole and 80 nmole/mouse, respectively (FIG. 26), while administration of peptide P58-5 (SEQ ID NO:3), a 9 amino acid peptide derived from P58 (SEQ ID NO:1) reduced the leukocyte accumulation triggered by zymosan by 29% at 80 nmole, but did not inhibit leukocyte migration when administered at 20 nmole/mouse (FIG. 26).

PMN Migration:

Injection of zymosan into the air pouch produced a marked neutrophil migration, as determined by FACS analysis with the Gr1 marker. FIG. 27 demonstrates the cumulative data on accumulation of neutrophils (GR-1$^+$ cells). Administration of peptide P58 (SEQ ID NO:1) at 20 nmole/mouse or 80 nmole/mouse inhibited the zymosan-induced neutrophil accumulation by 50% (p<0.05) or 29%, respectively (FIG. 27). Administration of P58-4 (SEQ ID NO:2) at 20 nmole/mouse or 80 nmole/mouse inhibited neutrophil migration by 35% or 49%, respectively (FIG. 27). P58-5 had a weak effect only at 20 nmole/mouse (FIG. 27).

Conclusions:

This study demonstrates that peptides P58 (SEQ ID NO:1) and P58-4 (SEQ ID NO:2) are capable of reducing PMN accumulation in an experimental model of cell recruitment in response to local application of zymosan in the mouse air pouch cavity, with different potencies and efficacies. P58-5 (SEQ ID NO:3) displayed only a weak effect. Peptide P58 (SEQ ID NO:1) (20 nmole/mose) and peptide P58-4 (SEQ ID NO:2) at 80 nmole/mouse displayed ~50% inhibition of neutrophils accumulation in the pouch, which is the maximal effect expected in such biological system, indicating that these peptides show biological activity in an animal model of acute inflammation.

EXAMPLE 8

The In Vivo Effect of Peptide 58 (SEQ ID NO:1) and its Shorter Derivative, Peptide 58_4 (SEQ ID NO:2) on Myocardial Infarct Following Ischaemia-Reperfusion This Example relates to testing the ability of P58 and its shorter derivative of the present invention to afford protection in murine acute myocardial infarct following ischaemia-reperfusion. Known agonists of the FRPRL1 receptor have been shown to have a protective effect in a murine model of myocardial ischemia-reperfusion (La et al 2001, FASEB J. 15, 2247-2256; Gavins et al 2005, FASEB J. 19, 100-102). This model is thus being used to test the ability of P58 and its shorter derivative to afford protection in murine acute myocardial infarct.

Male Albino mice (~30 g; n=6/group) are subjected to ischemia-reperfusion by occlusion of the LADCA (left anterior descending coronary artery) for 25 min (ischemia) followed by reopening of LADCA (reperfusion) for 60 min. Peptides are administered i.v. at onset of reperfusion at different doses, ranging from 5 to 80 nmoles/mouse. The myocardial tissue damage is assessed by measuring the infarct size (using p-nitro-blue tetrazolium) and area at risk (using Evans blue dye). The results indicate the ability of the peptides to protect against experimental myocardial ischemia-reperfusion.

EXAMPLE 9

The Effect of P61_S, P61-dimer (P61_D), P33_V and P33-dimer (P33_D) in Aortic Rings from Wistar Rats and the Participation of Nitric Oxide (NO) in this Effect This Example relates to testing the ability of P61_S, P61-dimer (P61_D), P33_V and P33-dimer (P33_D) peptides of the present invention to exert an NO-dependent vasodilating effect on murine aortic rings. Known agonists of the Mas receptor, i.e. Ang(1-7) and AVE 0991, have been previously shown to have an NO-dependent vasodilating effect on murine aortic rings, which was also dependent on intact endothelium (Lemos et al 2005, J. Cardiovasc. Pharmacol. 46, 274-279; Santos et al 2003, Hypertension 41, 737-743). The ability of Mas-agonistic peptides of the present invention to exert such an effect was tested in this model.

The objectives of this study were as follows:
1. To determine the effect of P61_S (SEQ ID NO:10), P61_D (SEQ ID NO:9), P33_V (SEQ ID NO:7) and P33_D (SEQ ID NO:6) on isolated rings of rat aorta.
2. To evaluate the role of endothelium in the vascular effects of P61_S (SEQ ID NO:10), P61_D (SEQ ID NO:9), P33_V (SEQ ID NO:7) and P33_D (SEQ ID NO:6) on rings of rat aorta.
3. To evaluate the participation of NO (Nitric Oxide) in the vascular effects of P61_S (SEQ ID NO:10), P61_D (SEQ ID NO:9), P33_V (SEQ ID NO:7) and P33_D (SEQ ID NO:6) on rings of rat aorta.

For comparison, the effects of Angiotensin 1-7 [Ang-(1-7)] were also determined.

Test System Animal Information Description

Male Wistar rats of the age of 13-14 weeks (body weight: 250 to 300 g) were used. The rats were exposed to light-dark cycle of 12 hs (day—06:00 to 18:00; night—18:00 to 06:00) controlled by timer. Rats were killed by decapitation and exsanguination and tissues were rapidly removed.

Rat Aortic Rings Preparation and Mounting

Rings (3-4 mm) from the descending thoracic aorta, free of adipose and connective tissue, were set up in gassed (95% O2 and 5% CO2) Krebs-Henseleit solution (mmol/L): NaCl 110.8, KCl 5.9, NaHCO3 25.0, MgSO4 1.07, CaCl2 2.49, NaH2PO4 2.33 and glucose 11.51, at 37° C., under a tension of 1.0 g, for 1 hour to equilibrate. The presence of functional endothelium was assessed by the ability of Acetylcholine (1 µM) to induce more than 70% relaxation of vessels pre-contracted with phenylephrine (0.3 µM) (Lemos et al., 2005). When necessary, the endothelium was removed by rubbing the intimal surface with a wooden stick. Mechanical activity, recorded isometrically by a force transducer (Panlab, model number TR1210, Spain), was fed to an amplifier-recorder (Powerlab 4/20, ADInstruments, Inc.) and to a personal computer equipped with an analogue-to-digital converter board (AD16JR; World Precision Instruments, Inc.), using CVMS data acquisition/recording software (World Precision Instruments, Inc.).

Experimental Protocol

The vasorelaxant activity of peptides —P61_S (SEQ ID NO:10), P61 (SEQ ID NO.9)-dimer (P61_D), P33_V (SEQ ID NO:7) and P33 (SEQ ID NO:6)-dimer (P33_D) were measured in vessels (N=5-8) with or without functional endothelium pre-contracted to the same tension level (approximately 1.5 g of tension) induced by submaximal concentrations of phenylephrine (0.01 µM). For comparison, the effect of Ang-(1-7) was also tested (N=4)

P61_S (SEQ ID NO:10), P61 (SEQ ID NO$_9$)-dimer (P61_D), P33_V (SEQ ID NO:7) or P33 (SEQ ID NO:6)-dimer (P33_D) were added in increasing cumulative concentrations (0.0001 to 1 µM) once the response to phenylephrine had stabilized (FIG. 28). In order to verify the participation of endothelium-derived products in the relaxant effect of peptides, experiments were performed in the presence of 100 µM N'-Nitro-L-Arginine Methyl Ester-[L-NAME]—a nonselective inhibitor of nitric oxide synthase. In experiments performed in the presence of L-NAME, vessels were pre-contracted with 0.03 µM of phenylephrine, to achieve the same tension level as the others. L-NAME was added to the bath 20 min prior to the addition of phenylephrine.

Statistical Analysis

Results are presented as mean±SEM. Two-way analysis of variance (ANOVA) with Bonferroni multiple comparison post-test was used to compare concentration response curves obtained in aortic rings. The vasodilator effect of P61_S (SEQ ID NO:10), P61 (SEQ ID N09)-dimer (P61_D), P33_V (SEQ ID NO:7), P33 (SEQ ID NO:6)-dimer (P33_D) and Ang-(1-7) were expressed as percentage decrease in maximal contraction induced by phenylephrine. All statistical analyses were considered significant when p<0.05.

Results

Figure 29:
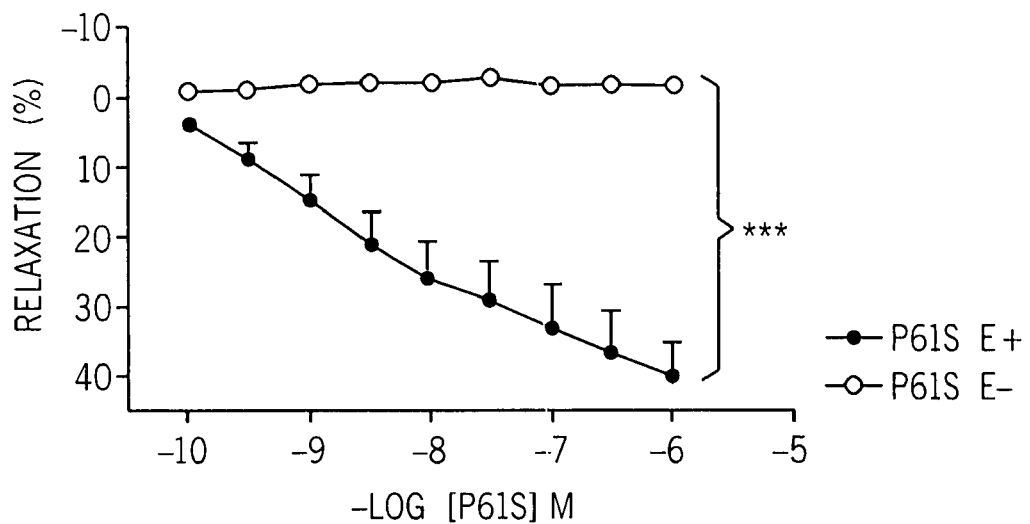
FIG. 29 is a graph demonstrating the vasodilator effect of P61_S in aortic rings from Wistar rat containing (E+) or lacking functional endothelium (E−). Each point represents the mean±SEM generated from at least 6 separated experiments ***p<0.001.

In endothelium-containing aortic rings pre-contracted with phenylephrine, P61_S (SEQ ID NO:10) produced a concentration-dependent vasodilator effect (FIG. 29). The vasorelaxation induced by P61_S (SEQ ID NO:10) was abolished in endothelium-denuded vessels (FIG. 29). Maximal values (%) for the relaxant effect of P61_S (Emax) were 39.99±5.034 for vessels with endothelium.

Figure 30:
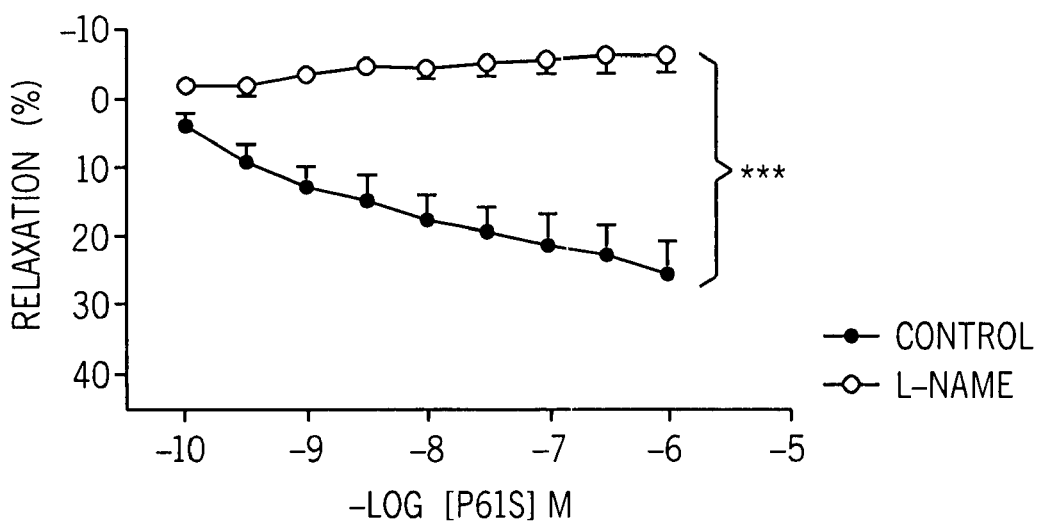
FIG. 30 is a graph depicting the vasodilator effect of P61_S in aortic rings from Wistar rat in the absence (control) or presence of L-NAME, a NO synthase inhibitor. Each point represents the mean±SEM generated from at least 5 separated experiments ***p<0.001.

To study the participation of NO in the relaxation induced by P61_S, additional experiments were performed in the presence of the NO synthase inhibitor, L-NAME. The results, shown in FIG. 30, indicate that inhibition of NO synthase abolished the vasodilator effect of P61_S.

Figure 31:
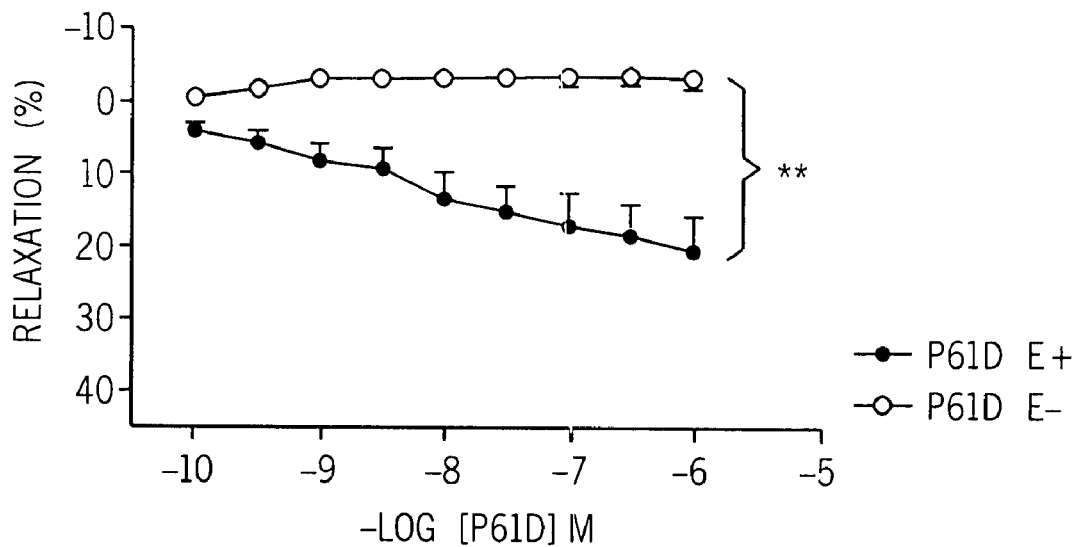
FIG. 31 is a graph showing the vasodilator effect of P61_D in aortic rings from Wistar rat containing (E+) or lacking functional endothelium (E−). Each point represents the mean±SEM generated from at least 8 separated experiments **p<0.01.

FIG. 31 shows the endothelium-dependent vasodilator effect induced by P61_D (SEQ ID NO:9) in rat aortic rings. This effect was abolished in the absence of functional endothelium. Maximal values (%) for the relaxant effect of P61_D (Emax) were 20.45±5.11 for vessel with endothelium.

Figure 32:
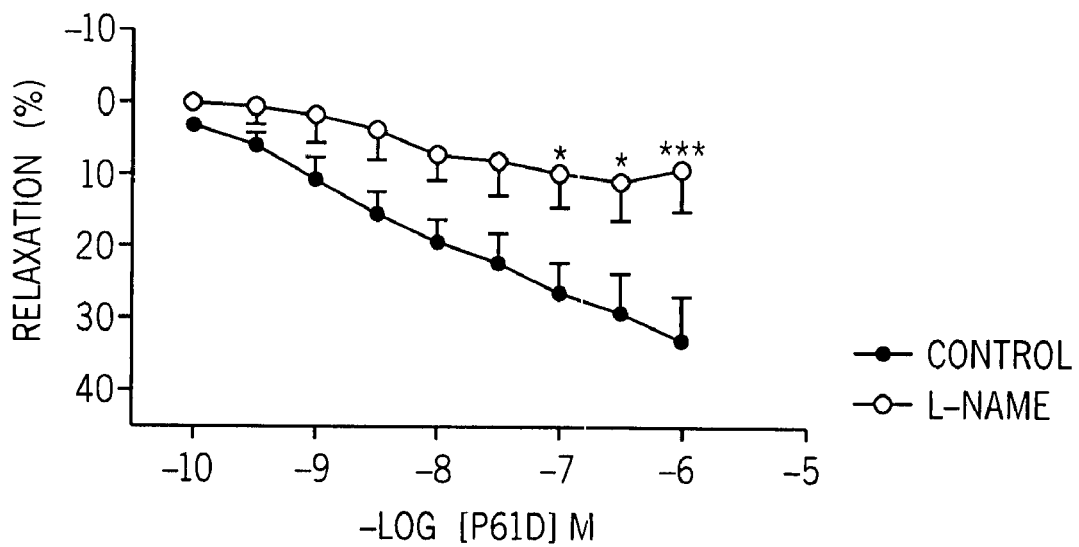
FIG. 32 is a graph illustrating the vasodilator effect of P61_S in aortic rings from Wistar rat in the absence (control) or presence of L-NAME. Each point represents the mean±SEM generated from at least 5 separated experiments *p<0.05; ***p<0.001.

In order to evaluate whether NO participates in the response induced by P61_D, the vasodilator effect of this peptide was tested in the presence of L-NAME. As shown in FIG. 32, after blockade of NO synthase, the endothelium-dependent relaxation induced by P61_D (SEQ ID NO:9) was markedly inhibited, although a residual vasorelaxation was observed at the higher concentrations of P61_D.

Figure 33:
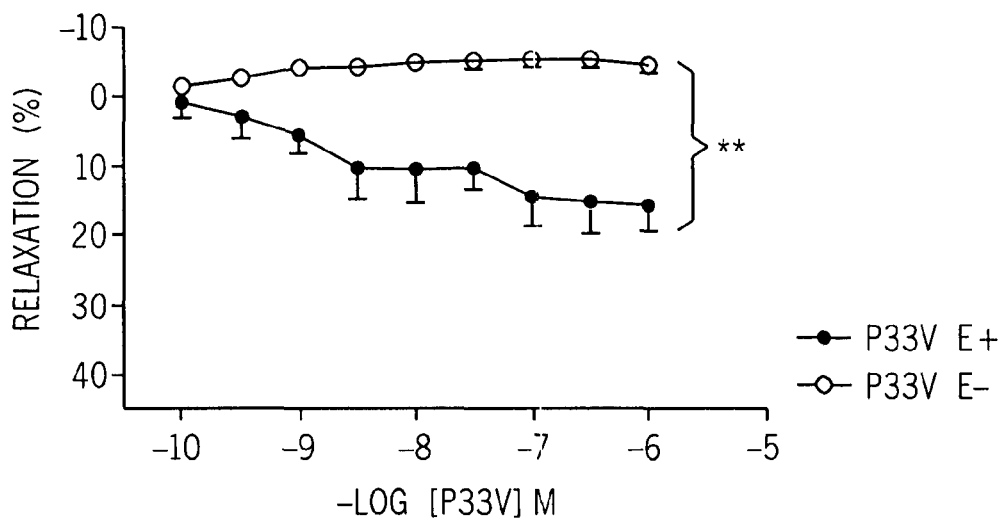
FIG. 33 is a graph demonstrating the vasodilator effect of P33_V in aortic rings from Wistar rat containing (E+) or lacking functional endothelium (E−). Each point represents the mean±SEM generated from at least 6 separated experiments **p<0.01.

FIG. 33 shows the vasodilator effect induced by P33_V (SEQ ID NO:7) in rat aortic rings. This effect was completely dependent on a functional endothelium. Maximal values (%) for the relaxant effect of P33_V (Emax) were 15.69±3.66 for vessels with endothelium.

Figure 34:
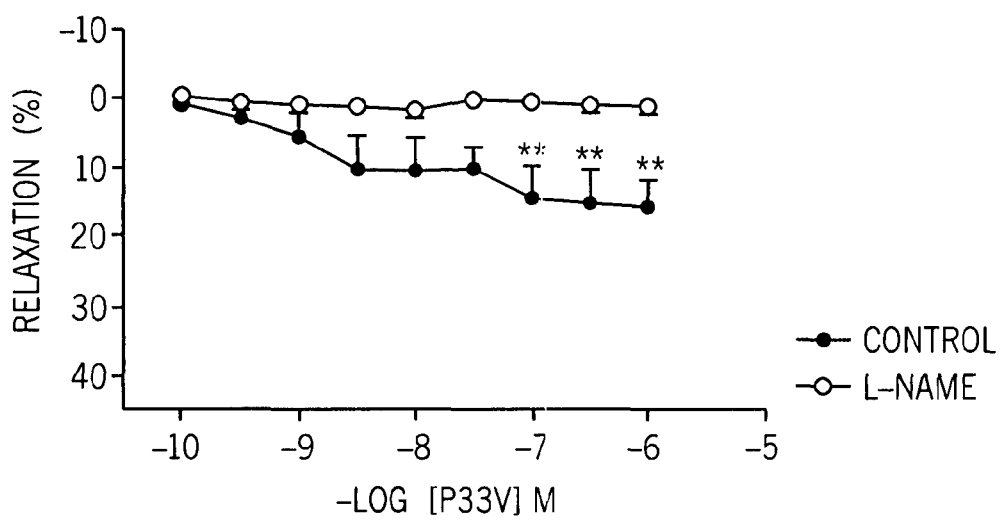
FIG. 34 is a graph depicting the vasodilator effect of P33_V in aortic rings from Wistar rat in the absence (control) or presence of L-NAME. Each point represents the mean±SEM generated from at least 6 separated experiments **p<0.01.

To study the participation of NO in the vasorelaxation induced by P33_V (SEQ ID NO:7), its effect was tested in the presence of L-NAME. After blockade of NO synthase the endothelium-dependent relaxation induced by P33_V was completely inhibited (FIG. 34).

Figure 35:
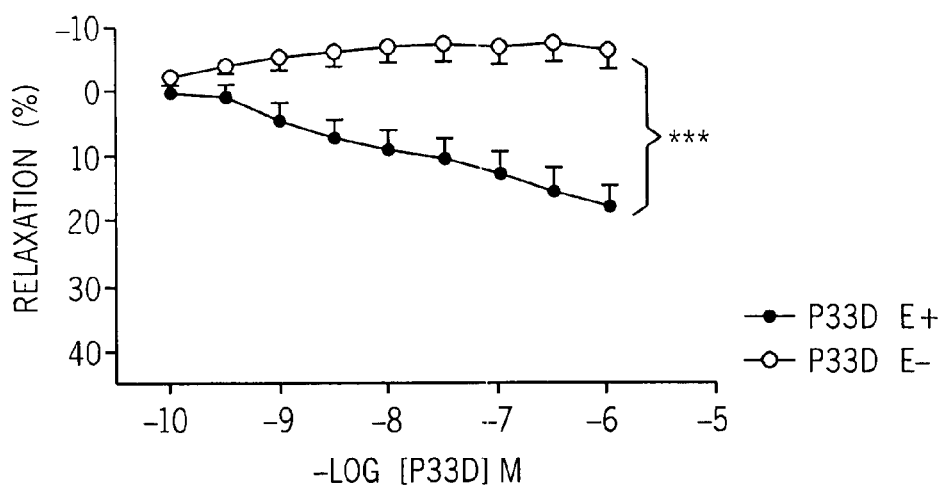
FIG. 35 is a graph showing the vasodilator effect of P33_D in aortic rings from Wistar rat containing (E+) or lacking functional endothelium (E−). Each point represents the mean±SEM generated from at least 6 separated experiments ***p<0.001.

FIG. 35 shows that P33_D induced vasodilator effect in rat aortic rings. This effect was completely inhibited in the absence of a functional endothelium. Maximal values (%) for the relaxant effect of P33_D (Emax) were 17.78±3.43 for vessels with endothelium.

Figure 36:
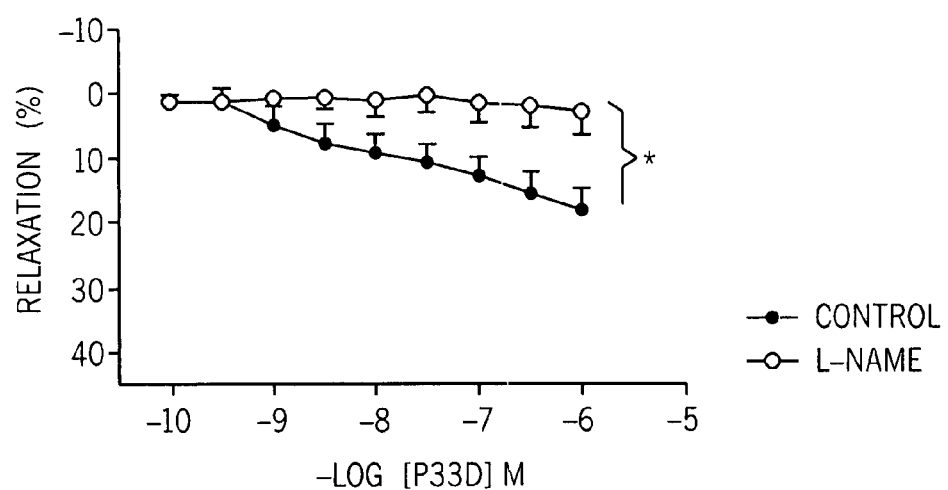
FIG. 36 is a graph illustrating the vasodilator effect of P33_D in aortic rings from Wistar rat in the absence (control) or presence of L-NAME. Each point represents the mean±SEM generated from at least 5 separated experiments *p<0.05.

To verify the participation of NO in the vasodilator effect of P33_D (SEQ ID NO:6), its effect was tested in the presence of L-NAME. After the inhibition of NO synthase, the effect of P33_D was completely inhibited (FIG. 36).

Figure 37:
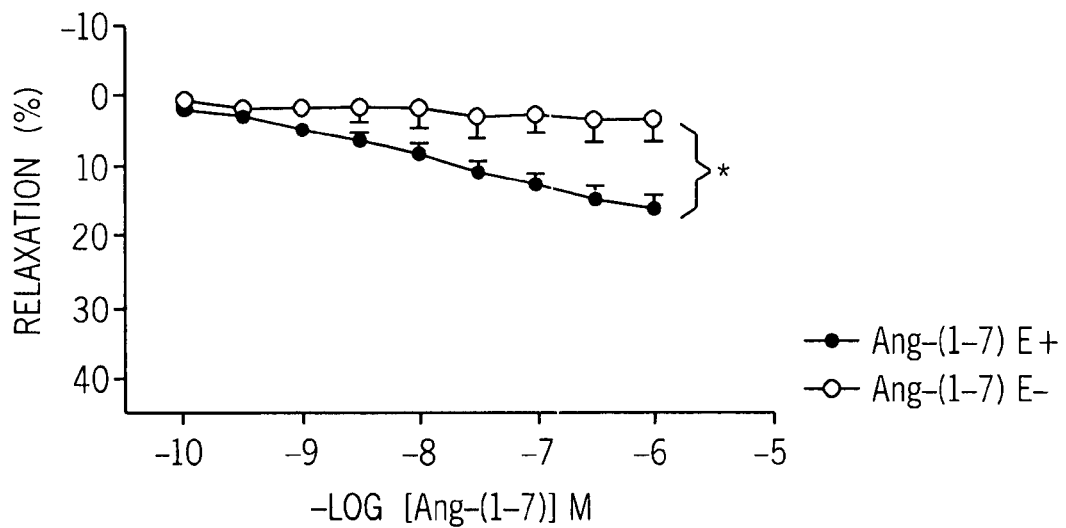
FIG. 37 is a graph showing the vasodilator effect of Ang-(1-7) in aortic rings from Wistar rat containing (E+) or lacking functional endothelium (E−). Each point represents the mean±SEM generated from at least 4 separated experiments *p<0.05.

FIG. 37 shows the effect induced by Ang-(1-7) in aortic rings from Wistar rats. This effect was abolished in the absence of functional endothelium. Maximal values (%) for the relaxant effect of Ang-(1-7) (Emax) were 15.64±1.91 and 2.82±3.11 for vessels with and without endothelium, respectively.

Figure 38:
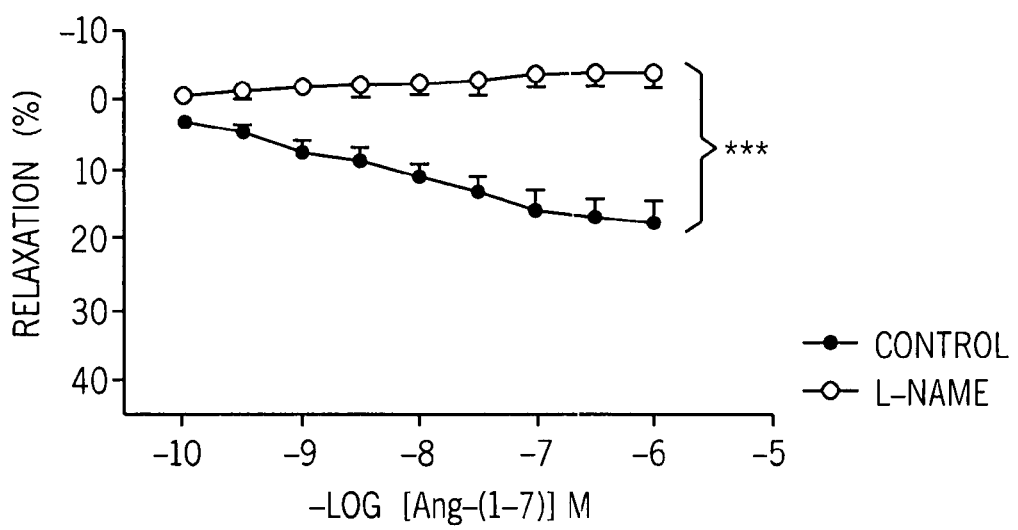
FIG. 38 is a graph demonstrating the vasodilator effect of Ang-(1-7) in aortic rings from Wistar rat in the absence (control) or presence of L-NAME. Each point represents the mean±SEM generated from at least 5 separated experiments ***p<0.001.

To study the participation of NO in the relaxation induced by Ang-(1-7), additional experiments were performed in the presence of the NO synthase inhibitor (L-NAME). After blockade of NO synthase the endothelium-dependent relaxation induced by Ang-(1-7) was completely inhibited (FIG. 38).

In summary, P61_S, P61_D, P33_V and P33_D induced a concentration-dependent vasodilator effect in aortic rings from Wistar rats. The response induced by these peptides was dependent on the presence of endothelium. The effect of the peptides P61_S, P33_V and P33_D was blocked in the presence of L-NAME. The vasodilator effect induced by P61_D was partially but significantly reduced in the presence of L-NAME. The results indicate that in the aorta of Wistar rats, the vasodilator effect of P61_S, P61_D, P33_V and P33_D is dependent on endothelium-derived NO.

For comparison, the effect of Ang-(1-7) was also tested. In aorta of Wistar rats Ang-(1-7) induced a vasodilator effect. This response was dependent on endothelium and NO. These results are in accordance with several other reports from the literature showing that the vasodilator effect of Ang-(1-7) was dependent on endothelium-derived NO (Le tran & Forster, 1997; Silva et al., 2007).

The peptides P61_S, P61-dimer (P61_D), P33_V, and P33-dimer (P33_D) induced an NO— and endothelium-dependent vasodilator effect in isolated aortic rings from Wistar rats.

EXAMPLE 10

The Participation of D-Pro$^7$-Ang 1-7 Sensitive Mechanism in the Relaxant Effect of Peptides P61_S, P61_D, P33_V, and P33_D In order to verify the participation of Mas-specific pathway in the in the relaxant effect of peptides P61_S (SEQ ID NO:10), P61-dimer (P61_D) (SEQ ID N09), P33_V (SEQ ID NO:7), P33-dimer (P33_D) (SEQ ID NO:6), the above-mentioned experiments are repeated in the presence of D-Pro$^7$-Ang 1-7, a known Mas-specific antagonist (Lemos et al 2005, J. Cardiovasc Pharmacol 46, 274-279; Santos et al. 2003, Hypertension 41, 737-743).

The vasorelaxant activity of peptides is measured in vessels with or without functional endothelium pre-contracted to the same tension level (approximately 1.5 g of tension) induced by submaximal concentrations of phenylephrine (0.03 μM or 0.1 μM). Peptides are added in increasing cumulative concentrations (0.0001 to 1 μM) once the response to phenylephrine had stabilized. In order to verify the participation of D-Pro$^7$-Ang 1-7 sensitive mechanism in the relaxant effect of Peptides, experiments are performed in the presence of D-Pro$^7$-Ang 1-7 (10-6 M). As a control for this protocol, another vessel segment from each rat is simultaneously monitored for Peptides effects alone. As positive control, cumulative concentration response curves to Ang-(1-7) are constructed in presence and absence of D-Pro$^7$-Ang 1-7.

EXAMPLE 11

The Effect of P61_S, P61-dimer (P61_D), P33_V and P33-dimer (P33_D) Following Ischemia-Reperfusion of Isolated Rat Hearts This Example relates to testing the effect of P61_S, P61-dimer (P61_D), P33_V and P33-dimer (P33_D) Following Ischemia-reperfusion of Isolated Rat Hearts. Ang(1-7) has been previously shown to improve the post-ischemic function of isolated murine hearts, as manifested by parameters such as coronary blood flow, reperfusion arrhythmias and mechanical cardiac function (Ferreira et al 2002, Brazilian J. of Med. And Biol. Res. 35, 1083-1090; Ferreira et al 2001, Hypertension 38, 665-668; Mello 2004, J. of Renin-Angiotensin-Aldosterone System 5, 203-208).

The effect of the peptides P61_S (SEQ ID NO:10), P61-dimer (P61_D) (SEQ ID N09), P33_V (SEQ ID NO:7), P33-dimer (P33_D) (SEQ ID NO:6) on the coronary blood flow, reperfusion arrhythmias and the mechanical function of rat isolated perfused hearts is evaluated using the Langendorff preparation (N=6 for each dose) of adult (12-14 weeks old) Wistar rats.

Animals Acclimatization

The rats are maintained in the animal facilities for at the most 7 days before the beginning of the experiment. The animals are exposed to a brightness circle of light-dark cycle of 12 hs (day—06:00 to 18:00; night—18:00 to 06:00) and the room temperature is kept at 23±2° C.

Isolated Heart Technique—Ischemia/Reperfusion

For the isolated perfused heart technique, the rats are decapitated 10-15 minutes after intraperitoneal injection of 400 IU heparin, the thorax is opened and the heart is carefully dissected and perfused through an aortic stump with Krebs-Ringer Solution (KRS) containing (in mmol/L): NaCl (118.4), KCl (4.7), KH2PO4 (1.2), MgSO4.7 H2O (1.2), CaCl2.2 H2O (2.5), Glucose (11.7), NaHCO3 (26.5). The perfusion pressure is maintained constant (65 mmHg) at 37±1° C. and constant oxygenation (5% CO2 and 95% O2). A force transducer is attached through a heart clip to the apex of the ventricles to record the contractile force (tension, g) on a computer, through a data-acquisition system (Biopac System, Santa Barbara, Calif.). A diastolic tension of 1 g is applied to the hearts. Electrical activity is recorded by using the data-acquisition system with the aid of two electrodes place directly on the surface of the right atrium and left ventricle (bipolar lead). The heart rate is calculated from the force records. Coronary flow is measured by collecting the perfusate over a period of 1 minute at regular intervals. After 15 minutes of the equilibration period, the hearts are perfused with the peptides solutions for an additional 20 min period. After this baseline period the left anterior descending coronary artery (LAD) is ligated. The ligature is released after 15 minutes, and reperfusion is performed for an additional 30 minutes.

Cardiac arrhythmias are defined as the presence of ventricular tachycardia and/or ventricular fibrillation after the ligature of the coronary artery is released. To obtain a quantitative measurement, the arrhythmias are graded by their duration, with duration of 30 minutes considered as irreversible arrhythmia. Therefore, the occurrence of cardiac arrhythmias for up to 3 minutes is assigned a factor 2; 3 to 6 minutes is assigned a factor 4; 6 to 10 minutes is assigned a factor 6; 10 to 15 minutes is assigned a factor 8; 15 to 20 minutes is assigned a factor 10; 20 to 25 minutes is assigned a factor 11; and 25 to 30 minutes is assigned a factor 12. A value of 2 to 12 is thus obtained in each experiment and is denoted as arrhythmia severity index (ASI).

Experimental Groups: the hearts are perfused with: KRS (control group, N=6) or KRS containing the peptide (0.04, 1 and 5 nmol/L, N=6 for each dose).

Statistical Analysis All data are expressed as mean±SEM. The cardiac function values of each animal are obtained by the average of the values collected at 5 minutes interval during the baseline and experimental period. Statistical significance is estimated using one-way ANOVA followed by Dunnett's post hoc test (GraphPad Prism 4.0). The level of significance is set at P<0.05.

EXAMPLE 12

Effect of P61_S, P61-dimer (P61_D), P33_V and P33-dimer (P33_D) on Cardiac Remodeling Induced by Isoproterenol The effect of the peptides P61_S (SEQ ID NO:10), P61-dimer (P61_D) (SEQ ID N09), P33_V (SEQ ID NO:7), P33-dimer (P33_D) (SEQ ID NO:6) on cardiac remodeling, was tested by determining their effect on heart hypertrophy and fibrosis (deposition of collagen I, III, and fibronectin) induced by Isoproterenol. Losartan (an antagonist of the known angiotensin II receptor, AT1, Kucharewicz et al., 2002; Hypertension, (40): 774-779) was used as positive control. The negative control group was treated with vehicle only. Additional control groups included rats not-treated with isoproterenol which were treated with the peptides, with Losartan or with the vehicle. The analysis included determination of the left ventricle mass and morphometry. In addition, immunofuorescence analysis of fibronectin and collagens I and III deposition was performed by confocal microscopy.

Animals Acclimatization: Male Wistar rats Age: 13-14 weeks (250 to 300 g) were maintained in the animal facilities for 7 days before the beginning of the experiment. The animals were exposed to a brightness circle of light-dark cycle of 12 hs (day—06:00 to 18:00; night—18:00 to 06:00), and the room temperature was kept at 23±2° C.

Experimental Design and Procedures

Heart failure was induced by daily injections of isoproterenol (2 mg/kg/day, subcutaneously) during 7 days. The rats were divided to the following groups: The groups treated with 0.9% NaCl instead of isoproterenol (i.e. no induction of remodeling) were each N=4, and consisted of: control (0.9% NaCl subcutaneously plus water by gavage); control-Losartan (0.9% NaCl subcutaneously plus Losartan 1 mg/Kg once a day, by gavage), control-peptide (0.9% NaCl subcutaneously plus P61_S or P61_D or P33_V or P33_D, 1 ug/hour/Kg by osmotic minipump, for each peptide). The groups that were treated with isoproterenol were N=6 each, and consisted of: ISO (isoproterenol plus water by gavage), ISO+Losartan (isoproterenol plus Losartan, 1 mg/kg once a day, by gavage), ISO plus Peptide (Isoproterenol plus peptide P61_S or P61_D or P33_V or P33_D, 1 ug/hour/Kg, by osmotic minipump, for each peptide). The final volume of gavage and subcutaneous injection was approximately 0.5 ml and 0.1 ml, respectively.

Immunostaining and Confocal Microscopy

Immunofluorescence-labeling and quantitative confocal microscopy was used to investigate the distribution and quantity of collagen types I, III and fibronectin present in the left ventricles. Hearts were collected from control and Isoproterenol-treated animals, washed in phosphate-buffered saline (PBS) to remove excess blood, and then cryofixed in a –80° C. solution of 80% methanol and 20% dimethyl sulfoxide. Samples were stored (i.e. cryosubstituted) at –80° C. for 5-7 days, moved to –20° C. for one day, washed three times in absolute ethanol at room temperature, twice in xylene and then embedded in paraffin following standard methods. 5-8 µm thick sections were mounted on slides, deparaffinized with xylene, rehydrated through a graded series of ethanol to PBS and then incubated in blocking solution (1% BSA and 0.1% Tween 20 in PBS) at room temperature for 1 hr.

Sections were incubated overnight at 4° C. with one of the following primary antibodies: rabbit anti-human collagen type I, rabbit anti-human collagen type III or rabbit anti-human fibronectin. All antibodies were diluted with 1:10 diluted blocking solution. After 4-5 rinses in PBS, donkey anti-rabbit IgG conjugated with Cy3 (cat #711-165-152, Jackson ImmunoResearch Laboratories) or were added for 1 hr in the dark at room temperature. Following washes with PBS, sections were mounted in 90% glycerol/10% TRIS 1M, pH 9.0 and viewed with a laser scanning confocal microscope (Zeiss 510Meta). Optimal confocal settings (aperture, gain and laser power) were determined at the beginning of each imaging session and then held constant during the analysis of all the samples. Nuclei were labeled with 4'6-diamidino-2-phenylindole dihydrochloride (DAPI) cat #D1306—Molecular Probes. For quantitative analysis of collagens I, III, and fibronectin, the ImageTool 2.0 image analysis program was used (http://ddsdx.uthscsa.edu/dig/itdesc.html) to measure the fluorescence intensity in images randomly selected. Images were captured at 12 bit and analyzed in the gray scale range of 0 to 255. Fluorescence intensity was measured as an average of the area (i.e., the sum of gray values of all pixels divided by the number of pixels in the area) and values recorded as arbitrary units (AU). Background fluorescence was measured and subtracted from the region of interest.

Diameter of Cardiomyocytes Determined by Histological Analysis

The diameter of each cardiomyocyte is also a measure of cardiac hypertrophy. In order to measure the diameter of cardiomyocytes upon remodeling by isoproterenol, and the effect of our peptides on this process, left ventricles are left in 4% Bouin fixative for 24 hours at room temperature. The tissues are dehydrated by sequential washes with 70% ethanol, 80% ethanol, 90% ethanol, and 100% ethanol and imbedded in paraffin. Transversal sections (6 µm) are cut starting from the base area of the left ventricle at intervals of 40 µm and dyed with hematoxilin-eosin stain. Myocytes diameter are evaluated in tissue sections (3-4 for each animal) using an ocular micrometer calibrated with a stage micrometer adapted to a light microscope (BX 60, Olympus) at 400× magnification. Only cardiomyocytes cut longitudinally with nuclei and cellular limits visible are used for analysis (an average of 30 cardiomyocytes for each slice). The diameter of each myocyte is measured across the region corresponding to the nucleus. Fifty to one hundred cardiomyocytes are analyzed for each animal (n=4-6 different animals). These results were not obtained yet.

Statistical Analysis

Data was reported as mean±SEM. Statistical analysis for confocal microscopy was performed using unpaired Student's t test followed by the Mann Whitney test. Unpaired Student's t test is used for the analysis of cardiomyocytes. p values of 0.05 or less were considered significant.

Results

Hearts from control and Isoproterenol-treated animals were collected, and the left ventricle mass was determined Results showing the left ventricle to body mass ratio (LV/BW) are presented in in FIGS. 46-50. The Isoproterenol treatment caused an increase in the left ventricle to body mass ratio in all of the above groups (FIGS. 46-50). None of the peptides reduced the Isoproterenol induced raise in the left ventricle to body mass ratio. The positive control, Losartan, did not have an effect either.

The effect on cardiac remodeling can be analyzed more directly by checking heart hypertrophy as measured by Fibronectin and Collagen I and III deposition. Thus, this assay, which is more sensitive than the analysis of left ventricle mass, was carried out. At the time of submission of this application, the data of only 3 out of 6 animals of each group was analysed. The partial data obtained for P61_D and P61_S are shown in FIGS. 40-45 and demonstrates the effect of these two peptides on cardiac hypertrophy as measured by deposition of Fibronectin, Collagen I and Collagen III following isoproterenol cardiac remodeling. The results indicate that P61_D and P61_S are effective in reducing the heart hypertrophy induced by Isoproterenol, as indicated by deposition fibronectin; Collagen I and Collagen III (albeit P61_D effect as measured by Fibronectin deposition was not significant, FIG. 40).

The partial data obtained for P33_V was inconsistent (not shown), and the analysis is to be completed when the data of all animals in this group is obtained. No data were obtained for P33_D at the time of submission of this application.

The descriptions given are intended to exemplify, but not limit, the scope of the invention. Additional embodiments are within the claims

---

What is claimed is:

1. A peptide consisting of less than 30 amino acids in length, said peptide comprising the amino acid sequence as set forth in SEQ ID NO: 29.

2. The peptide of claim 1, wherein the peptide is selected from the group consisting of:
FLGYCIYLNRKRRGDPAFKRRLRD (SEQ ID NO. 9),
FLGYSIYLNRKRRGDPAFKRRLRD (SEQ ID NO. 10),
FAFLGYSIYLNRKRRGDPAF (SEQ ID NO. 12),
FAFLGYCIYLNRKRRGDPAF (SEQ ID NO. 13),
FAFLGYCIYLNRKRRGDPAFKRRLRD (SEQ ID NO. 20),
FLGYCIYLNRKRRGDPAF (SEQ ID NO. 23),
RGDPAF (SEQ ID NO. 24),
RRGDPAF (SEQ ID NO. 25),
GDPAFKRRLRD (SEQ ID NO. 28) and
GDPAF (SEQ ID NO. 29).

3. A pharmaceutical composition comprising the peptide of claim 1 and a pharmaceutically acceptable carrier.

4. A method of treating a condition selected from a cardiovascular disorder or an ischemia-reperfusion injury related disorder, said method comprising administering to a subject in need thereof a therapeutically effective amount of the peptide of claim 1 and wherein said peptide is administered alone or in combination with another therapeutic agent.

5. The method of claim 4, wherein said cardiovascular disorder is selected from the group consisting of peripheral vascular diseases; coronary artery diseases; myocardial infarction; heart injury; congestive heart failure (CHF); myocardial failure; myocardial hypertrophy; ischemic cardiomyopathy; systolic heart failure; diastolic heart failure; stroke; thrombotic stroke; concentric LV hypertrophy; myocarditis; cardiomyopathy; hypertrophic cardiomyopathy; decompensated heart failure; ischemic myocardial disease; congenital heart disease; angina pectoris; prevention of heart remodeling or ventricular remodeling after myocardial infarction; ischemia-reperfusion injury in ischemic and post-ischemic events; cerebrovascular accident; mitral valve regurgitation; hypertension; hypotension; restenosis; fibrosis; thrombosis; and platelet aggregation.

6. The method of claim 4, wherein said ischemia-reperfusion injury related disorder is associated with ischemic and post-ischemic events in organs and tissues, and the disorder is selected from the group consisting of thrombotic stroke; myocardial infarction; angina pectoris; embolic vascular occlusions; peripheral vascular insufficiency; splanchnic artery occlusion; arterial occlusion by thrombi or embolisms; arterial occlusion by non-occlusive processes; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; and platelet aggregation.

7. The peptide of claim 1, wherein said peptide is a G-protein-coupled receptor (GPCR) agonist.

8. The peptide of claim 7, wherein said GPCR is a Mas family protein.

9. The peptide of claim 1, wherein said peptide induces aortic vasodilation.

10. The peptide of claim 1, wherein said peptide reduces cardiac hypertrophy following heart failure.

11. A peptide consisting of the amino acid sequence of SEQ ID NO: 10.

12. A pharmaceutical composition comprising the peptide of claim 11 and a pharmaceutically acceptable carrier.

* * * * *

SEQUENCE LISTING

```
<160> NUMBER OF SEQ ID NOS: 56

<210> SEQ ID NO 1
<211> LENGTH: 21
<212> TYPE: PRT
<213> ORGANISM: Homo sapiens

<400> SEQUENCE: 1

Thr Ile Pro Met Phe Val Pro Glu Ser Thr Ser Lys Leu Gln Lys Phe
1               5                   10                  15

Thr Ser Trp Phe Met
            20

<210> SEQ ID NO 2
<211> LENGTH: 6
<212> TYPE: PRT
<213> ORGANISM: Homo sapiens

<400> SEQUENCE: 2

Phe Thr Ser Trp Phe Met
1               5

<210> SEQ ID NO 3
<211> LENGTH: 9
<212> TYPE: PRT
<213> ORGANISM: Homo sapiens

<400> SEQUENCE: 3

Leu Gln Lys Phe Thr Ser Trp Phe Met
1               5

<210> SEQ ID NO 4
<211> LENGTH: 21
<212> TYPE: PRT
<213> ORGANISM: Homo sapiens

<400> SEQUENCE: 4

Thr Ile Pro Met Phe Val Pro Glu Ser Thr Ser Thr Leu Gln Lys Phe
1               5                   10                  15

Thr Ser Trp Phe Met
            20

<210> SEQ ID NO 5
<211> LENGTH: 45
```

```
<212> TYPE: PRT
<213> ORGANISM: Homo sapiens

<400> SEQUENCE: 5

Ala Ala Gln Ala Thr Gly Pro Leu Gln Asp Asn Glu Leu Pro Gly Leu
1               5                   10                  15

Asp Glu Arg Pro Pro Arg Ala His Ala Gln His Phe His Lys His Gln
                20                  25                  30

Leu Trp Pro Ser Pro Phe Arg Ala Leu Lys Pro Arg Pro
            35                  40                  45

<210> SEQ ID NO 6
<211> LENGTH: 18
<212> TYPE: PRT
<213> ORGANISM: Homo sapiens

<400> SEQUENCE: 6

Ser Met Cys His Arg Trp Ser Arg Ala Val Leu Phe Pro Ala Ala His
1               5                   10                  15

Arg Pro

<210> SEQ ID NO 7
<211> LENGTH: 18
<212> TYPE: PRT
<213> ORGANISM: Homo sapiens

<400> SEQUENCE: 7

Ser Met Val His Arg Trp Ser Arg Ala Val Leu Phe Pro Ala Ala His
1               5                   10                  15

Arg Pro

<210> SEQ ID NO 8
<211> LENGTH: 23
<212> TYPE: PRT
<213> ORGANISM: Homo sapiens

<400> SEQUENCE: 8

Gly Ile Gly Ser Val Trp His Trp Lys His Arg Val Ala Thr Arg Phe
1               5                   10                  15

Thr Leu Pro Arg Phe Leu Gln
            20

<210> SEQ ID NO 9
<211> LENGTH: 24
<212> TYPE: PRT
<213> ORGANISM: Homo sapiens

<400> SEQUENCE: 9

Phe Leu Gly Tyr Cys Ile Tyr Leu Asn Arg Lys Arg Arg Gly Asp Pro
1               5                   10                  15

Ala Phe Lys Arg Arg Leu Arg Asp
            20

<210> SEQ ID NO 10
<211> LENGTH: 24
<212> TYPE: PRT
<213> ORGANISM: Homo sapiens

<400> SEQUENCE: 10

Phe Leu Gly Tyr Ser Ile Tyr Leu Asn Arg Lys Arg Arg Gly Asp Pro
1               5                   10                  15

Ala Phe Lys Arg Arg Leu Arg Asp
```

20

<210> SEQ ID NO 11
<211> LENGTH: 19
<212> TYPE: PRT
<213> ORGANISM: Homo sapiens

<400> SEQUENCE: 11

Ile Tyr Leu Asn Arg Lys Arg Arg Gly Asp Pro Ala Phe Lys Arg Arg
1               5                   10                  15

Leu Arg Asp

<210> SEQ ID NO 12
<211> LENGTH: 20
<212> TYPE: PRT
<213> ORGANISM: Homo sapiens

<400> SEQUENCE: 12

Phe Ala Phe Leu Gly Tyr Ser Ile Tyr Leu Asn Arg Lys Arg Arg Gly
1               5                   10                  15

Asp Pro Ala Phe
            20

<210> SEQ ID NO 13
<211> LENGTH: 20
<212> TYPE: PRT
<213> ORGANISM: Homo sapiens

<400> SEQUENCE: 13

Phe Ala Phe Leu Gly Tyr Cys Ile Tyr Leu Asn Arg Lys Arg Arg Gly
1               5                   10                  15

Asp Pro Ala Phe
            20

<210> SEQ ID NO 14
<211> LENGTH: 14
<212> TYPE: PRT
<213> ORGANISM: Homo sapiens

<400> SEQUENCE: 14

Arg Trp Ser Arg Ala Val Leu Phe Pro Ala Ala His Arg Pro
1               5                   10

<210> SEQ ID NO 15
<211> LENGTH: 15
<212> TYPE: PRT
<213> ORGANISM: Homo sapiens

<400> SEQUENCE: 15

His Arg Trp Ser Arg Ala Val Leu Phe Pro Ala Ala His Arg Pro
1               5                   10                  15

<210> SEQ ID NO 16
<211> LENGTH: 13
<212> TYPE: PRT
<213> ORGANISM: Homo sapiens

<400> SEQUENCE: 16

Trp Ser Arg Ala Val Leu Phe Pro Ala Ala His Arg Pro
1               5                   10

<210> SEQ ID NO 17
<211> LENGTH: 23
<212> TYPE: PRT

```
<213> ORGANISM: Homo sapiens

<400> SEQUENCE: 17

Ala His Ala Gln His Phe His Lys His Gln Leu Trp Pro Ser Pro Phe
1               5                   10                  15

Arg Ala Leu Lys Pro Arg Pro
            20

<210> SEQ ID NO 18
<211> LENGTH: 11
<212> TYPE: PRT
<213> ORGANISM: Homo sapiens

<400> SEQUENCE: 18

Phe Ala Phe Leu Gly Tyr Ser Ile Tyr Leu Asn
1               5                   10

<210> SEQ ID NO 19
<211> LENGTH: 11
<212> TYPE: PRT
<213> ORGANISM: Homo sapiens

<400> SEQUENCE: 19

Phe Ala Phe Leu Gly Tyr Cys Ile Tyr Leu Asn
1               5                   10

<210> SEQ ID NO 20
<211> LENGTH: 26
<212> TYPE: PRT
<213> ORGANISM: Homo sapiens

<400> SEQUENCE: 20

Phe Ala Phe Leu Gly Tyr Cys Ile Tyr Leu Asn Arg Lys Arg Arg Gly
1               5                   10                  15

Asp Pro Ala Phe Lys Arg Arg Leu Arg Asp
            20                  25

<210> SEQ ID NO 21
<211> LENGTH: 9
<212> TYPE: PRT
<213> ORGANISM: Homo sapiens

<400> SEQUENCE: 21

Phe Leu Gly Tyr Cys Ile Tyr Leu Asn
1               5

<210> SEQ ID NO 22
<211> LENGTH: 10
<212> TYPE: PRT
<213> ORGANISM: Homo sapiens

<400> SEQUENCE: 22

Phe Leu Gly Tyr Cys Ile Tyr Leu Asn Arg
1               5                   10

<210> SEQ ID NO 23
<211> LENGTH: 18
<212> TYPE: PRT
<213> ORGANISM: Homo sapiens

<400> SEQUENCE: 23

Phe Leu Gly Tyr Cys Ile Tyr Leu Asn Arg Lys Arg Arg Gly Asp Pro
1               5                   10                  15

Ala Phe
```

<210> SEQ ID NO 24
<211> LENGTH: 6
<212> TYPE: PRT
<213> ORGANISM: Homo sapiens

<400> SEQUENCE: 24

Arg Gly Asp Pro Ala Phe
1               5

<210> SEQ ID NO 25
<211> LENGTH: 7
<212> TYPE: PRT
<213> ORGANISM: Homo sapiens

<400> SEQUENCE: 25

Arg Arg Gly Asp Pro Ala Phe
1               5

<210> SEQ ID NO 26
<211> LENGTH: 24
<212> TYPE: PRT
<213> ORGANISM: Homo sapiens

<400> SEQUENCE: 26

His Lys Arg Thr Ile Pro Met Phe Val Pro Glu Ser Thr Ser Lys Leu
1               5                   10                  15

Gln Lys Phe Thr Ser Trp Phe Met
            20

<210> SEQ ID NO 27
<211> LENGTH: 10
<212> TYPE: PRT
<213> ORGANISM: Homo sapiens

<400> SEQUENCE: 27

Ala Val Leu Phe Pro Ala Ala His Arg Pro
1               5                   10

<210> SEQ ID NO 28
<211> LENGTH: 11
<212> TYPE: PRT
<213> ORGANISM: Homo sapiens

<400> SEQUENCE: 28

Gly Asp Pro Ala Phe Lys Arg Arg Leu Arg Asp
1               5                   10

<210> SEQ ID NO 29
<211> LENGTH: 5
<212> TYPE: PRT
<213> ORGANISM: Homo sapiens

<400> SEQUENCE: 29

Gly Asp Pro Ala Phe
1               5

<210> SEQ ID NO 30
<211> LENGTH: 4
<212> TYPE: PRT
<213> ORGANISM: Homo sapiens

<400> SEQUENCE: 30

Ile Tyr Leu Asn
1

<210> SEQ ID NO 31
<211> LENGTH: 13
<212> TYPE: PRT
<213> ORGANISM: Homo sapiens

<400> SEQUENCE: 31

Ile Tyr Leu Asn Arg Lys Arg Arg Gly Asp Pro Ala Phe
1               5                   10

<210> SEQ ID NO 32
<211> LENGTH: 21
<212> TYPE: PRT
<213> ORGANISM: Homo sapiens

<400> SEQUENCE: 32

Ala Ala Gln Ala Thr Gly Pro Leu Gln Asp Asn Glu Leu Pro Gly Leu
1               5                   10                  15

Asp Glu Arg Pro Pro
            20

<210> SEQ ID NO 33
<211> LENGTH: 29
<212> TYPE: PRT
<213> ORGANISM: Homo sapiens

<400> SEQUENCE: 33

Ala Ala Gln Ala Thr Gly Pro Leu Gln Asp Asn Glu Leu Pro Gly Leu
1               5                   10                  15

Asp Glu Arg Pro Pro Arg Ala His Ala Gln His Phe His
            20                  25

<210> SEQ ID NO 34
<211> LENGTH: 26
<212> TYPE: PRT
<213> ORGANISM: Homo sapiens

<400> SEQUENCE: 34

Pro Pro Arg Ala His Ala Gln His Phe His Lys His Gln Leu Trp Pro
1               5                   10                  15

Ser Pro Phe Arg Ala Leu Lys Pro Arg Pro
            20                  25

<210> SEQ ID NO 35
<211> LENGTH: 15
<212> TYPE: PRT
<213> ORGANISM: Homo sapiens

<400> SEQUENCE: 35

His Gln Leu Trp Pro Ser Pro Phe Arg Ala Leu Lys Pro Arg Pro
1               5                   10                  15

<210> SEQ ID NO 36
<211> LENGTH: 14
<212> TYPE: PRT
<213> ORGANISM: Homo sapiens

<400> SEQUENCE: 36

Thr Ile Pro Met Phe Val Pro Glu Ser Thr Ser Lys Leu Gln
1               5                   10

<210> SEQ ID NO 37
<211> LENGTH: 14
<212> TYPE: PRT

<213> ORGANISM: Homo sapiens

<400> SEQUENCE: 37

Thr Ile Pro Met Phe Val Pro Glu Ser Thr Ser Thr Leu Gln
1               5                   10

<210> SEQ ID NO 38
<211> LENGTH: 11
<212> TYPE: PRT
<213> ORGANISM: Homo sapiens

<400> SEQUENCE: 38

Thr Ile Pro Met Phe Val Pro Glu Ser Thr Ser
1               5                   10

<210> SEQ ID NO 39
<211> LENGTH: 23
<212> TYPE: PRT
<213> ORGANISM: Homo sapiens

<400> SEQUENCE: 39

Gly Ile Gly Cys Val Trp His Trp Lys His Arg Val Ala Thr Arg Phe
1               5                   10                  15

Thr Leu Pro Arg Phe Leu Gln
            20

<210> SEQ ID NO 40
<211> LENGTH: 25
<212> TYPE: PRT
<213> ORGANISM: Homo sapiens

<400> SEQUENCE: 40

Gly Ile Gly Cys Val Trp His Trp Lys His Arg Val Ala Thr Arg Phe
1               5                   10                  15

Thr Leu Pro Arg Phe Leu Gln Arg Arg
            20                  25

<210> SEQ ID NO 41
<211> LENGTH: 27
<212> TYPE: PRT
<213> ORGANISM: Homo sapiens

<400> SEQUENCE: 41

Gly Ile Gly Cys Val Trp His Trp Lys His Arg Val Ala Thr Arg Phe
1               5                   10                  15

Thr Leu Pro Arg Phe Leu Gln Arg Arg Ser Ser
            20                  25

<210> SEQ ID NO 42
<211> LENGTH: 28
<212> TYPE: PRT
<213> ORGANISM: Homo sapiens

<400> SEQUENCE: 42

Gly Ile Gly Cys Val Trp His Trp Lys His Arg Val Ala Thr Arg Phe
1               5                   10                  15

Thr Leu Pro Arg Phe Leu Gln Arg Arg Ser Ser Arg
            20                  25

<210> SEQ ID NO 43
<211> LENGTH: 22
<212> TYPE: PRT
<213> ORGANISM: Homo sapiens -continued

```
<400> SEQUENCE: 43

Ile Gly Cys Val Trp His Trp Lys His Arg Val Ala Thr Arg Phe Thr
1               5                   10                  15

Leu Pro Arg Phe Leu Gln
            20

<210> SEQ ID NO 44
<211> LENGTH: 24
<212> TYPE: PRT
<213> ORGANISM: Homo sapiens

<400> SEQUENCE: 44

Ile Gly Cys Val Trp His Trp Lys His Arg Val Ala Thr Arg Phe Thr
1               5                   10                  15

Leu Pro Arg Phe Leu Gln Arg Arg
            20

<210> SEQ ID NO 45
<211> LENGTH: 26
<212> TYPE: PRT
<213> ORGANISM: Homo sapiens

<400> SEQUENCE: 45

Ile Gly Cys Val Trp His Trp Lys His Arg Val Ala Thr Arg Phe Thr
1               5                   10                  15

Leu Pro Arg Phe Leu Gln Arg Arg Ser Ser
            20                  25

<210> SEQ ID NO 46
<211> LENGTH: 27
<212> TYPE: PRT
<213> ORGANISM: Homo sapiens

<400> SEQUENCE: 46

Ile Gly Cys Val Trp His Trp Lys His Arg Val Ala Thr Arg Phe Thr
1               5                   10                  15

Leu Pro Arg Phe Leu Gln Arg Arg Ser Ser Arg
            20                  25

<210> SEQ ID NO 47
<211> LENGTH: 20
<212> TYPE: PRT
<213> ORGANISM: Homo sapiens

<400> SEQUENCE: 47

Cys Val Trp His Trp Lys His Arg Val Ala Thr Arg Phe Thr Leu Pro
1               5                   10                  15

Arg Phe Leu Gln
            20

<210> SEQ ID NO 48
<211> LENGTH: 22
<212> TYPE: PRT
<213> ORGANISM: Homo sapiens

<400> SEQUENCE: 48

Cys Val Trp His Trp Lys His Arg Val Ala Thr Arg Phe Thr Leu Pro
1               5                   10                  15

Arg Phe Leu Gln Arg Arg
            20

<210> SEQ ID NO 49
```

```
<211> LENGTH: 24
<212> TYPE: PRT
<213> ORGANISM: Homo sapiens

<400> SEQUENCE: 49

Cys Val Trp His Trp Lys His Arg Val Ala Thr Arg Phe Thr Leu Pro
1               5                   10                  15

Arg Phe Leu Gln Arg Arg Ser Ser
            20

<210> SEQ ID NO 50
<211> LENGTH: 25
<212> TYPE: PRT
<213> ORGANISM: Homo sapiens

<400> SEQUENCE: 50

Cys Val Trp His Trp Lys His Arg Val Ala Thr Arg Phe Thr Leu Pro
1               5                   10                  15

Arg Phe Leu Gln Arg Arg Ser Ser Arg
            20                  25

<210> SEQ ID NO 51
<211> LENGTH: 21
<212> TYPE: PRT
<213> ORGANISM: Homo sapiens

<400> SEQUENCE: 51

Met Pro Ser Val Arg Ser Leu Leu Arg Leu Leu Ala Ala Ala Ala Ala
1               5                   10                  15

Cys Gly Ala Phe Ala
            20

<210> SEQ ID NO 52
<211> LENGTH: 19
<212> TYPE: PRT
<213> ORGANISM: Homo sapiens

<400> SEQUENCE: 52

Met Pro Ser Val Arg Ser Leu Leu Arg Leu Leu Ala Ala Ala Ala Ala
1               5                   10                  15

Cys Gly Ala

<210> SEQ ID NO 53
<211> LENGTH: 17
<212> TYPE: PRT
<213> ORGANISM: Homo sapiens

<400> SEQUENCE: 53

Met His Trp Lys Met Leu Leu Leu Leu Leu Leu Tyr Tyr Asn Ala Glu
1               5                   10                  15

Ala

<210> SEQ ID NO 54
<211> LENGTH: 25
<212> TYPE: PRT
<213> ORGANISM: Homo sapiens

<400> SEQUENCE: 54

Met Ser Lys Ser Cys Gly Asn Asn Leu Ala Ala Ile Ser Val Gly Ile
1               5                   10                  15

Ser Leu Leu Leu Leu Val Val Cys
            20                  25
```

```
<210> SEQ ID NO 55
<211> LENGTH: 33
<212> TYPE: PRT
<213> ORGANISM: Homo sapiens

<400> SEQUENCE: 55

Met Ala His Val Pro Ala Arg Thr Ser Pro Gly Pro Gly Pro Gln Leu
1               5                   10                  15

Leu Leu Leu Leu Leu Pro Leu Phe Leu Leu Leu Leu Arg Asp Val Ala
            20                  25                  30

Gly

<210> SEQ ID NO 56
<211> LENGTH: 19
<212> TYPE: PRT
<213> ORGANISM: Homo sapiens

<400> SEQUENCE: 56

Met Ala Thr Ala Ser Pro Ser Val Phe Leu Leu Met Val Asn Gly Gln
1               5                   10                  15

Val Glu Ser
```